US010202351B2

(12) United States Patent
Schwarz et al.

(10) Patent No.: US 10,202,351 B2
(45) Date of Patent: Feb. 12, 2019

(54) PYRAZOLYL DERIVATIVES AS PEST CONTROL AGENTS

(71) Applicant: BAYER ANIMAL HEALTH GMBH, Leverkusen (DE)

(72) Inventors: Hans-Georg Schwarz, Dorsten (DE); Michael Maue, Langenfeld (DE); Werner Hallenbach, Monheim (DE); Ulrich Görgens, Ratingen (DE); Daniela Portz, Vettweiß (DE); Kerstin Ilg, Köln (DE); Johannes Köbberling, Neuss (DE); Andreas Turberg, Haan (DE)

(73) Assignee: BAYER ANIMAL HEALTH GMBH, Leverkusen (DE)

( * ) Notice: Subject to any disclaimer, the term of this patent is extended or adjusted under 35 U.S.C. 154(b) by 0 days.

(21) Appl. No.: 15/554,501

(22) PCT Filed: Mar. 9, 2016

(86) PCT No.: PCT/EP2016/054955
§ 371 (c)(1),
(2) Date: Aug. 30, 2017

(87) PCT Pub. No.: WO2016/142394
PCT Pub. Date: Sep. 15, 2016

(65) Prior Publication Data
US 2018/0044298 A1 Feb. 15, 2018

(30) Foreign Application Priority Data

Mar. 10, 2015 (EP) ..................... 15158341

(51) Int. Cl.
| C07D 231/12 | (2006.01) |
| C07D 403/12 | (2006.01) |
| C07D 401/14 | (2006.01) |
| C07D 401/04 | (2006.01) |
| C07D 401/12 | (2006.01) |
| C07D 409/12 | (2006.01) |
| C07D 403/04 | (2006.01) |

(52) U.S. Cl.
CPC ......... *C07D 231/12* (2013.01); *C07D 401/04* (2013.01); *C07D 401/12* (2013.01); *C07D 401/14* (2013.01); *C07D 403/04* (2013.01); *C07D 403/12* (2013.01); *C07D 409/12* (2013.01)

(58) Field of Classification Search
CPC .. C07D 231/12; C07D 401/04; C07D 401/12; C07D 401/14; C07D 403/04; C07D 403/12; C07D 409/12
See application file for complete search history.

(56) References Cited

U.S. PATENT DOCUMENTS

| 6,069,157 | A | 5/2000 | Banks | |
| 8,685,964 | B2 * | 4/2014 | Bretschneider | ........ A01N 43/56 514/229.2 |
| 2006/0063934 | A1 * | 3/2006 | Hagihara | ............. A61K 31/501 546/275.4 |
| 2011/0166143 | A1 | 7/2011 | Bretschneider et al. | |
| 2012/0165345 | A1 | 6/2012 | Bretschneider et al. | |

FOREIGN PATENT DOCUMENTS

| WO | 2011/045224 A1 | 4/2011 |
| WO | 2011/113756 A1 | 9/2011 |
| WO | 2012/000896 A2 | 1/2012 |

OTHER PUBLICATIONS

International Search of PCT/EP2016/054955 dated Apr. 12, 2016.

* cited by examiner

*Primary Examiner* — Valerie Rodriguez-Garcia
(74) *Attorney, Agent, or Firm* — McBee Moore Woodward & Vanik IP, LLC

(57) ABSTRACT

The invention comprises novel pyrazolyl derivatives of the general formula (I)

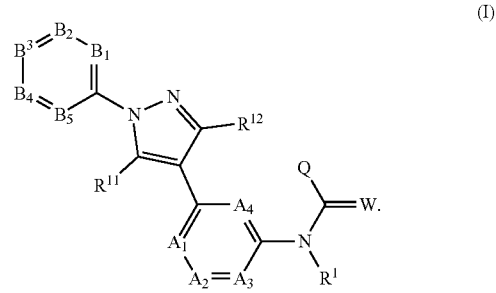

Also described are processes for preparing the compounds of the formula (I). The compounds according to the invention are especially suitable for controlling insects and arachnids in agriculture, and ectoparasites in veterinary medicine.

17 Claims, No Drawings

PYRAZOLYL DERIVATIVES AS PEST CONTROL AGENTS

CROSS REFERENCE TO RELATED APPLICATIONS

This application is a § 371 National State Application of PCT/EP2016/054955, filed Mar. 9, 2016, which claims priority to European Application No. 15158341.6 filed Mar. 10, 2015.

BACKGROUND OF THE INVENTION

Field of the Invention

The present application relates to pyrazolyl derivatives, to processes for preparation thereof and to the use thereof for controlling animal pests, especially arthropods and in particular insects and arachnids.

Description of Related Art

WO2011113756-A1 describes certain triazolyl derivatives as insecticidal compounds. Here, the general formula (A) comprises in its definitions of $A^1$ to $A^4$ CX (X represents hydrogen, halogen, cyano, $C_1$-$C_4$-alkyloxy, $C_1$-$C_4$-alkyl or $C_1$-$C_4$-haloalkyl) or nitrogen, where $Q^2$ denotes certain phenyl or pyridyl substituents.

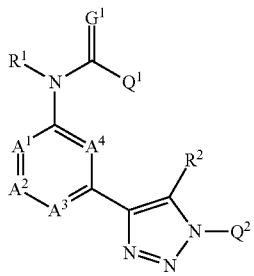

(A)

SUMMARY

It was an object of the present invention to provide compounds which broaden the spectrum of the pesticides in various aspects and/or improve their activity.

It has now been found that, surprisingly, certain pyrazolyl derivatives and their N-oxides and salts have biological properties superior to the prior art and are especially suitable for controlling animal pests, and therefore have particularly good usability in the agrochemical sector and in the animal health sector.

Abstract

One aspect of the present invention relates to compounds of the formula (I)

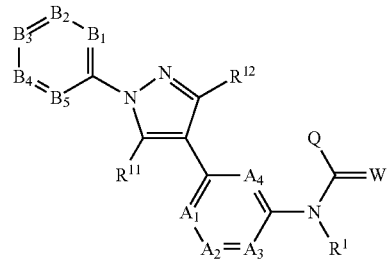

(I)

where
$R^1$ is hydrogen, optionally substituted $C_1$-$C_6$-alkyl, $C_3$-$C_6$-alkenyl, $C_3$-$C_6$-alkynyl, $C_3$-$C_7$-cycloalkyl, $C_1$-$C_6$-alkylcarbonyl, $C_1$-$C_6$-alkoxycarbonyl, aryl($C_1$-$C_3$)-alkyl, heteroaryl($C_1$-$C_3$)-alkyl;
the chemical moieties
$A_1$ represents $CR^2$ or nitrogen (N),
$A_2$ represents $CR^3$ or N,
$A_3$ represents $CR^4$ or N,
$A_4$ represents $CR^5$ or N,
$B_1$ represents $CR^6$ or N,
$B_2$ represents $CR^7$ or N,
$B_3$ represents $CR^8$ or N,
$B_4$ represents $CR^9$ or, and
$B_5$ represents $CR^{10}$ or N;
but not more than three of the chemical moieties $A_1$ to $A_4$ simultaneously represent nitrogen and not more than three of the moieties $B_1$ to $B_5$ simultaneously represent nitrogen;
$R^2$, $R^3$, $R^4$, $R^5$, $R^6$, $R^7$, $R^9$ and $R^{10}$ independently of one another represent hydrogen, halogen, cyano, nitro, optionally substituted $C_1$-$C_6$-alkyl, $C_3$-$C_7$-cycloalkyl, $C_1$-$C_6$-alkoxy, N—($C_1$-$C_6$-alkoxy)imino-$C_1$-$C_3$-alkyl, $C_1$-$C_6$-alkylsulfanyl, $C_1$-$C_6$-alkylsulfinyl, $C_1$-$C_6$-alkylsulfonyl, N—($C_1$-$C_6$-alkyl)amino or N,N-di($C_1$-$C_6$-alkyl)amino, $C_1$-$C_6$-alkylsulfonylamino N—($C_1$-$C_6$-alkyl)-$C_1$-$C_6$-alkylsulfonylamino;
$R^8$ represents halogen, cyano, nitro, in each case an optionally substituted moiety selected from $C_1$-$C_6$-alkyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulfanyl, $C_1$-$C_6$-alkylsulfinyl, $C_1$-$C_6$-alkyl sulfonyl, N—$C_1$-$C_6$-alkylamino and N,N-di-$C_1$-$C_6$-alkylamino, preferably halogen, cyano, nitro or halogenated $C_1$-$C_6$-alkyl;
$R^{11}$ and $R^{12}$ independently of one another represents hydrogen, halogen, cyano, nitro, amino or in each case an optionally halogenated moiety selected from $C_1$-$C_6$-alkyl, $C_1$-$C_6$-alkyloxy, $C_1$-$C_6$-alkylcarbonyl, $C_1$-$C_6$-alkylsulfanyl, $C_1$-$C_6$-alkylsulfinyl, $C_1$-$C_6$-alkylsulfonyl;
W is oxygen or sulfur;
Q is hydrogen, amino, a moiety selected from $C_1$-$C_6$-alkyl, $C_2$-$C_6$-alkenyl, $C_2$-$C_6$-alkynyl, $C_3$-$C_6$-cycloalkyl, $C_2$-$C_5$-heterocyclyl, $C_1$-$C_4$-alkoxy, $C_1$-$C_6$-alkyl-$C_3$-$C_6$-cycloalkyl, $C_3$-$C_6$-cycloalkyl-$C_1$-$C_6$-alkyl, aryl-($C_1$-$C_3$)-alkyl, heteroaryl-($C_1$-$C_3$)-alkyl, $C_1$-$C_4$-alkoxycarbonyl, in each case optionally monsubstituted to heptasubstituted independently of one another by cyano, alkoxy and alkoxycarbonyl, or for a moiety N—$C_1$-$C_4$-alkylamino, N—$C_1$-$C_4$-alkylcarbonylamino, N,N-di-$C_1$-$C_4$-alkylamino and $C_1$-$C_4$-alkylsulfonylamino, or a halogenated moiety selected from $C_1$-$C_6$-alkyl, $C_2$-$C_6$-alkenyl, $C_2$-$C_6$-alkynyl, $C_3$-$C_6$-cycloalkyl, $C_2$-$C_5$-heterocyclyl, $C_1$-$C_4$-alkoxy, $C_1$-$C_6$-alkyl-$C_3$-$C_6$-cycloalkyl, $C_3$-$C_6$-cycloalkyl-$C_1$-$C_6$-alkyl, aryl-($C_1$-$C_3$)-alkyl, heteroaryl-($C_1$-$C_3$)- alkyl, $C_1$-$C_4$-alkoxycarbonyl, or for a moiety N—$C_1$-$C_4$-alkylamino, N—$C_1$-$C_4$-alkylcarbonylamino, N,N-di-$C_1$-$C_4$-alkylamino and $C_1$-$C_4$-alkylsulfonylamino; or Q is an aryl substituted by 0, 1, 2, 3 or 4 V substituents or a 5- or 6-membered heteroaryl substituted by 0, 1, 2, 3 or 4 V substituents, where V independently of one another represents halogen, cyano, nitro, a moiety selected from $C_1$-$C_6$-alkyl, $C_2$-$C_4$-alkenyl, $C_2$-$C_4$-alkynyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulfanyl, $C_1$-$C_6$-alkylsulfinyl, $C_1$-$C_6$-alkylsulfonyl and N,N-di-($C_1$-$C_6$-alkyl)amino, in each case optionally monosubstituted to heptasubstituted by cyano, alkoxy and alkoxycarbonyl, or a halogenated moiety selected from $C_1$-$C_6$-alkyl, $C_2$-$C_4$-alkenyl, $C_2$-$C_4$-alkynyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulfanyl, $C_1$-$C_6$-alkylsulfinyl, $C_1$-$C_6$-alkylsulfonyl and N,N-di-($C_1$-$C_6$-alkyl)amino;

and salts, N-oxides and tautomeric forms of the compound of the formula (I).

DETAILED DESCRIPTION OF A PREFERRED EMBODIMENT

A preferred embodiment is directed to a compound as described above where $B_1$ is $CR^6$, $B_2$ is $CR^7$, $B_3$ is $CR^8$, $B_4$ is $CR^9$ and $B_5$ is $CR^{10}$.

A further preferred embodiment is directed to a compound as described above where $R^6$ is halogen or optionally halogenated $C_1$-$C_6$-alkyl or optionally halogenated $C_1$-$C_6$-alkoxy, $R^7$ is hydrogen, $R^8$ is $C_1$-$C_6$-halogenated alkyl, $R^9$ is hydrogen and $R^{10}$ is halogen or optionally halogenated $C_1$-$C_6$-alkyl or optionally halogenated $C_1$-$C_6$-alkoxy. A more preferred embodiment is directed to a compound as described above where $R^6$ is halogen or optionally halogenated $C_1$-$C_6$-alkyl, $R^7$ is hydrogen, $R^8$ is halogenated $C_1$-$C_6$-alkyl, $R^9$ is hydrogen and $R^{10}$ is halogen or optionally halogenated $C_1$-$C_6$-alkyl.

A further preferred embodiment is directed to a compound as described above, where $R^{11}$ and $R^{12}$ are hydrogen and W is oxygen.

A further preferred embodiment is directed to a compound as described above, where $A_1$ is $CR^2$, $A_2$ is $CR^3$ or N, $A_3$ is $CR^4$ or N and $A_4$ is $CR^5$ and $R^2$ is hydrogen or $C_1$-$C_6$-alkyl and $R^3$, $R^4$ and $R^5$ are each independently of one another hydrogen, halogen, CN, optionally halogenated $C_1$-$C_6$-alkyl or N,N-di-$C_1$-$C_6$-alkylamino.

A further preferred embodiment is directed to a compound as described above, where Q is $C_1$-$C_6$-alkyl optionally substituted by one, two or three substituents selected from the group consisting of oxo, cyano, nitro and amino, halogenated ($C_1$-$C_6$)-alkyl, $C_3$-$C6$-alkyl optionally substituted by one, two or three substituents selected from the group consisting of halogen, cyano, nitro, $C_1$-$C_3$-alkyl and amino, $C_2$-$C5$-heterocyclyl optionally substituted by one, two or three substituents selected from the group consisting of halogen, cyano, nitro, $C_1$-$C_3$-alkyl and amino, an aryl substituted by 0, 1, 2, 3 or 4 V substituents or a 5- or 6-membered heteroaryl substituted by 0, 1, 2, 3 or 4 V substituents, wherein V is each independently of one another halogen, cyano, $C_1$-$C_6$-alkyl or $C_1$-$C_6$-alkoxy.

A further preferred embodiment is directed to a compound as described above, where Q is cyclopropyl optionally substituted by cyano or $C_1$-$C_3$-alkyl, or thietanyl (thiacyclobutanyl) optionally substituted by cyano or $C_1$-$C_3$-alkyl, or phenyl substituted by 0, 1 or 2 V substituents each selected independently of one another from the group consisting of F, Cl, $C_1$-$C_3$-alkoxy (such as methoxy and ethoxy), $C_1$-$C_3$-alkyl (such as methyl), halogenated $C_1$-$C_3$-alkyl (such as $CF_3$) and cyano, or pyridyl, pyrimidinyl and thiophenyl substituted by 0, 1 or 2 V substituents each selected independently of one another from the group consisting of F, Cl, $C_1$-$C_3$-alkyl (such as methyl), halogenated $C_1$-$C_3$-alkyl (such as $CF_3$) and cyano, or pyridyl, pyrimidinyl, thienyl, oxazolyl or thiophenyl substituted by 0, 1 or 2 V substituents each selected independently of one another from the group consisting of F, Cl, $C_1$-$C_3$-alkyl (such as methyl), halogenated $C_1$-$C_3$-alkyl (such as $CF_3$) and cyano.

A further preferred embodiment is directed to a compound as described above, where $A_2$ represents $CR^2$, where $R^2$ represents hydrogen, $A_2$ represents $CR^3$ or N, where R3 represents hydrogen, $A_3$ represents $CR^4$ or N, where $R^4$ is hydrogen, Cl, F, or $C_1$-$C_3$-alkyl (such as $CH_3$) or —N($C_1$-$C_3$-alkyl)$_2$ (such as —N($CH_3$)$_2$), $A_4$ represents $CR^5$, where $R^5$ represents hydrogen or F, $B_1$ represents $CR^6$, $B_2$ represents $CR^7$, where $R^7$ represents hydrogen, $B_3$ represents $CR^8$, $B_4$ represents $CR^9$, where $R^9$ represents hydrogen, $B_5$ represents $CR^{10}$ $R^6$ represents Cl, Br or $C_1$-$C_3$-alkyl (such as $CH_3$), $R^8$ represents perhalogeniertes $C_1$-$C_6$-alkyl, more preferably perfluorinated $C_1$-$C_4$-alkyl such as $CF_3$, $C_2F_5$, $C_3F_7$, $C_4F_9$, $R^{10}$ represents Cl, $C_1$-$C_3$-alkyl (such as methyl) or perfluorinated $C_1$-$C_3$-alkyl (such as $CF_3$), $R^{11}$ and $R^{12}$ represent hydrogen, W is oxygen, Q represents (a) $C_3$-$C_6$-cycloalkyl optionally substituted by one substituent selected from the group consisting of halogen, $C_1$-$C_3$-alkyl and cyano (such as, for example, cyclopropyl optionally substituted by cyano or $C_1$-$C_3$-alkyl), (b) $C_2$-$C_5$-heterocyclyl optionally substituted by one substituent selected from the group consisting of halogen or cyano, such as, for example, thietanyl (thiacyclobutanyl) optionally substituted by cyano or $C_1$-$C_3$-alkyl, (c) an aryl substituted by 0, 1 or 2 V substituents or a 5- or 6-membered heteroaryl substituted by 0, 1, 2, 3 or 4 V substituents, wherein V is each independently of one another halogen (e.g. F, Cl), cyano, optionally halogenated $C_1$-$C_6$-alkyl, optionally halogenated $C_1$-$C_6$-alkoxy (such as phenyl optionally substituted by 0, 1 or 2 V substituents each selected independently of one another from the group consisting of halogen (such as F, Cl), $C_1$-$C_3$-alkoxy (such as methoxy and ethoxy), $C_1$-$C_3$-alkyl (such as methyl), halogenated $C_1$-$C_3$-alkyl (such as $CF_3$) and cyano; or pyridyl, pyrimidinyl, thienyl, oxazolyl or thiophenyl optionally substituted by 0, 1 or 2 V substituents V each selected independently of one another from the group consisting of halogen (such as F, Cl), $C_1$-$C_3$-alkyl (such as methyl) halogenated $C_1$-$C_3$-alkyl (such as $CF_3$) and cyano).

A further preferred embodiment is directed to a compound as described above, where a compound of the formula (I) is a compound of the formula (I'):

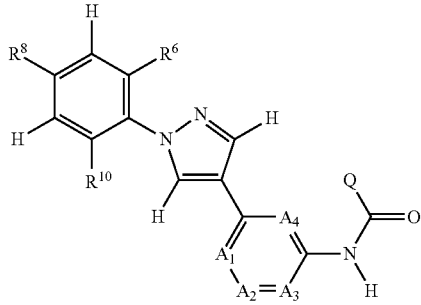

(I')

where $A_1$, $A_2$, $A_3$, $A_4$, $R_6$, $R^8$, $R^{10}$ and Q are defined as described above.

A further preferred embodiment is directed to a compound as described above, where a compound of the formula (I) is a compound of the formula (Ia):

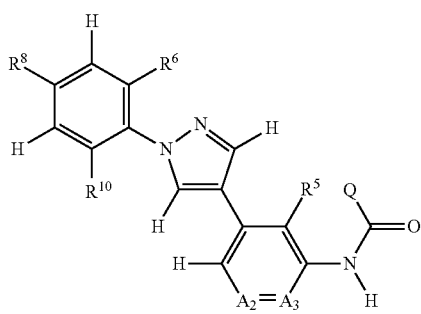

(Ia)

where $A_2$, $A_3$, $R^5$, $R^6$, $R^8$, $R^{10}$ and Q are defined as described above.

A further preferred embodiment is directed to a compound as described above, where a compound of the formula (I) is a compound of the formula (Ib):

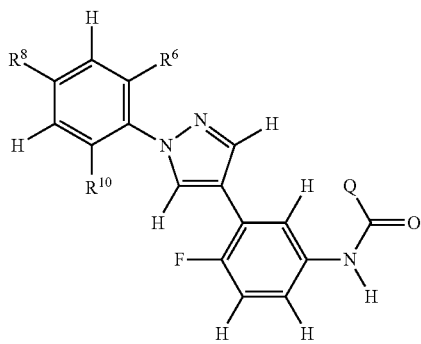

(Ib)

where $R^6$, $R^8$, $R^{10}$ and Q are defined as described above.

A further aspect relates to a compound of the formula (II)

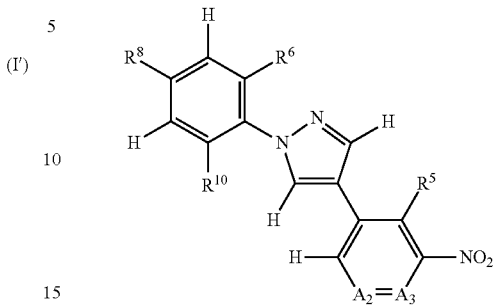

(II)

where $A_2$, $A_3$, $R^5$, $R^6$, $R^8$ and $R^{10}$ are defined as described above.

A further aspect relates to a compound of the formula (III)

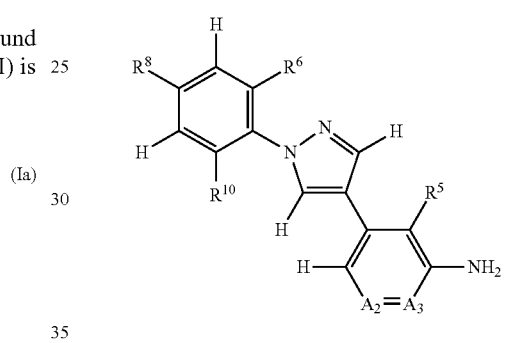

(III)

where $A_2$, $A_3$, $R^5$, $R^6$, $R^8$ and $R^{10}$ are defined as described above.

A further aspect relates to a pharmaceutical composition comprising at least one compound as described above.

A further aspect relates to compounds as described above specifically for use as a medicaments.

A further aspect relates to the use of compounds as described above for production of pharmaceutical compositions for control of parasites in animals.

A further aspect relates to the use of compounds as described above for protecting the propagation material of plants, preferably for protecting seed.

Definitions

The person skilled in the art is aware that the expressions "a" or "an" as used in the present application may, depending on the situation, mean "one (1)", "one (1) or more" or "at least one (1)".

The expression "optionally substituted" means, if no specific substituents are stated, that the group in question may be mono- or polysubstituted by a substituent $M^1$, where in the case of polysubstitutions the substituents $M^1$ can be identical or different.

It is obvious to the person skilled in the art that examples given in the present application are not to be considered as limiting, but rather merely describe some embodiments in more detail.

The expressions "($C_n$-$C_m$)" and "$C_n$-$C_m$-" are exchangeable and relate to the minimum and maximum number of carbon atoms in an organic group. "($C_1$-$C_6$)" and "$C_1$-$C_6$-"

alkyl, for example, relate to an alkyl group having 1, 2, 3, 4, 5 or 6 carbon atoms. The expressions "($C_n$)" and "$C_n$—" are likewise exchangeable and relate to the number of carbon atoms in an organic group. The expressions "$C_3$-cycloalkyl" and "($C_3$)-alkyl", for example, relate to cyclopropyl.

In the definitions of the symbols given in the above formulae, collective terms which are generally representative of the following substituents were used:

According to the invention, "alkyl"—on its own or as a part of a chemical group—represents straight-chain or branched hydrocarbons having preferably 1 to 6 carbon atoms, particularly preferably 1, 2, 3 or 4 carbon atoms, for example methyl, ethyl, n-propyl, isopropyl, n-butyl, isobutyl, s-butyl, t-butyl. The alkyl radicals according to the invention may optionally be substituted by one or more identical or different radicals $M^1$.

According to the invention, "alkenyl"—on its own or as a part of a chemical group—represents straight-chain or branched hydrocarbons having preferably 2 to 6 carbon atoms, particularly preferably 2, 3 or 4 carbon atoms, and at least one double bond, for example vinyl, 2-propenyl, 2-butenyl, 3-butenyl, 1-methyl-2-propenyl, 2-methyl-2-propenyl, 2-pentenyl, 3-pentenyl, 4-pentenyl, etc. The alkenyl radicals according to the invention may optionally be substituted by one or more identical or different radicals $M^1$.

According to the invention, "alkynyl"—on its own or as a part of a chemical group—represents straight-chain or branched hydrocarbons having preferably 2 to 6 carbon atoms, particularly preferably 2, 3 or 4 carbon atoms, and at least one triple bond, for example ethynyl, 2-propynyl, 2-butynyl, 3-butynyl, 1-methyl-2-propynyl, 2-pentynyl, 3-pentynyl, 4-pentynyl, 1-methyl-3-butynyl, etc. The alkynyl radicals according to the invention may optionally be substituted by one or more identical or different radicals M1.

According to the invention, "cycloalkyl"—on its own or as part of a chemical group—represents mono-, bi- or tricyclic hydrocarbons preferably having 3 to 10 carbons, for example cyclopropyl, cyclobutyl, cyclopentyl, cyclohexyl, bicyclo[2.2.1]heptyl, bicyclo[2.2.2]octyl or adamantyl, particularly preferably cycloalkyl radicals having 3, 4, 5, 6 or 7 carbon atoms, for example cyclopropyl or cyclobutyl. The cycloalkyl radicals according to the invention may optionally be substituted by one or more identical or different radicals M1.

According to the invention, "alkylcycloalkyl" represents mono-, bi- or tricyclic alkylcycloalkyl preferably having 4 to 10 or 4 to 7 carbon atoms, particularly preferably alkylcycloalkyl radicals having 4, 5 or 7 carbon atoms, for example ethylcyclopropyl or 4-methylcyclohexyl, where the alkylcycloalkyl is attached via the cycloalkyl moiety to the parent structure. The alkylcycloalkyl radicals according to the invention may optionally be substituted by one or more identical or different radicals $M^1$.

According to the invention, "cycloalkylalkyl" represents mono-, bi- or tricyclic cycloalkylalkyl preferably having 4 to 10 or 4 to 7 carbon atoms, particularly preferably cycloalkylalkyl radicals having 4, 5 or 7 carbon atoms, inter alia cyclopropylmethyl or cyclobutylmethyl, where the alkylcycloalkyl is attached via the alkyl moiety to the parent structure. The cycloalkylalkyl radicals according to the invention may optionally be substituted by one or more identical or different radicals $M^1$.

According to the invention, "alkoxy" represents straight-chain or branched O-alkyl preferably having 1 to 6 carbon atoms, more preferably alkoxy groups having 1 to 4 carbon atoms, for example methoxy, ethoxy, n-propoxy, iso-propoxy, n-butoxy, isobutoxy, s-butoxy or t-butoxy. The alkoxy groups according to the invention may optionally be substituted by one or more identical or different radicals M1.

According to the invention, "alkylsulfanyl" represents straight-chain or branched S-alkyl preferably having 1 to 6 carbon atoms, more preferably alkylsulfanyl groups having 1 to 4 carbon atoms, for example methylthio, ethylthio, n-propylthio, isopropylthio, n-butylthio, isobutylthio, s-butylthio and t-butylthio. The alkylsulfanyl groups according to the invention may optionally be substituted by one or more identical or different radicals $M^1$.

According to the invention, "alkylsulfinyl" represents straight-chain or branched alkylsulfinyl preferably having 1 to 6 carbon atoms, more preferably alkylsulfinyl groups having 1 to 4 carbon atoms, for example methylsulfinyl, ethylsulfinyl, n-propylsulfinyl, isopropylsulfinyl, n-butylsulfinyl, isobutylsulfinyl, s-butylsulfinyl and t-butylsulfinyl. The alkylsulfinyl groups according to the invention may optionally be substituted by one or more identical or different radicals $M^1$.

According to the invention, "alkylsulfonyl" represents straight-chain or branched alkylsulfonyl preferably having 1 to 6 carbon atoms, more preferably alkylsulfonyl groups having 1 to 4 carbon atoms, for example methylsulfonyl, ethylsulfonyl, n-propylsulfonyl, isopropylsulfonyl, n-butylsulfonyl, isobutylsulfonyl, s-butylsulfonyl and t-butylsulfonyl. The alkylsulfonyl groups according to the invention may optionally be substituted by one or more identical or different radicals $M^1$.

According to the invention, "acyl" represents radicals containing an $X^1$—C(=O)—$X^2$ group, where $X^1$ and $X^2$ independently of one another represent an organic radical as defined in the present application or represent hydrogen or represent a bond to the parent structure of a compound of the formula (I). In particular, "acyl" is understood to mean organic acids, esters, aldehydes, alkylcarbonyl (alkyl-C(=O)—) and amides. Preferably, $X^1$ and $X^2$ each independently of one another represent a group, optionally substituted by one or more identical or different radicals $M^1$, selected from alkyl, alkylene (—$C_nH_{2n}$—), alkoxy, alkoxylene (—O—$C_nH_{2n}$—), amino, mono- or dialkylamino, or hydrogen, or a radical $X^1$ or $X^2$ represents a bond to the parent structure of a compound of the formula (I).

According to the invention "alkylcarbonyl" represents straight-chain or branched alkyl-C(=O)-preferably having 2 to 7 carbon atoms (including the carbon atom of the C(=O) group), more preferably alkylcarbonyl radicals having 2 to 5 carbon atoms (($C_1$-$C_4$)-alkyl-C(=O)—), such as methylcarbonyl, ethylcarbonyl, n-propylcarbonyl, isopropylcarbonyl, s-butylcarbonyl and t-butylcarbonyl. The alkylcarbonyl groups according to the invention may optionally be substituted by one or more identical or different radicals $M^1$.

According to the invention, "cycloalkylcarbonyl" represents straight-chain or branched cycloalkylcarbonyl preferably having 3 to 10 carbon atoms in the cycloalkyl moiety, more preferably cycloalkylcarbonyl having 3, 5 or 7 carbon atoms in the cycloalkyl moiety, for example cyclopropylcarbonyl, cyclobutylcarbonyl, cyclopentylcarbonyl, cyclohexylcarbonyl, cycloheptylcarbonyl, cyclooctylcarbonyl, bicyclo[2.2.1]heptyl, bicyclo[2.2.2]octylcarbonyl and adamantylcarbonyl. The cycloalkylcarbonyl groups according to the invention may optionally be substituted by one or more identical or different radicals $M^1$.

According to the invention, "alkoxycarbonyl"—on its own or as part of a chemical group—represents straight-chain or branched alkoxycarbonyl preferably having 1 to 6 carbon atoms, more preferably having 1, 2, 3 or 4 carbon atoms in the alkoxy moiety, for example methoxycarbonyl, ethoxycarbonyl, n-propoxycarbonyl, isopropoxycarbonyl, s-butoxycarbonyl and t-butoxycarbonyl. The alkoxycarbonyl groups according to the invention may optionally be substituted by one or more identical or different radicals $M^1$.

According to the invention, "halogen" represents fluorine (F), chlorine ($C_1$), bromine (Br) or iodine (I).

The expressions "haloalkyl", "haloalkenyl", "haloalkynyl", "haloalkylcarbonyl" "haloalkoxy", "haloalkoxycarbonyl", "haloalkylsulfanyl", "haloalkylsulfinyl" or "haloalkylsulfonyl" or "halogenated alkyl", "halogenated alkenyl", "halogenated alkynyl", "halogenated alkylcarbonyl" "halogenated alkoxy", "halogenated alkoxycarbonyl", "halogenated alkylsulfanyl", "halogenated alkylsulfinyl" or "halogenated alkylsulfonyl" as used herein refer to an alkyl, alkenyl, alkynyl, alkylcarbonyl, alkoxy, alkoxycarbonyl, alkylsulfanyl, alkylsulfinyl or alkylsulfonyl group (each preferably having one to 6 carbon atoms or more, preferably having one, two, three or four carbon atoms) chemically substituted by at least one halogen and are subsumed under the term "substituted" group. The halogen group may be mono- or polysubstituted by halogen up to the maximum possible number of substituents (perhalogenated) (e.g. C(halogen)$_3$, C$_2$(halogen)$_5$, C$_3$(halogen)$_7$, C$_4$(halogen)$_9$). In the case of polysubstitution by halogen, the halogen atoms may be identical or different, and may all be bonded to one carbon atom or may be bonded to a plurality of carbon atoms. Here, halogen represents in particular fluorine, chlorine, bromine or iodine, preferably fluorine or chlorine and particularly preferably fluorine. In a preferred embodiment, perhalogenated groups are maximally substituted by only one type of halogen, e.g. perfluorinated methyl (trifluoromethyl; $CF_3$) or perfluorinated ethyl (pentafluoroethyl; $C_2F_5$) or perfluorinated propyl (heptafluoropropyl; $C_3F_7$). The number of halogen substituents in a halogenated group having $C_m$ atoms (where m is preferably 1, 2, 3, 4, 5 or 6) is between 1 and 2*m+1 (e.g. 1, 2 or 3 if m=1; 1, 2, 3, 4, 5 if m=2; 1, 2, 3, 4, 5, 6, 7 if m=3; 1, 2, 3, 4, 5, 6, 7, 8, 9 if m=4 etc.). Some examples of "halogenated alkyl", "halogenated alkenyl", "halogenated alkynyl", "halogenated alkylcarbonyl", "halogenated alkoxy", "halogenated alkoxycarbonyl", "halogenated alkylsulfanyl", "halogenated alkylsulfinyl" or "halogenated alkylsulfonyl" are trichloromethyl ($CCl_3$), trifluoromethyl ($CF_3$), chlorodifluoromethyl ($CClF_2$), dichlorofluoromethyl ($CCl_2F$), 2,2-difluoroethyl ($F_2HCCH_2$), 2,2,2-trifluoroethyl ($F_3CCH_2$), pentafluoroethyl ($C_2F_5$), 2,2-difluoroethenyl ($CHCF_2$), 2-chloroethynyl (CHCCl), trifluoromethoxy —$OCF_3$, difluoromethoxy —$OCHF_2$, 1,1,2,2-tetrafluoroethylthio, 2-chloro-1,1,2-trifluoroethylsulfinyl, trichloromethylsulfonyl, etc. The halo groups according to the invention, if specified, can optionally be substituted by one or more identical or different radicals $M^1$, but at least one halogen substituent must be present in the parent structure. An example of an $M^1$-substituted haloalkyl is 2-cyano-2,2-difluoroethyl ($C(CN)F_2CH_2$).

An amino group (—$NH_2$) may optionally be substituted by one or more identical or different radicals $M^1$.

Substituted amino such as mono- or disubstituted amino is a radical from the group of the substituted amino radicals N-substituted, for example, by one or two identical or different radicals from the group of alkyl, hydroxyl, amino, alkoxy, acyl and aryl; preferably N-mono- and N,N-dialkylamino (e.g. methylamino, ethylamino, N,N-dimethylamino, N,N-diethylamino, N,N-di-n-propylamino, N,N-diisopropylamino or N,N-dibutylamino), N-mono- or N,N-dialkoxyalkylamino groups (e.g. N-methoxymethylamino, N-methoxyethylamino, N,N-di(methoxymethyl)amino or N,N-di(methoxyethyl)amino), N-mono- and N,N-diarylamino, such as optionally substituted anilines, acylamino, N,N-diacylamino, N-alkyl-N-arylamino, N-alkyl-N-acylamino and saturated N-heterocycles; preference is given to alkyl radicals having 1 to 4 carbon atoms; aryl is preferably phenyl or optionally substituted phenyl; acyl is as defined further above, preferably ($C_1$-$C_4$)alkyl-C(═O)—.

Substituted amino also includes quaternary ammonium compounds (salts) having four organic substituents on the nitrogen atom.

According to the invention, "hydroxyalkyl" represents a straight-chain or branched alcohol preferably having 1 to 6 carbon atoms, more preferably 1, 2, 3 or 4 carbon atoms, for example methanol, ethanol, n-propanol, isopropanol, n-butanol, isobutanol, s-butanol and t-butanol. The hydroxyalkyl groups according to the invention may be substituted by one or more identical or different radicals $M^1$.

According to the invention, "alkylaminocarbonyl" represents straight-chain or branched alkylaminocarbonyl having preferably 1 to 6 carbon atoms, more preferably 1, 2, 3 or 4 carbon atoms in the alkyl moiety, for example methylaminocarbonyl (—$CONHCH_3$), ethylaminocarbonyl, n-propylaminocarbonyl, isopropylaminocarbonyl, s-butylaminocarbonyl and t-butylaminocarbonyl. The alkylaminocarbonyl groups according to the invention may optionally be substituted by one or more identical or different radicals $M^1$.

According to the invention, "N,N-dialkylaminocarbonyl" (—C(═O)N(alkyl)$_2$) represents straight-chain or branched N,N-dialkylaminocarbonyl having preferably 1 to 6 carbon atoms per alkyl, more preferably 1, 2, 3 or 4 carbon atoms per alkyl, for example N,N-dimethylaminocarbonyl (—C(═O)N($CH_3$)$_2$), N,N-diethylaminocarbonyl, N,N-di(n-propylamino)carbonyl, N,N-di(isopropylamino)carbonyl and N,N-di(s-butylamino)carbonyl. The N,N-dialkylaminocarbonyl groups according to the invention may optionally be substituted by one or more identical or different radicals $M^1$.

"Carbocycle", unless defined differently elsewhere, is in particular cycloalkyl, cycloalkenyl or aryl. A carbocycle is in particular mono-, bi- or tricyclic $C_6$- to $C_{14}$-aryl. A carbocycle may optionally be substituted by one or more identical or different radicals $M^1$.

According to the invention, "aryl" represents a mono-, bi- or polycyclic aromatic system having preferably 6 to 14, in particular 6 to 10 ring carbon atoms such as, for example, phenyl, naphthyl, anthryl, phenanthrenyl, preferably phenyl. In addition, aryl also represents polycyclic systems such as tetrahydronaphthyl, indenyl, indanyl, fluorenyl, biphenyl, where the bonding site is on the aromatic system. The aryl groups according to the invention may optionally be substituted by one or more identical or different radicals $M^1$.

According to the invention, "arylalkyl" represents an aryl-substituted alkyl radical having preferably 6 to 14, in particular 6 to 10 ring carbon atoms in the aryl moiety and 1 to 6, in particular 1 to 4 carbon atoms in the alkyl moiety. Arylalkyl may be substituted by one or more identical or different radicals in the alkyl and/or aryl moiety. Examples of such arylalkyls include benzyl and 1-phenylethyl. The arylalkyl groups according to the invention may optionally be substituted by one or more identical or different radicals $M^1$.

According to the invention, "heterocycle", "heterocyclic ring" or "heterocyclic ring system" represents a carbocyclic ring system having at least one ring in which at least one carbon atom is replaced by a heteroatom, preferably by a heteroatom from the group consisting of N, O, S, P, B, Si, Se, and which is saturated, unsaturated or heteroaromatic and may be unsubstituted or substituted by a substituent Z, where the point of attachment is located at a ring atom. Unless defined differently, the heterocyclic ring contains preferably 3 to 9 ring atoms, especially 3 to 6 ring atoms, and one or more, preferably 1 to 4, especially 1, 2 or 3, heteroatoms in the heterocyclic ring, preferably from the group consisting of N, O, and S, although no two oxygen atoms should be directly adjacent. The heterocyclic rings usually contain not more than 4 nitrogen atoms and/or not more than 2 oxygen atoms and/or not more than 2 sulphur atoms. If the heterocyclyl radical or the heterocyclic ring is optionally substituted, it may be fused to other carbocyclic or heterocyclic rings. In the case of optionally substituted heterocyclyl, the invention also embraces polycyclic systems, for example 8-azabicyclo[3.2.1]octanyl or 1-azabicyclo[2.2.1]heptyl. In the case of optionally substituted heterocyclyl, the invention also embraces spirocyclic systems, for example 1-oxa-5-azaspiro[2.3]hexyl. The groups "heterocycle", "heterocyclic ring" or "heterocyclic ring system" according to the invention may optionally be substituted by one or more identical or different radicals $M^1$.

Heterocyclyl groups according to the invention are, for example, piperidinyl, piperazinyl, morpholinyl, thiomorpholinyl, dihydropyranyl, tetrahydropyranyl, dioxanyl, pyrrolinyl, pyrrolidinyl, imidazolinyl, imidazolidinyl, thiazolidinyl, oxazolidinyl, dioxolanyl, dioxolyl, pyrazolidinyl, tetrahydrofuranyl, dihydrofuranyl, oxetanyl, oxiranyl, azetidinyl, aziridinyl, oxazetidinyl, oxaziridinyl, oxazepanyl, oxazinanyl, azepanyl, oxopyrrolidinyl, dioxopyrrolidinyl, oxomorpholinyl, oxopiperazinyl and oxepanyl.

Heteroarylene, i.e. heteroaromatic systems, has a particular meaning. According to the invention, the expression "heteroaryl" represents heteroaromatic compounds, i.e. fully unsaturated aromatic heterocyclic compounds covered by the above definition of heterocycles, preferably 5- to 7-membered rings having 1 to 3, preferably 1 or 2, identical or different heteroatoms from the abovementioned group. Heteroaryls according to the invention are, for example, furyl, thienyl, pyrazolyl, imidazolyl, 1,2,3- and 1,2,4-triazolyl, isoxazolyl, thiazolyl, isothiazolyl, 1,2,3-, 1,3,4-, 1,2,4- and 1,2,5-oxadiazolyl, azepinyl, pyrrolyl, pyridyl, pyridazinyl, pyrimidinyl, pyrazinyl, 1,3,5-, 1,2,4- and 1,2,3-triazinyl, 1,2,4-, 1,3,2-, 1,3,6- and 1,2,6-oxazinyl, oxepinyl, thiepinyl, 1,2,4-triazolonyl and 1,2,4-diazepinyl. Furthermore, the heteroaryl groups according to the invention may optionally be substituted by one or more identical or different radicals $M^1$.

For the purpose of the present invention, "substituted" group or group "substituted by at least one radical $M^1$" such as an optionally substituted alkyl, alkenyl, alkynyl, cycloalkyl, aryl, phenyl, benzyl, heterocyclyl, heteroaryl or amino radical, etc., is generally a group containing at least one hydrocarbon-containing or nitrogen-hydrogen-containing fraction where the hydrogen is replaced by a different atom or an atom group $M^1$. The term "substituted groups" also includes "halogenated" groups which may be optionally substituted by one or more $M^1$, as long as at least one substituent is a halogen. A substituted group is derived from the unsubstituted base structure, wherein the base structure is substituted by one or more substituent(s) $M^1$, preferably 1, 2 or 3 radicals $M^1$, and the substituent(s) $M^1$ are in each case selected independently of one another from the group consisting of halogen, hydroxyl, nitro, formyl, carboxyl, cyano, amino, isocyano, azido, $(C_1-C_4)$-alkyl, $(C_1-C_4)$-haloalkyl, $(C_2-C_4)$-alkenyl, $(C_2-C_4)$-alkynyl, $(C_3-C_6)$-cycloalkyl $(C_1-C_4)$-alkoxy, $(C_1-C_4)$-halogalkoxy, $(C_1-C_4)$-alkoxy-$(C_1-C_4)$-alkoxy, $(C_1-C_4)$-alkoxy-$(C_1-C_6)$-alkyl, N—$(C_1-C_4)$-alkoxyimino-$(C_1-C_3)$-alkyl, $(C_1-C_4)$-alkylsulfanyl, $(C_1-C_4)$-haloalkylsulfanyl, $(C_1-C_4)$-alkoxycarbonyl, $(C_1-C_4)$-alkylcarbonyl, carbamoyl, $C_1-C_4$-alkylcarbamoyl, $C_3-C_7$-cycloalkylcarbamoyl, mono- and N,N-di($C_1-C_4$)-alkylaminocarbonyl, amino, $(C_1-C_6)$-acylamino, mono- and N,N-di($C_1-C_4$)-alkylamino, tri($C_1-C_4$)-alkylsilyl, $(C_3-C_6)$-cycloalkyl, $C_6$-aryl, heterocyclyl having 3 to 6 ring atoms, wherein any of the latter cyclic groups may also be attached via heteroatoms or a divalent functional $CH_2$, or $C_2H_4$ group, $(C_1-C_4)$-alkylsulfinyl, where both enantiomers of the $(C_1-C_4)$-alkylsulfinyl group are included, $(C_1-C_4)$-alkylsulfonyl, $(C_1-C_4)$-alkylphosphinyl, $(C_1-C_4)$—$(C_1-C_4)$-alkylsulfanyl-$(C_1-C_4)$-alkyl, $(C_1-C_4)$-alkoxy-$(C_1-C_4)$-alkyl, mono- and N,N-di($C_1-C_4$)-alkylamino($C_1-C_4$)-alkyl and hydroxy $(C_1-C_4)$-alkyl. The radicals $M^1$ mentioned in an exemplary manner can be unsubstituted or optionally (e.g. alkyl or amino), if they contain hydrocarbon-containing or nitrogen-hydrogen-containing fractions, substituted by one or more, preferably 1, 2 or 3 radicals $M^2$, where $M^2$ independently of the others is selected from the group consisting of amino, hydroxy, halogen, nitro, cyano, isocyano, mercapto, isothiocyanato, carboxy and carboxamide. Substituted groups also include substituted groups explicitly mentioned. "Haloalkyl" is embraced, for example, by the expression "substituted" alkyl and represents a preferred embodiment of a substituted alkyl. This applies analogously to all other substituted groups.

If two or more radicals form one or more rings, these may be carbocyclic, heterocyclic, saturated, partially saturated, unsaturated, for example also aromatic and further-substituted.

Optionally substituted phenyl is preferably phenyl which is unsubstituted or is mono- or polysubstituted, preferably mono-, di- or trisubstituted by identical or different radicals selected from the group of halogen, cyano, isocyano, nitro, or $(C_1-C_4)$-alkyl, $C_2-C_4$-alkenyl, $C_2-C_4$-alkynyl, $(C_1-C_4)$-alkoxy, $(C_1-C_4)$-alkoxy-$(C_1-C_4)$alkoxy, $(C_1-C_4)$-alkoxy-$(C_1-C_4)$-alkyl, $(C_3-C_6)$-cycloalkyl, $(C_1-C_4)$-haloalkyl, $(C_1-C_4)$-haloalkoxy, $(C_1-C_4)$-alkylsulfanyl, $(C_1-C_4)$-haloalkylsulfanyl optionally substituted by at least one radical $M^1$, e.g. o-, m- and p-tolyl, dimethylphenyl, 2-, 3- and 4-chlorophenyl, 2-, 3- and 4-fluorophenyl, 2-, 3- and 4-trifluoromethyl- and -trichloromethylphenyl, 2,4-, 3,5-, 2,5- and 2,3-dichlorophenyl, o-, m- and p-methoxyphenyl.

Optionally substituted cycloalkyl is preferably cycloalkyl, which is unsubstituted or mono- or polysubstituted, preferably up to trisubstituted, by identical or different radicals selected from the group consisting of halogen, haloalkyl, cyano, $(C_1-C_4)$-alkyl, $(C_1-C_4)$-alkoxy, $(C_1-C_4)$-alkoxy-$(C_1-C_4)$-alkoxy, $(C_1-C_4)$-alkoxy-$(C_1-C_4)$-alkyl, $(C_1-C_4)$-haloalkyl and $(C_1-C_4)$-haloalkoxy.

Optionally substituted heterocyclyl is preferably heterocyclyl which is unsubstituted or mono- or polysubstituted, preferably up to trisubstituted, by identical or different radicals from the group of halogen, cyano, $(C_1-C_4)$-alkyl, $(C_1-C_4)$-alkoxy, $(C_1-C_4)$-alkoxy-$(C_1-C_4)$-alkoxy, $(C_1-C_4)$-alkoxy-$(C_1-C_4)$-alkyl, $(C_1-C_4)$-haloalkyl, $(C_1-C_4)$-haloalkoxy, nitro and oxo, especially mono- or polysubstituted by radicals from the group of halogen, $(C_1-C_4)$-alkyl, $(C_1-C_4)$-alkoxy, $(C_1-C_4)$-haloalkyl and oxo, most preferably substituted by one or two $(C_1-C_4)$-alkyl radicals.

Examples of alkyl-substituted heteroaryls are furylmethyl, thienylmethyl, pyrazolylmethyl, imidazolylmethyl, 1,2,3- and 1,2,4-triazolylmethyl, isoxazolylmethyl, thiazolylmethyl, isothiazolylmethyl, 1,2,3-, 1,3,4-, 1,2,4- and 1,2,5-oxadiazolylmethyl, azepinylmethyl, pyrrolylmethyl, pyridylmethyl, pyridazinylmethyl, pyrimidinylmethyl, pyrazinylmethyl, 1,3,5-, 1,2,4- and 1,2,3-triazinylmethyl, 1,2,4-, 1,3,2-, 1,3,6- and 1,2,6-oxazinylmethyl, oxepinylmethyl, thiepinylmethyl and 1,2,4-diazepinylmethyl.

Not included are such combinations which contravene the laws of nature and which the person skilled in the art would therefore rule out on the basis of his/her expert knowledge. Ring structures having three or more adjacent oxygen atoms, for example, are excluded.

DETAILED DESCRIPTION

The inventive pyrazolyl derivatives are defined by the general formula (I)

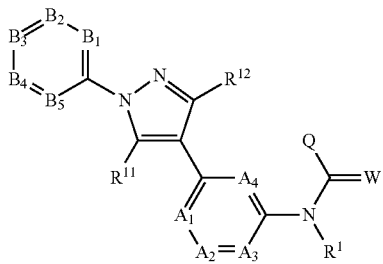

defined in which
$R^1$ is hydrogen, optionally substituted $C_1$-$C_6$-alkyl, $C_3$-$C_6$-alkenyl, $C_3$-$C_6$-alkynyl, $C_3$-$C_7$-cycloalkyl, $C_1$-$C_6$-alkylcarbonyl, $C_1$-$C_6$-alkoxycarbonyl, aryl($C_1$-$C_3$)-alkyl, heteroaryl($C_1$-$C_3$)-alkyl;
the chemical moieties
$A_1$ represents $CR^2$ or nitrogen (N),
$A_2$ represents $CR^3$ or N,
$A_3$ represents $CR^4$ or N,
$A_4$ represents $CR^5$ or N,
$B_1$ represents $CR^6$ or N,
$B_2$ represents $CR^7$ or N,
$B_3$ represents $CR^8$ or N,
$B_4$ represents $CR^9$ or N, and
$B_5$ represents $CR^{10}$ or N;
but not more than three of the chemical moieties $A_1$ to $A_4$ simultaneously represent nitrogen and not more than three of the moieties $B_1$ to $B_5$ simultaneously represent nitrogen;
$R^2$, $R^3$, $R^4$, $R^5$, $R^6$, $R^7$, $R^9$ and $R^{10}$ independently of one another represent hydrogen, halogen, cyano, nitro, optionally substituted $C_1$-$C_6$-alkyl, $C_3$-$C_7$-cycloalkyl, $C_1$-$C_6$-alkoxy, N—($C_1$-$C_6$-alkoxy)imino-$C_1$-$C_3$-alkyl, $C_1$-$C_6$-alkylsulfanyl, $C_1$-$C_6$-alkylsulfinyl, $C_1$-$C_6$-alkylsulfonyl, N—($C_1$-$C_6$-alkyl)amino or N,N-di($C_1$-$C_6$-alkyl)amino, $C_1$-$C_6$-alkylsulfonylamino N—($C_1$-$C_6$-alkyl)-$C_1$-$C_6$-alkylsulfonylamino;
$R^8$ represents halogen, cyano, nitro, in each case optionally substituted $C_1$-$C_6$-alkyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulfanyl, $C_1$-$C_6$-alkylsulphinyl, $C_1$-$C_6$-alkylsulfonyl, N—$C_1$-$C_6$-alkylamino or N,N-di-$C_1$-$C_6$-alkylamino, preferably halogen, cyano, nitro or $C_1$-$C_6$-haloalkyl;
$R^{11}$ and $R^{12}$ independently of one another represents hydrogen, halogen, cyano, nitro, amino or optionally halogensubstituted $C_1$-$C_6$-alkyl, $C_1$-$C_6$-alkyloxy, $C_1$-$C_6$-alkylcarbonyl, $C_1$-$C_6$-alkylsulfanyl, $C_1$-$C_6$-alkylsulphinyl, $C_1$-$C_6$-alkylsulfonyl;
W is oxygen or sulfur;
Q is hydrogen, amino, or moieties $C_1$-$C_6$-alkyl, $C_2$-$C_6$-alkenyl, $C_2$-$C_6$-alkynyl, $C_3$-$C_6$-cycloalkyl, $C_2$-$C_5$-heterocyclyl, $C_1$-$C_4$-alkoxy, $C_1$-$C_6$-alkyl-$C_3$-$C_6$-cycloalkyl, $C_3$-$C_6$-cycloalkyl-$C_1$-$C_6$-alkyl, aryl-($C_1$-$C_3$)-alkyl, heteroaryl-($C_1$-$C_3$)-alkyl, $C_1$-$C_4$-alkoxycarbonyl, optionally monosubstituted to heptasubstituted independently of one another by halogen, cyano, alkoxy and alkoxycarbonyl, or for a moiety N—$C_1$-$C_4$-alkylamino, N—$C_1$-$C_4$-alkylcarbonylamino, N,N-di-$C_1$-$C_4$-alkylamino and $C_1$-$C_4$-alkylsulfonylamino; or
Q is an aryl substituted by 0, 1, 2, 3 or 4 V substituents or a 5- or 6-membered heteroaryl substituted by 0, 1, 2, 3 or 4 V substituents, where
V is independently of one another halogen, cyano, nitro, or $C_1$-$C_6$-alkyl, $C_2$-$C_4$-alkenyl, $C_2$-$C_4$-alkynyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulfanyl, $C_1$-$C_6$-alkylsulfinyl, $C_1$-$C_6$-alkylsulfonyl, N,N-di-($C_1$-$C_6$-alkyl)amino optionally mono- to heptasubstituted independently of one another by halogen, cyano, alkoxy and alkoxycarbonyl;
and salts, N-oxides and tautomeric forms of the compound of the formula (I).
B
A preferred embodiment refers to compounds of the formula (I), in which $B_1$ is $CR^6$, $B_2$ is $CR^7$, $B_3$ is $CR^8$, $B_4$ is $CR^9$ and $B_5$ is $CR^{10}$.

Formula (I), in which a further preferred embodiment refers to compounds of the formula (I), in which $B_1$ is $CR^6$, $B_2$ is $CR^7$, $B_3$ is $CR^8$, $B_4$ is $CR^9$ and $B_5$ is $CR^{10}$ and $R^8$ is halogen or halogenated $C_1$-$C_6$-alkyl, preferably halogenated $C_1$-$C_6$-alkyl, more preferably perhalogenated $C_1$-$C_6$-alkyl, still more preferably perfluorinated $C_1$-$C_6$-alkyl such as $CF_3$, $C_2F_5$, $C_3F_7$, $C_4F_9$.

A further preferred embodiment refers to compounds of the formula (I), in which $B_1$ is $CR^6$, $B_2$ is $CR^7$, $B_3$ is $CR^8$, $B_4$ is $CR^9$ and $B_5$ is $CR^{10}$ and $R^7$ and $R^9$ are each independently of one another hydrogen or optionally substituted $C_1$-$C_6$-alkyl, preferably hydrogen.

A further preferred embodiment refers to compounds of the formula (I), in which $B_1$ is $CR^6$, $B_2$ is $CR^7$, $B_3$ is $CR^8$, $B_4$ is $CR^9$ and $B_5$ is $CR^{10}$ and $R^6$ and $R^{10}$ are each independently of one another hydrogen, halogen, cyano, optionally substituted $C_1$-$C_6$-alkyl, optionally substituted $C_1$-$C_6$-alkoxy, more preferably halogen or optionally halogenated $C_1$-$C_6$-alkyl or optionally halogenated $C_1$-$C_6$-alkoxy, still more preferably F, Cl, I, Br, $C_1$-$C_3$-alkyl or perhalogenated $C_1$-$C_3$-alkyl, especially preferably Cl, Br, $C_1$-$C_3$-alkyl such as $CH_3$, or perfluorinated $C_1$-$C_3$-alkyl such as $CF_3$, or $C_1$-$C_3$-alkoxy such as —O—$CH_3$, or perfluorinated $C_1$-$C_3$-alkoxy such as —O—$CF_3$. A still more preferred embodiment refers to compounds of the formula (I), in which $B_1$ is $CR^6$, $B_2$ is $CR^7$, $B_3$ is $CR^8$, $B_4$ is $CR^9$ and $B_5$ is $CR^{1'}$ and $R^6$ and $R^{10}$ are each independently of one another hydrogen, halogen, cyano, optionally substituted $C_1$-$C_6$-alkyl, more preferably halogen or optionally halogenated $C_1$-$C_6$-alkyl, still more preferably F, Cl, I, Br, $C_1$-$C_3$-alkyl or perhalogenated $C_1$-$C_3$-alkyl, especially preferably Cl, Br, $C_1$-$C_3$-alkyl such as $CH_3$ or perfluorinated $C_1$-$C_3$-alkyl such as $CF_3$.

A further preferred embodiment refers to compounds of the formula (I), in which $B_1$ is $CR^6$, $B_2$ is $CR^7$, $B_3$ is $CR^8$, $B_4$ is $CR^9$ and $B_5$ is $CR^{10}$ and $R^6$, $R^7$, $R^8$, $R^9$ and $R^{10}$ are as defined above, preferably wherein $R^8$ is perfluorinated $C_1$-$C_6$-alkyl such as $CF_3$, $C_2F_5$, $C_3F_7$, $C_4F_9$, $R^7$ and $R^9$ are in each case hydrogen, $R^6$ and $R^{10}$ are each independently of one another Cl, Br, $C_1$-$C_3$-alkyl such as $CH_3$ or perfluorinated $C_1$-$C_3$-alkyl such as $CF_3$ or $C_1$-$C_3$-alkoxy such as —O—$CH_3$, or perfluorinated $C_1$-$C_3$-alkoxy such as —O—$CF_3$.

A further preferred embodiment refers to compounds of the formula (I), in which $B_1$ is $CR^6$, $B_2$ is $CR^7$, $B_3$ is $CR^8$, $B_4$ is $CR^9$ and $B_5$ is $CR^{10}$ and $R^6$, $R^7$, $R^8$, $R^9$ and $R^{10}$ are as defined above, preferably wherein $R^8$ is perfluorinated $C_1$-$C_6$-alkyl such as $CF_3$, $C_2F_5$, $C_3F_7$, $C_4F_9$, $R^7$ and $R^9$ are in each case hydrogen, $R^6$ is Cl, Br, $C_1$-$C_3$-alkyl such as $CH_3$ and $R^{10}$ is Cl, $C_1$-$C_3$-alkyl such as $CH_3$ or perfluorinated $C_1$-$C_3$-alkyl such as $CF_3$.

$R^{11}R^{12}$

A further preferred embodiment refers to compounds of the formula (I), in which $R^{11}$ and $R^{12}$ are each independently of one another hydrogen, halogen, cyano, nitro, amino, or a $C_1$-$C_6$-alkyl optionally substituted by halogen, more preferably hydrogen, halogen, or a $C_1$-$C_6$-alkyl optionally substituted by halogen, even more preferably hydrogen or $C_1$-$C_3$-alkyl, especially preferably hydrogen.

A further preferred embodiment refers to compounds of the formula (I), in which $B_1$ is $CR^6$, $B_2$ is $CR^7$, $B_3$ is $CR^8$, $B_4$ is $CR^9$ and $B_5$ is $CR^{10}$ and $R^6$, $R^7$, $R^8$, $R^9$ and $R^{10}$ are as defined above, and $R^{11}$ and $R^{12}$ are as defined above.

A further preferred embodiment refers to compounds of the formula (I), in which $B_1$ is $CR^6$, $B_2$ is $CR^7$, $B_3$ is $CR^8$, $B_4$ is $CR^9$ and $B_5$ is $CR^{10}$ and $R^6$, $R^7$, $R^8$, $R^9$ and $R^{10}$ are as defined above, and $R^{11}$ and $R^{12}$ are in each case hydrogen.

W

A further preferred embodiment relates to compounds of the formula (I) in which W represents oxygen.

A further preferred embodiment refers to compounds of the formula (I), in which W is oxygen, in which $B_1$ is $CR^6$, $B_2$ is $CR^7$, $B_3$ is $CR^8$, $B_4$ is $CR_9$ and $B_5$ is $CR^{10}$ and $R^6$, $R^7$, $R^8$, $R^9$ and $R^{10}$ are as defined above, and $R^{11}$ and $R^{12}$ are as defined above.

A

A further preferred embodiment relates to compounds of the formula (I), in which $A_1$ is $CR^2$, $A_2$ is $CR^3$ or N, $A_3$ is $CR^4$ or N and $A_4$ is $CR^5$.

A further preferred embodiment relates to compounds of the formula (I), in which $A_1$ is $CR^2$, $A_2$ is $CR^3$ or N, $A_3$ is $CR^4$ or N and $A_4$ is $CR^5$ and $R^2$ is hydrogen, or optionally substituted $C_1$-$C_6$-alkyl steht, preferably hydrogen or $C_1$-$C_6$-alkyl, particularly preferably hydrogen.

A further preferred embodiment refers to compounds of the formula (I), in which $A_1$ is $CR^2$, $A_2$ is $CR^3$ or N, $A_3$ is $CR^4$ or N and $A_4$ is $CR^5$ and $R^2$ is hydrogen, or optionally substituted $C_1$-$C_6$-alkyl, preferably hydrogen or $C_1$-$C_6$-alkyl, particularly preferably hydrogen and $R^3$, $R^4$ and $R^5$ are each independently of one another hydrogen, halogen, CN, optionally substituted $C_1$-$C_6$-alkyl, optionally substituted $C_1$-$C_6$-alkoxy or optionally substituted N,N-di-$C_1$-$C_6$-alkylamino, more preferably hydrogen, halogen such as Cl or F, $C_1$-$C_6$-alkyl such as $C_1$-$C_3$-alkyl (e.g. $CH_3$), halogenated $C_1$-$C_6$-alkyl such as halogenated $C_1$-$C_3$-alkyl (e.g. —$CF_3$) or N,N-di-$C_1$-$C_6$-alkylamino such as N,N-di-$C_1$-$C_3$-alkylamino (e.g. N,N-dimethylamino).

A further preferred embodiment refers to compounds of the formula (I), in which W is oxygen, in which $B_1$ is $CR^6$, $B_2$ is $CR^7$, $B_3$ is $CR^8$, $B_4$ is $CR^9$ and $B_5$ is $CR^{10}$ and $R^6$, $R^7$, $R^8$, $R^9$ and $R^{10}$ are as defined above, and $R^{11}$ and $R^{12}$ are as defined above, $A_1$ is $CR^2$, $A_2$ is $CR^3$ or N, $A_3$ is $CR^4$ or N and $A_4$ is $CR^5$ where $R^2$, $R^3$, $R^4$ and $R^5$ are as defined above.

Q

A further preferred embodiment refers to compounds of the formula (I), in which Q is hydrogen, optionally substituted $C_1$-$C_6$-alkyl, optionally substituted $C_3$-$C_6$-cycloalkyl, optionally substituted $C_2$-$C_5$-heterocyclyl, optionally substituted $C_1$-$C_6$-alkyl-$C_3$-$C_6$-cycloalkyl, optionally substituted aryl-($C_1$-$C_3$)-alkyl, optionally substituted heteroaryl-($C_1$-$C_3$)-alkyl, an aryl substituted by 0, 1, 2, 3 or 4 V substituents or a 5- or 6-membered heteroaryl substituted by 0, 1, 2, 3 or 4 V substituents.

A further preferred embodiment relates to compounds of the formula (I), in which Q is hydrogen, $C_1$-$C_6$-alkyl optionally substituted by one, two or three substituents selected from the group consisting of oxo, cyano, nitro, amino; halogenated $C_1$-$C_6$-alkyl; $C_3$-$C_6$-cycloalkyl optionally substituted by one, two or three substituents selected from the group consisting of halogen, cyano, nitro, $C_1$-$C_3$-alkyl and amino; $C_2$-$C_5$-heterocyclyl optionally substituted by one, two or three substituents selected from the group consisting of halogen, cyano, nitro, $C_1$-$C_3$-alkyl and amino; aryl-($C_1$-$C_3$)-alkyl optionally substituted by one, two or three substituents selected from the group consisting of halogen, cyano, nitro, amino; heteroaryl-($C_1$-$C_3$)-alkyl optionally substituted by one, two or three substituents selected from the group consisting of halogen, cyano, nitro, amino; an aryl substituted by 0, 1, 2, 3 or 4 V substituents or a 5- or 6-membered heteroaryl substituted by 0, 1, 2, 3 or 4 V substituents, where V is independently of one another halogen, cyano; $C_1$-$C_6$-alkyl optionally mono- to trisubstituted independently of one another by cyano, alkoxy and alkoxycarbonyl; halogenated $C_1$-$C_6$-alkyl; $C_1$-$C_6$-alkoxy optionally mono- to trisubstituted independently of one another by cyano, alkoxy and alkoxycarbonyl; halogenated $C_1$-$C_6$-alkoxy.

A further preferred embodiment relates to compounds of the formula (I), in which Q is $C_1$-$C_6$-alkyl optionally substituted by one, two or three substituents selected from the group consisting of oxo, cyano, nitro, amino; halogenated $C_1$-$C_6$-alkyl; $C_3$-$C_6$-cycloalkyl optionally substituted by one, two or three substituents selected from the group consisting of halogen, cyano, nitro, $C_1$-$C_3$-alkyl and amino; $C_2$-$C_5$-heterocyclyl optionally substituted by one, two or three substituents selected from the group consisting of halogen, cyano, nitro, $C_1$-$C_3$-alkyl and amino; an aryl substituted by 0, 1, 2, 3 or 4 V substituents or a 5- or 6-membered heteroaryl substituted by 0, 1, 2, 3 or 4 V substituents, where V is independently of one another halogen, cyano; $C_1$-$C_6$-alkyl; halogenated $C_1$-$C_6$-alkyl; $C_1$-$C_6$-alkoxy; halogenated $C_1$-$C_6$-alkoxy.

A further preferred embodiment relates to compounds of the formula (I), in which Q is $C_3$-$C_6$-cycloalkyl optionally substituted by one, two or three substituents selected from the group consisting of halogen, cyano, nitro, $C_1$-$C_3$-alkyl and amino; $C_2$-$C_5$-heterocyclyl optionally substituted by one, two or three substituents selected from the group consisting of halogen, cyano, nitro, $C_1$-$C_3$-alkyl and amino; an aryl substituted by 0, 1, 2, 3 or 4 V substituents or a 5- or 6-membered heteroaryl substituted by 0, 1, 2, 3 or 4 V substituents, where V is independently of one another halogen, cyano; $C_1$-$C_6$-alkyl; halogenated $C_1$-$C_6$-alkyl; $C_1$-$C_6$-alkoxy; halogenated $C_1$-$C_6$-alkoxy.

A further preferred embodiment relates to compounds of the formula (I), in which Q is $C_3$-$C_6$-cycloalkyl optionally substituted by one substituent selected from the group consisting of halogen, $C_1$-$C_3$-alkyl and cyano (such as, for example, cyclopropyl optionally substituted by cyano or $C_1$-$C_3$-alkyl); $C_2$-$C_5$-heterocyclyl optionally substituted by one substituent selected from the group consisting of halogen or cyano, such as, for example, thietanyl (thiacyclobutanyl) optionally substituted by cyano or $C_1$-$C_3$-alkyl; an aryl substituted by 0, 1 or 2 V substituents or a 5- or 6-membered heteroaryl substituted by 0, 1, 2, 3 or 4 V substituents, wherein V is each independently of one another halogen (e.g. F, Cl), cyano; $C_1$-$C_6$-alkyl; $C_1$-$C_6$-alkoxy (such as phenyl optionally substituted by 0, 1 or 2 V substituents each selected independently of one another from the group consisting of halogen (such as F, Cl), $C_1$-$C_3$-alkoxy (such as methoxy and ethoxy), $C_1$-$C_3$-alkyl (such as methyl), halogenated $C_1$-$C_3$-alkyl (such as $CF_3$) and cyano; or pyridyl, pyrimidinyl and thiophenyl optionally substituted by 0, 1 or 2 V substituents each selected independently of one another from the group consisting of halogen (such as F, Cl), $C_1$-$C_3$-alkyl (such as methyl) halogenated $C_1$-$C_3$-alkyl (such as $CF_3$) and cyano); or pyridyl, pyrimidinyl, thienyl, oxazolyl or thiophenyl optionally substituted by 0, 1 or 2 V substituents each selected independently of one another from the group consisting of halogen (such as F, Cl), $C_1$-$C_3$-alkyl (such as methyl), halogenated $C_1$-$C_3$-alkyl (such as $CF_3$) and cyano.

A further preferred embodiment refers to compounds of the formula (I), in which W is oxygen, in which $B_1$ is $CR^6$, $B_2$ is $CR^7$, $B_3$ is $CR^8$, $B_4$ is $CR^9$ and $B_5$ is $CR^{10}$ and $R^6$, $R^7$, $R^8$, $R^9$ and $R^{10}$ are as defined above, and $R^{11}$ and $R^{12}$ are as defined above, $A_1$ is $CR^2$, $A_2$ is $CR^3$ or N, $A_3$ is $CR^4$ or N and $A_4$ is $CR^5$ where $R^2$, $R^3$, $R^4$ and $R^5$ are as defined above and Q is as defined above.

A further preferred embodiment refers to compounds of the formula (I), in which W is oxygen, in which $B_1$ is $CR^6$, $B_2$ is $CR^7$, $B_3$ is $CR^8$, $B_4$ is $CR^9$ and $B_5$ is $CR^{10}$ and $R^6$, $R^7$, $R^8$, $R^9$ and $R^{10}$ are as defined above, and $R^{11}$ and $R^{12}$ are as defined above, $A_1$ is $CR^2$, $A_2$ is $CR^3$ or N, $A_3$ is $CR^4$ or N and $A_4$ is $CR^5$ where $R^2$, $R^3$, $R^4$ and $R^5$ are as defined above and Q is as defined above.

$R^1$

A further preferred embodiment relates to compounds of the formula (I), in which $R^1$ is hydrogen, $C_1$-$C_3$-alkyl or $C_3$-$C_6$-cycloalkyl.

A further preferred embodiment relates to compounds of the formula (I) in which $R^1$ is hydrogen.

A further preferred embodiment refers to compounds of the formula (I), in which W is oxygen, in which $B_1$ is $CR^6$, $B_2$ is $CR^7$, $B_3$ is $CR^8$, $B_4$ is $CR^9$ and $B_5$ is $CR^{10}$ and $R^6$, $R^7$, $R^8$, $R^9$ and $R^{10}$ are as defined above, and $R^{11}$ and $R^{12}$ are as defined above, $A_1$ is $CR^2$, $A_2$ is $CR^3$ or N, $A_3$ is $CR^4$ or N and $A_4$ is $CR^5$ where $R^2$, $R^3$, $R^4$ and $R^5$ are as defined above and Q is as defined above and $R^1$ is hydrogen, $C_1$-$C_3$-alkyl or $C_3$-$C_6$-cycloalkyl.

A further preferred embodiment refers to compounds of the formula (I), in which W is oxygen, in which $B_1$ is $CR^6$, $B_2$ is $CR^7$, $B_3$ is $CR^8$, $B_4$ is $CR^9$ and $B_5$ is $CR^{10}$ and $R^6$, $R^7$, $R^8$, $R^9$ and $R^{10}$ are as defined above, and $R^{11}$ and $R^{12}$ are as defined above, $A_1$ is $CR^2$, $A_2$ is $CR^3$ or N, $A_3$ is $CR^4$ or N and $A_4$ is $CR^5$ where $R^2$, $R^3$, $R^4$ and $R^5$ are as defined above and Q is as defined above and $R^1$ is hydrogen.

A further preferred embodiment refers to compounds of the formula (I), in which W is oxygen, in which $B_1$ is $CR^6$, $B_2$ is $CR^7$, $B_3$ is $CR^8$, $B_4$ is $CR^9$ and $B_5$ is $CR^{10}$ and $R^6$, $R^7$, $R^8$, $R^9$ and $R^{10}$ are as defined above, and $R^{11}$ and $R^{12}$ are as defined above, $A_1$ is $CR^2$, $A_2$ is $CR^3$ or N, $A_3$ is $CR^4$ or N and $A_4$ is $CR^5$ where $R^2$, $R^3$, $R^4$ and $R^5$ are as defined above and Q is as defined above and $R^1$ is hydrogen.

Embodiments furthermore preferred relate to compounds of the formula (I')

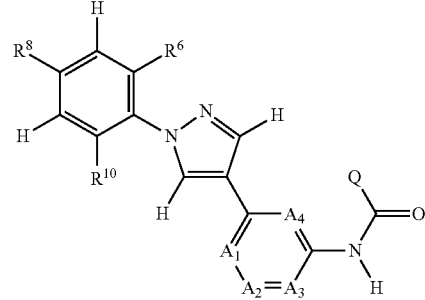

(I')

where $A_1$, $A_2$, $A_3$, $A_4$, $R^6$, $R^8$, $R^{10}$ and Q are defined as described in this application, preferably where
$A_1$ is $CR^2$,
$A_2$ is $CR^3$ or N,
$A_3$ is $CR^4$ or N,
$A_4$ is $CR^5$,
$R^2$ represents hydrogen,
$R^3$ is hydrogen or $C_1$-$C_3$-alkyl, particularly preferably hydrogen,
$R^4$ is hydrogen, halogen, CN or optionally substituted $C_1$-$C_6$-alkyl or —N($C_1$-$C_3$-alkyl)$_2$, particularly preferably hydrogen, Cl, F, or $C_1$-$C_3$-alkyl (such as $CH_3$) or —N($C_1$-$C_3$-alkyl)$_2$ (such as —N($CH_3$)$_2$),
$R^5$ is hydrogen or halogen, particularly preferably hydrogen or F,
$R^6$ is hydrogen, halogen, cyano, optionally substituted $C_1$-$C_6$-alkyl, more preferably halogen or optionally halogenated $C_1$-$C_6$-alkyl, still more preferably F, Cl, I, Br, $C_1$-$C_3$-alkyl (such as methyl) or perhalogenated $C_1$-$C_3$-alkyl, particularly preferably Cl, Br or $C_1$-$C_3$-alkyl (such as $CH_3$),
$R^8$ is halogen or $C_1$-$C_6$-haloalkyl, preferably $C_1$-$C_6$-haloalkyl, more preferably perhalogenated $C_1$-$C_6$-alkyl, still more preferably perfluorinated $C_1$-$C_6$-alkyl such as perfluorinated $C_1$-$C_4$-alkyl: $CF_3$, $C_2F_5$, $C_3F_7$, $C_4F_9$,
$R^{10}$ is hydrogen, halogen, cyano, optionally substituted $C_1$-$C_6$-alkyl, more preferably halogen or optionally halogenated $C_1$-$C_6$-alkyl or optionally halogenated $C_1$-$C_6$-alkoxy (such as $OCF_3$ or $OCHF_2$), still more preferably F, Cl, Br, $C_1$-$C_3$-alkyl (such as methyl, ethyl) or perhalogenated $C_1$-$C_3$-alkyl, particularly preferably Cl, $C_1$-$C_3$-alkyl (such as methyl, ethyl) or perfluorinated $C_1$-$C_3$-alkyl (such as $CF_3$), and
Q is $C_3$-$C_6$-cycloalkyl optionally substituted by one substituent selected from the group consisting of halogen, $C_1$-$C_3$-alkyl and cyano (such as, for example, cyclopropyl optionally substituted by cyano or $C_1$-$C_3$-alkyl); $C_2$-$C_5$-heterocyclyl optionally substituted by one substituent selected from the group consisting of halogen or cyano, such as, for example, thietanyl (thiacyclobutanyl) optionally substituted by cyano or $C_1$-$C_3$-alkyl; an aryl substituted by 0, 1 or 2 V substituents or a 5- or 6-membered heteroaryl substituted by 0, 1, 2, 3 or 4 V substituents, wherein V is each independently of one another halogen (e.g. F, Cl), cyano; optionally halogenated $C_1$-$C_6$-alkyl; optionally halogenated $C_1$-$C_6$-alkoxy (such as phenyl optionally substituted by 0, 1 or 2 V substituents each selected independently of one another from the group consisting of halogen (such as F, Cl), $C_1$-$C_3$-alkoxy (such as methoxy and ethoxy), $C_1$-$C_3$-alkyl (such as methyl), halogenated $C_1$-$C_3$-alkyl (such as $CF_3$) and cyano; or pyridyl, pyrimidinyl or thiophenyl optionally substituted by 0, 1 or 2 V substituents each selected independently of one another from the group consisting of halogen (such as F, Cl), $C_1$-$C_3$-alkyl (such as methyl) halogenated $C_1$-$C_3$-alkyl (such as $CF_3$) and cyano); or pyridyl, pyrimidinyl, thienyl, oxazolyl or thiophenyl optionally substituted by 0, 1 or 2 V substituents each selected independently of one another from the group consisting of halogen (such as F, Cl), $C_1$-$C_3$-alkyl (such as methyl), halogenated $C_1$-$C_3$-alkyl (such as $CF_3$) and cyano.

Embodiments furthermore preferred relate to compounds of the formula (I') where $A_1$ represents $CR^2$, where $R^2$ represents hydrogen,
$A_2$ represents $CR^3$ or N, where $R^3$ represents hydrogen,
$A_3$ represents $CR^4$ or N, where $R^4$ is hydrogen, Cl, F, or $C_1$-$C_3$-alkyl (such as $CH_3$) or —N($C_1$-$C_3$-alkyl)$_2$ (such as —N($CH_3$)$_2$),
$A_4$ represents $CR^5$, where $R^5$ represents hydrogen or F,
$R^6$ represents Cl, Br or $C_1$-$C_3$-alkyl (such as $CH_3$),
$R^8$ represents perhalogeniertes $C_1$-$C_6$-alkyl, more preferably perfluorinated $C_1$-$C_4$-alkyl such as $CF_3$, $C_2F_5$, $C_3F_7$, $C_4F_9$,
$R^{10}$ represents Cl, $C_1$-$C_3$-alkyl (such as methyl) or perfluorinated $C_1$-$C_3$-alkyl (such as $CF_3$), and
Q represents (a) $C_3$-$C_6$-cycloalkyl optionally substituted by one substituent selected from the group consisting of halogen, $C_1$-$C_3$-alkyl and cyano (such as, for example, cyclopropyl optionally substituted by cyano or $C_1$-$C_3$-alkyl), (b) $C_2$-$C_5$-heterocyclyl optionally substituted by one substituent selected from the group consisting of halogen or cyano, such as, for example, thietanyl (thiacyclobutanyl) optionally substituted by cyano or $C_1$-$C_3$-alkyl, (c) an aryl substituted by 0, 1 or 2 V substituents or a 5- or 6-membered heteroaryl substituted by 0, 1, 2, 3 or 4 V substituents, wherein V is each independently of one another halogen (e.g. F, Cl), cyano, optionally halogenated $C_1$-$C_6$-alkyl, optionally halogenated $C_1$-$C_6$-alkoxy (such as phenyl optionally substituted by 0, 1 or 2 V substituents each selected independently of one another from the group consisting of halogen (such as F, Cl), $C_1$-$C_3$-alkoxy (such as methoxy and ethoxy), $C_1$-$C_3$-alkyl (such as methyl), halogenated $C_1$-$C_3$-alkyl (such as $CF_3$) and cyano; or pyridyl, pyrimidinyl, thienyl, oxazolyl or thiophenyl optionally substituted by 0, 1 or 2 V substituents V each selected independently of one another from the group consisting of halogen (such as F, Cl), $C_1$-$C_3$-alkyl (such as methyl) halogenated $C_1$-$C_3$-alkyl (such as $CF_3$) and cyano).

Embodiments furthermore preferred relate to compounds of the formula (Ia)

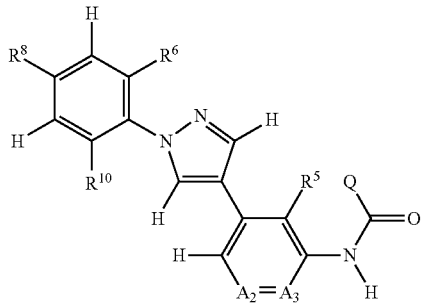

(Ia)

where $A_2$, $A_3$, $R^5$, $R^6$, $R^8$, $R^{10}$, $R^{10}$ and Q are defined as described in this application, preferably where $A_2$ is $CR^3$ or N,
$A_3$ is $CR^4$ or N,
$R^3$ is hydrogen or $C_1$-$C_3$-alkyl, particularly preferably hydrogen,
$R^4$ is hydrogen, halogen, CN or optionally substituted $C_1$-$C_6$-alkyl, particularly preferably hydrogen, Cl, F, or $C_1$-$C_3$-alkyl, or
$R^4$ is hydrogen, halogen, CN, optionally substituted $C_1$-$C_6$-alkyl or —N($C_1$-$C_3$-alkyl)$_2$, particularly preferably hydrogen, Cl, F, or $C_1$-$C_3$-alkyl (such as $CH_3$) or —N($C_1$-$C_3$-alkyl)$_2$ (such as —N($CH_3$)$_2$),
$R^5$ is hydrogen or halogen, particularly preferably hydrogen or F,
$R^6$ is hydrogen, halogen, cyano, optionally substituted $C_1$-$C_6$-alkyl, more preferably halogen or optionally halogenated $C_1$-$C_6$-alkyl, still more preferably F, Cl, I, Br, $C_1$-$C_3$-alkyl (such as methyl) or perhalogenated $C_1$-$C_3$-alkyl, particularly preferably Cl, Br or $C_1$-$C_3$-alkyl (such as $CH_3$),
$R^8$ is halogen or $C_1$-$C_6$-haloalkyl, preferably $C_1$-$C_6$-haloalkyl, more preferably perhalogenated $C_1$-$C_6$-alkyl, still more preferably perfluorinated $C_1$-$C_6$-alkyl such as $CF_3$, $C_2F_5$, $C_3F_7$, $C_4F_9$,
$R^{10}$ is hydrogen, halogen, cyano, optionally substituted $C_1$-$C_6$-alkyl, more preferably halogen or optionally halogenated $C_1$-$C_6$-alkyl or optionally halogenated $C_1$-$C_6$-alkoxy (such as $OCF_3$ or $OCHF_2$), still more preferably F, Cl, Br, $C_1$-$C_3$-alkyl (such as methyl, ethyl) or perhalogenated $C_1$-$C_3$-alkyl, particularly preferably Cl, $C_1$-$C_3$-alkyl (such as methyl, ethyl) or perfluorinated $C_1$-$C_3$-alkyl (such as $CF_3$), and
Q represents $C_3$-$C_6$-cycloalkyl optionally substituted by one substituent selected from the group consisting of halogen, $C_1$-$C_3$-alkyl and cyano (such as, for example, cyclopropyl optionally substituted by cyano or $C_1$-$C_3$-alkyl); $C_2$-$C_5$-heterocyclyl optionally substituted by one substituent selected from the group consisting of halogen or cyano, such as, for example, thietanyl (thiacyclobutanyl) optionally substituted by cyano or $C_1$-$C_3$-alkyl; an aryl substituted by 0, 1 or 2 V substituents or a 5- or 6-membered heteroaryl substituted by 0, 1, 2, 3 or 4 V substituents, wherein V is each independently of one another halogen (e.g. F, Cl), cyano, optionally halogenated $C_1$-$C_6$-alkyl, optionally halogenated $C_1$-$C_6$-alkoxy (such as phenyl optionally substituted by 0, 1 or 2 V substituents each selected independently of one another from the group consisting of halogen (such as F, Cl), $C_1$-$C_3$-alkoxy (such as methoxy and ethoxy), $C_1$-$C_3$-alkyl (such as methyl), halogenated $C_1$-$C_3$-alkyl (such as $CF_3$) and cyano; or pyridyl, pyrimidinyl and thiophenyl optionally substituted by 0, 1 or 2 V substituents V each selected independently of one another from the group consisting of halogen (such as F, Cl), $C_1$-$C_3$-alkyl (such as methyl) halogenated $C_1$-$C_3$-alkyl (such as $CF_3$) and cyano).

Embodiments furthermore preferred relate to compounds of the formula (Ib)

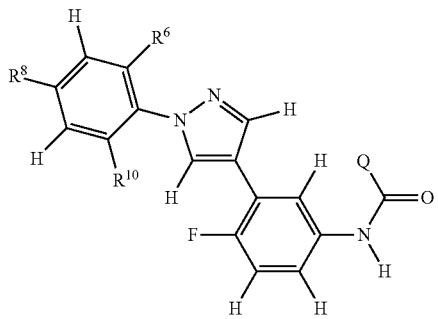

(Ib)

where $R^6$, $R^8$, $R^{10}$ and Q are defined as described in this application, preferably where $R^6$ is hydrogen, halogen, cyano, optionally substituted $C_1$-$C_6$-alkyl, more preferably halogen or optionally halogenated $C_1$-$C_6$-alkyl, still more preferably F, Cl, I, Br, $C_1$-$C_3$-alkyl (such as methyl) or perhalogenated $C_1$-$C_3$-alkyl, particularly preferably Cl, Br or $C_1$-$C_3$-alkyl (such as $CH_3$), especially preferably $CH_3$ or Br, $R^8$ is halogen or $C_1$-$C_6$-haloalkyl, preferably $C_1$-$C_6$-haloalkyl, more preferably perhalogenated $C_1$-$C_6$-alkyl, still more preferably perfluorinated $C_1$-$C_6$-alkyl such as $CF_3$, $C_2F_5$, $C_3F_7$, $C_4F_9$, especially preferably $C_3F_7$, $R^{10}$ is hydrogen, halogen, cyano, optionally substituted $C_1$-$C_6$-alkyl, more preferably halogen or optionally halogenated $C_1$-$C_6$-alkyl or optionally halogenated $C_1$-$C_6$-alkoxy (such as $OCF_3$ or $OCHF_2$), still more preferably F, Cl, Br, $C_1$-$C_3$-alkyl (such as methyl, ethyl) or perhalogenated $C_1$-$C_3$-alkyl, particularly preferably Cl, $C_1$-$C_3$-alkyl (such as methyl, ethyl) or perfluorinated $C_1$-$C_3$-alkyl (such as $CF_3$), especially preferably $CF_3$, and Q represents $C_3$-$C_6$-cycloalkyl optionally substituted by one substituent selected from the group consisting of halogen, $C_1$-$C_3$-alkyl and cyano (such as, for example, cyclopropyl optionally substituted by cyano or $C_1$-$C_3$-alkyl); $C_2$-$C_5$-heterocyclyl optionally substituted by one substituent selected from the group consisting of halogen or cyano, such as, for example, thietanyl (thiacyclobutanyl) optionally substituted by cyano or $C_1$-$C_3$-alkyl; an aryl substituted by 0, 1 or 2 V substituents or a 5- or 6-membered heteroaryl substituted by 0, 1, 2, 3 or 4 V substituents, wherein V is each independently of one another halogen (e.g. F, Cl), cyano, optionally halogenated $C_1$-$C_6$-alkyl, optionally halogenated $C_1$-$C_6$-alkoxy (such as phenyl optionally substituted by 0, 1 or 2 V substituents each selected independently of one another from the group consisting of halogen (such as F, Cl), $C_1$-$C_3$-alkoxy (such as methoxy and ethoxy), $C_1$-$C_3$-alkyl (such as methyl), halogenated $C_1$-$C_3$-alkyl (such as $CF_3$) and cyano; or pyridyl, thienyl, phenyl or oxazolyl optionally substituted by 0, 1 or 2 V substituents V each selected independently of one another from the group consisting of halogen (such as F, Cl), $C_1$-$C_3$-alkyl (such as methyl) halogenated $C_1$-$C_3$-alkyl (such as $CF_3$) and cyano).

preferably a pyridyl, thienyl, phenyl or oxazolyl substituted by 0, 1 or 2 V substituents, where V is in each case independently of one another F, Cl, CN, $C_1$-$C_3$-alkoxy (such as methoxy).

Isomers

Depending on the nature of the substituents, the compounds of the formula (I) may take the form of geometric and/or optically active isomers or corresponding isomer mixtures in different compositions. These stereoisomers are, for example, enantiomers, diastereomers, atropisomers or geometric isomers. The invention therefore encompasses pure stereoisomers and any desired mixtures of these isomers.

Methods and Uses

The invention also relates to methods for controlling animal pests, in which compounds of the formula (I) are allowed to act on animal pests and/or their habitat. The control of the animal pests is preferably carried out in agriculture and forestry, and in material protection. This preferably excludes methods for surgical or therapeutic treatment of the human or animal body and diagnostic methods carried out on the human or animal body.

The invention further relates to the use of the compounds of the formula (I) as pesticides, especially crop protection agents.

In the context of the present application, the term "pesticide" also always encompasses the term "crop protection agent".

The compounds of the formula (I), given good plant tolerance, favourable homeotherm toxicity and good environmental compatibility, are suitable for protecting plants and plant organs against biotic and abiotic stress factors, for increasing harvest yields, for improving the quality of the harvested material and for controlling animal pests, especially insects, arachnids, helminths, nematodes and molluscs, which are encountered in agriculture, in horticulture, in animal husbandry, in aquatic cultures, in forests, in gardens and leisure facilities, in the protection of stored products and of materials, and in the hygiene sector.

In the context of the present patent application, the term "hygiene" is understood as meaning the entirety of all measures, processes and procedures whose aim it is to prevent disorders—in particular infective diseases—and to serve to keep humans, animals and/or the environment healthy and/or to maintain cleanliness. According to the invention, this includes in particular measures for cleaning, disinfecting and sterilizing, for example, textiles or hard surfaces, mainly made of glass, wood, concrete, porcelain, ceramic, plastic or else made of metal(s), and keeping them clean of hygiene pests and/or their faeces. Excluded according to the invention are in this respect again processes for the surgical or therapeutic treatment of the human or animal body and diagnostic processes undertaken on the human or animal body.

The term "hygiene sector" thus includes all areas, technical fields and commercial utilizations in which such hygiene measures, processes and procedures are of importance, for example hygiene in kitchens, bakeries, airports, baths, swimming pools, shopping centres, hotels, hospitals, stables, etc.

Accordingly, the term "hygiene pest" is understood as meaning one or more animal pests whose presence in the hygiene sector is problematic, in particular for health reasons. Accordingly, the main aim is to minimize or prevent hygiene pests or contact therewith in the hygiene sector. This can be effected, in particular, by using a pesticide, where the agent can be employed both prophylactically and only in the case of infestation to control the pest. It is also possible to use agents which act by avoiding or reducing contact with the pest. Hygiene pests are, for example, the organisms mentioned below.

Thus, the term "hygiene protection" includes all actions which serve to maintain and/or improve such hygiene measures, processes and procedures.

The compounds of the formula (I) can preferably be used as pesticides. They are active against normally sensitive and resistant species and also against all or specific stages of development. The abovementioned pests include:

Pests from the phylum of the Arthropoda, especially from the class of the Arachnida, for example *Acarus* spp., for example *Acarus siro, Aceria kuko, Aceria sheldoni, Aculops* spp., *Aculus* spp., for example *Aculus fockeui, Aculus schlechtendali, Amblyomma* spp., *Amphitetranychus viennensis, Argas* spp., *Boophilus* spp., *Brevipalpus* spp., for example *Brevipalpus phoenicis, Bryobia graminum, Bryobia praetiosa, Centruroides* spp., *Chorioptes* spp., *Dermanyssus gallinae, Dermatophagoides pteronyssinus, Dermatophagoides farinae, Dermacentor* spp., *Eotetranychus* spp., for example *Eotetranychus hicoriae, Epitrimerus pyri, Eutetranychus* spp., for example *Eutetranychus banksi, Eriophyes* spp., for example *Eriophyes pyri, Glycyphagus domesticus, Halotydeus destructor, Hemitarsonemus* spp., for example *Hemitarsonemus latus* (=*Polyphagotarsonemus latus*), *Hyalomma* spp., *Ixodes* spp., *Latrodectus* spp., *Loxosceles* spp., *Neutrombicula autumnalis, Nuphersa* spp., *Oligonychus* spp., for example *Oligonychus coniferarum, Oligonychus ilicis, Oligonychus indicus, Oligonychus mangiferus, Oligonychus pratensis, Oligonychus punicae, Oligonychus yothersi, Ornithodorus* spp., *Ornithonyssus* spp., *Panonychus* spp., *for example Panonychus citri* (=*Metatetranychus citri*), *Panonychus ulmi* (=*Metatetranychus ulmi*), *Phyllocoptruta oleivora, Platytetranychus multidigituli, Polyphagotarsonemus latus, Psoroptes* spp., *Rhipicephalus* spp., *Rhizoglyphus* spp., *Sarcoptes* spp., *Scorpio maurus, Steneotarsonemus* spp., *Steneotarsonemus spinki, Tarsonemus* spp., for example *Tarsonemus confusus, Tarsonemus pallidus, Tetranychus* spp., for example *Tetranychus canadensis, Tetranychus cinnabarinus, Tetranychus turkestani, Tetranychus urticae, Trombicula alfreddugesi, Vaejovis* spp., *Vasates lycopersici;* from the class of the Chilopoda, for example *Geophilus* spp., *Scutigera* spp.;

from the order or the class of the Collembola, for example *Onychiurus armatus; Sminthurus viridis;* from the class of the Diplopoda, for example *Blaniulus guttulatus;* from the class of the Insecta, for example from the order of the Blattodea, for example *Blatta orientalis, Blattella asahinai, Blattella germanica, Leucophaea maderae, Panchlora* spp., *Parcoblatta* spp., *Periplaneta* spp., for example *Periplaneta americana, Periplaneta australasiae, Supella longipalpa;* from the order of the Coleoptera, for example *Acalymma vittatum, Acanthoscelides obtectus, Adoretus* spp., *Agelastica alni, Agriotes* spp., for example *Agriotes linneatus, Agriotes mancus, Alphitobius diaperinus, Amphimallon solstitialis, Anobium punctatum, Anoplophora* spp., *Anthonomus* spp., for example *Anthonomus grandis, Anthrenus* spp., *Apion* spp., *Apogonia* spp., *Atomaria* spp., for example *Atomaria linearis, Attagenus* spp., *Baris caerulescens, Bruchidius obtectus, Bruchus* spp., for example *Bruchus pisorum, Bruchus rufimanus, Cassida* spp., *Cerotoma trifurcata, Ceutorhynchus* spp., for example *Ceutorhynchus assimilis, Ceutorhynchus quadridens, Ceutorhynchus rapae, Chaetocnema* spp., for example *Chaetocnema confinis, Chaetocnema denticulata, Chaetocnema ectypa, Cleonus mendicus, Conoderus* spp., *Cosmopolites* spp., for example *Cosmopolites sordidus, Costelytra zealandica, Ctenicera* spp., *Curculio* spp., for example *Curculio caryae, Curculio caryatrypes, Curculio obtusus, Curculio sayi, Cryptolestes ferrugineus, Cryptolestes pusillus, Cryptorhynchus lapathi, Cryptorhynchus mangiferae, Cylindrocopturus* spp., *Cylindrocopturus adspersus, Cylindrocopturus furnissi, Dermestes* spp., *Diabrotica* spp., for example *Diabrotica balteata, Diabrotica barberi, Diabrotica undecimpunctata howardi, Diabrotica undecimpunctata undecimpunctata, Diabrotica virgifera virgifera, Diabrotica virgifera zeae, Dichocrocis* spp., *Dicladispa armigera, Diloboderus* spp., *Epilachna* spp., for example *Epilachna borealis, Epilachna varivestis, Epitrix* spp., for example *Epitrix cucumeris, Epitrix fuscula, Epitrix hirtipennis, Epitrix subcrinita, Epitrix tuberis, Faustinus* spp., *Gibbium psylloides, Gnathocerus cornutus, Hellula undalis, Heteronychus arator, Heteronyx* spp., *Hylamorpha elegans, Hylotrupes bajulus, Hypera postica, Hypomeces squamosus, Hypothenemus* spp., for example *Hypothenemus hampei, Hypothenemus obscurus, Hypothenemus pubescens, Lachnosterna consanguinea, Lasioderma serricorne, Latheticus oryzae, Lathridius* spp., *Lema* spp., *Leptinotarsa decemlineata, Leucoptera* spp., for example *Leucoptera coffeella, Lissorhoptrus oryzophilus, Lixus* spp., *Luperomorpha xanthodera, Luperodes* spp., *Lyctus* spp., *Megascelis* spp., *Melanotus* spp., for example *Melanotus longulus oregonensis, Meligethes aeneus, Melolontha* spp., for example *Melolontha melolontha, Migdolus* spp., *Monochamus* spp., *Naupactus xanthographus, Necrobia* spp., *Niptus hololeucus, Oryctes rhinoceros, Oryzaephilus surinamensis, Oryzaphagus oryzae, Otiorhynchus* spp., for example *Otiorhynchus cribricollis, Otiorhynchus ligustici, Otiorhynchus ovatus, Otiorhynchus rugosostriarus, Otiorhynchus sulcatus, Oxycetonia jucunda, Phaedon cochleariae, Phyllophaga* spp., *Phyllophaga helleri, Phyllotreta* spp., for example *Phyllotreta armoraciae, Phyllotreta pusilla, Phyllotreta ramosa, Phyllotreta striolata, Popillia japonica, Premnotrypes* spp., *Prostephanus truncatus, Psylliodes* spp., for example *Psylliodes affinis, Psylliodes chrysocephala, Psylliodes punctulata, Ptinus* spp., *Rhizobius ventralis, Rhizopertha dominica, Sitophilus* spp., for example *Sitophilus granarius, Sitophilus linearis, Sitophilus oryzae, Sitophilus zeamais, Sphenophorus* spp., *Stegobium paniceum, Sternechus* spp., for example *Sternechus paludatus, Symphyletes* spp., *Tanymecus* spp., for example *Tanymecus dilaticollis, Tanymecus indicus, Tanymecus palliatus, Tenebrio molitor, Tenebrioides mauretanicus, Tribolium* spp., for example *Tribolium audax, Tribolium castaneum, Tribolium confusum, Trogoderma* spp., *Tychius* spp., *Xylotrechus* spp., *Zabrus* spp., for example *Zabrus tenebrioides;* from the order of the Diptera, for example *Aedes* spp., for example *Aedes aegypti, Aedes albopictus, Aedes sticticus, Aedes vexans, Agromyza* spp., for example *Agromyza frontella, Agromyza parvicornis, Anastrepha* spp., *Anopheles* spp., for example *Anopheles quadrimaculatus, Anopheles gambiae, Asphondylia* spp., *Bactrocera* spp., for example *Bactrocera cucurbitae, Bactrocera dorsalis, Bactrocera oleae, Bibio hortulanus, Calliphora erythrocephala, Calliphora vicina, Ceratitis capitata, Chironomus* spp., *Chrysomya* spp., *Chrysops* spp., *Chrysozona pluvialis, Cochliomya* spp., *Contarinia* spp., for example *Contarinia johnsoni, Contarinia nasturtii, Contarinia pyrivora, Contarinia schulzi, Contarinia sorghicola, Contarinia tritici, Cordylobia anthropophaga, Cricotopus sylvestris, Culex* spp., for example *Culex pipiens, Culex quinquefasciatus, Culicoides* spp., *Culiseta* spp., *Cuterebra* spp., *Dacus oleae, Dasineura* spp., for example *Dasineura brassicae, Delia* spp., for example *Delia antiqua, Delia coarctata, Delia florilega, Delia platura, Delia radicum, Dermatobia hominis, Drosophila* spp., for example *Drosphila melanogaster, Drosophila suzukii, Echinocnemus* spp., *Fannia* spp., *Gasterophilus* spp., *Glossina* spp., *Haematopota* spp., *Hydrellia* spp., *Hydrellia griseola, Hylemya* spp., *Hippobosca* spp., *Hypoderma* spp., *Liriomyza* spp., for example *Liriomyza brassicae, Liriomyza huidobrensis, Liriomyza sativae, Lucilia* spp., for example *Lucilia cuprina, Lutzomyia* spp., *Mansonia* spp., *Musca* spp., for example *Musca domestica, Musca domestica vicina, Oestrus* spp., *Oscinella frit, Paratanytarsus* spp., *Paralauterborniella subcincta, Pegomya* spp., for example *Pegomya betae, Pegomya hyoscyami, Pegomya rubivora, Phlebotomus* spp., *Phorbia* spp., *Phormia* spp., *Piophila casei, Prodiplosis* spp., *Psila rosae, Rhagoletis* spp., for example *Rhagoletis cingulata, Rhagoletis completa, Rhagoletis fausta, Rhagoletis indifferens, Rhagoletis mendax, Rhagoletis pomonella, Sarcophaga* spp., *Simulium* spp., for example *Simulium meridionale, Stomoxys* spp., *Tabanus* spp., *Tetanops* spp., *Tipula* spp., for example *Tipula paludosa, Tipula simplex;* from the order of the Hemiptera for example *Acizzia acaciaebaileyanae, Acizzia dodonaeae, Acizzia uncatoides, Acrida turrita, Acyrthosipon* spp., for example *Acyrthosiphon pisum, Acrogonia* spp., *Aeneolamia* spp., *Agonoscena* spp., *Aleyrodes proletella, Aleurolobus barodensis, Aleurothrixus floccosus, Allocaridara malayensis, Amrasca* spp., for example *Amrasca bigutulla, Amrasca devastans, Anuraphis cardui, Aonidiella* spp., for example *Aonidiella aurantii, Aonidiella citrina, Aonidiella inornata, Aphanostigma piri, Aphis* spp., for example *Aphis citricola, Aphis craccivora, Aphis fabae, Aphis forbesi, Aphis glycines, Aphis gossypii, Aphis hederae, Aphis illinoisensis, Aphis middletoni, Aphis nasturtii, Aphis nerii, Aphis pomi, Aphis spiraecola, Aphis viburniphila, Arboridia apicalis, Arytainilla* spp., *Aspidiella* spp., *Aspidiotus* spp., for example *Aspidiotus nerii, Atanus* spp., *Aulacorthum solani, Bemisia tabaci, Blastopsylla occidentalis, Boreioglycaspis melaleucae, Brachycaudus helichrysi, Brachycolus* spp., *Brevicoryne brassicae, Cacopsylla* spp., for example *Cacopsylla pyricola, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chondracris rosea, Chromaphis juglandicola, Chrysomphalus ficus, Cicadulina mbila, Coccomytilus halli, Coccus* spp., for example *Coccus hesperidum, Coccus longulus, Coccus pseudomagnoliarum, Coccus viridis, Cryptomyzus ribis, Cryptoneossa* spp., *Ctenarytaina* spp., *Dalbulus* spp., *Dialeurodes citri, Diaphorina citri, Diaspis* spp., *Drosicha* spp., *Dysaphis* spp., for example *Dysaphis apiifolia, Dysaphis plantaginea, Dysaphis tulipae, Dysmicoccus* spp., *Empoasca* spp., for example *Empoasca abrupta, Empoasca fabae, Empoasca maligna, Empoasca solana, Empoasca stevensi, Eriosoma* spp., for example *Eriosoma americanum, Eriosoma lanigerum, Eriosoma pyricola, Erythroneura* spp., *Eucalyptolyma* spp., *Euphyllura* spp., *Euscelis bilobatus, Ferrisia* spp., *Geococcus coffeae, Glycaspis* spp., *Heteropsylla cubana, Heteropsylla spinulosa, Homalodisca coagulata, Hyalopterus arundinis, Hyalopterus pruni, Icerya* spp., for example *Icerya purchasi, Idiocerus* spp., *Idioscopus* spp., *Laodelphax striatellus, Lecanium* spp., for example *Lecanium corni* (=*Parthenolecanium corni*), *Lepidosaphes* spp., for example *Lepidosaphes ulmi, Lipaphis erysimi, Lycorma delicatula, Macrosiphum* spp., for example *Macrosiphum euphorbiae, Macrosiphum lilii, Macrosiphum rosae, Macrosteles facifrons, Mahanarva* spp., *Melanaphis sacchari, Metcalfiella* spp., *Metcalfa pruinosa, Metopolophium dirhodum, Monellia costalis, Monelliopsis pecanis, Myzus* spp., for example *Myzus ascalonicus, Myzus cerasi, Myzus ligustri, Myzus ornatus, Myzus persicae, Myzus nicotianae, Nasonovia ribisnigri, Nephotettix* spp., for example *Nephotettix cincticeps, Nephotettix nigropictus, Nilaparvata lugens, Oncometopia* spp., *Orthezia praelonga, Oxya chinensis, Pachypsylla* spp., *Parabemisia myricae, Paratrioza* spp., for example *Paratrioza cockerelli, Parlatoria* spp., *Pemphigus* spp., for example *Pemphigus bursarius, Pemphigus populivenae, Peregrinus maidis, Phenacoccus* spp., for example *Phenacoccus madeirensis, Phloeomyzus passerinii, Phorodon humuli, Phylloxera* spp., for example *Phylloxera devastatrix, Phylloxera notabilis, Pinnaspis aspidistrae, Planococcus* spp., for example *Planococcus citri, Prosopidopsylla flava, Protopulvinaria pyriformis, Pseudaulacaspis pentagona, Pseudococcus* spp., for example *Pseudococcus calceolariae, Pseudococcus comstocki, Pseudococcus longispinus, Pseudococcus maritimus, Pseudococcus viburni, Psyllopsis* spp., *Psylla* spp., for example *Psylla buxi, Psylla mali, Psylla pyri, Pteromalus* spp., *Pyrilla* spp., *Quadraspidiotus* spp., for example *Quadraspidiotus juglansregiae, Quadraspidiotus ostreaeformis, Quadraspidiotus perniciosus, Quesada gigas, Rastrococcus* spp., *Rhopalosiphum* spp., for example *Rhopalosiphum maidis, Rhopalosiphum oxyacanthae, Rhopalosiphum padi, Rhopalosiphum rufiabdominale, Saissetia* spp., for example *Saissetia coffeae, Saissetia miranda, Saissetia neglecta, Saissetia oleae, Scaphoideus titanus, Schizaphis graminum, Selenaspidus articulatus, Sitobion avenae, Sogata* spp., *Sogatella furcifera, Sogatodes* spp., *Stictocephala festina, Siphoninus phillyreae, Tenalaphara malayensis, Tetragonocephela* spp., *Tinocallis caryaefoliae, Tomaspis* spp., *Toxoptera* spp., for example *Toxoptera aurantii, Toxoptera citricidus, Trialeurodes vaporariorum, Trioza* spp., for example *Trioza diospyri, Typhlocyba* spp., *Unaspis* spp., *Viteus vitifolii, Zygina* spp.;

from the suborder of the Heteroptera, for example *Anasa tristis, Antestiopsis* spp., *Boisea* spp., *Blissus* spp., *Calocoris* spp., *Campylomma livida, Cavelerius* spp., *Cimex* spp., for example *Cimex adjunctus, Cimex hemipterus, Cimex lectularius, Cimex pilosellus, Collaria* spp., *Creontiades dilutus, Dasynus piperis, Dichelops furcatus, Diconocoris hewetti, Dysdercus* spp., *Euschistus* spp., for example *Euschistus heros, Euschistus servus, Euschistus tristigmus, Euschistus variolarius, Eurygaster* spp., *Halyomorpha halys, Heliopeltis* spp., *Horcias nobilellus, Leptocorisa* spp., *Leptocorisa varicornis, Leptoglossus occidentalis, Leptoglossus phyllopus, Lygocoris* spp., for example *Lygocoris pabulinus, Lygus* spp., for example *Lygus elisus, Lygus hesperus, Lygus lineolaris, Macropes excavatus, Monalonion atratum, Nezara* spp., for example *Nezara viridula, Oebalus* spp., *Piesma quadrata, Piezodorus* spp., for example *Piezodorus guildinii, Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.;

from the order of the Hymenoptera, for example *Acromyrmex* spp., *Athalia* spp., for example *Athalia rosae, Atta* spp., *Diprion* spp., for example *Diprion similis, Hoplocampa* spp., for example *Hoplocampa cookei, Hoplocampa testudinea, Lasius* spp., *Linepithema humile, Monomorium pharaonis, Sirex* spp., *Solenopsis invicta, Tapinoma* spp., *Urocerus* spp., *Vespa* spp., for example *Vespa crabro, Xeris* spp.;

from the order of the Isopoda, for example *Armadillidium vulgare, Oniscus asellus, Porcellio scaber;* from the order of the Isoptera, for example *Coptotermes* spp., for example *Coptotermes formosanus, Cornitermes cumulans, Cryptotermes* spp., *Incisitermes* spp., *Microtermes obesi, Odontotermes* spp., *Reticulitermes* spp., for example *Reticulitermes flavipes, Reticulitermes hesperus;* from the order of the Lepidoptera, for example *Achroia grisella, Acronicta major, Adoxophyes* spp., for example *Adoxophyes orana, Aedia leucomelas, Agrotis* spp., for example *Agrotis segetum, Agrotis ipsilon, Alabama* spp., for example *Alabama argillacea, Amyelois transitella, Anarsia* spp., *Anticarsia* spp., for example *Anticarsia gemmatalis, Argyroploce* spp., *Barathra brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Cheimatobia brumata, Chilo* spp., for example *Chilo plejadellus, Chilo suppressalis, Choristoneura* spp., *Clysia ambiguella, Cnaphalocerus* spp., *Cnaphalocrocis medinalis, Cnephasia* spp., *Conopomorpha* spp., *Conotrachelus* spp., *Copitarsia* spp., *Cydia* spp., for example *Cydia nigricana, Cydia pomonella, Dalaca noctuides, Diaphania* spp., *Diatraea saccharalis, Earias* spp., *Ecdytolopha aurantium, Elasmopalpus lignosellus, Eldana saccharina, Ephestia* spp., for example *Ephestia elutella, Ephestia kuehniella, Epinotia* spp., *Epiphyas postvittana, Etiella* spp., *Eulia* spp., *Eupoecilia ambiguella, Euproctis* spp., for example *Euproctis chrysorrhoea, Euxoa* spp., *Feltia* spp., *Galleria mellonella, Gracillaria* spp., *Grapholitha* spp., for example *Grapholita molesta, Grapholita prunivora, Hedylepta* spp., *Helicoverpa* spp., for example *Helicoverpa armigera, Helicoverpa zea, Heliothis* spp., for example *Heliothis virescens, Hofmannophila pseudospretella, Homoeosoma* spp., *Homona* spp., *Hyponomeuta padella, Kakivoria flavofasciata, Laphygma* spp., *Leucinodes orbonalis, Leucoptera* spp., for example *Leucoptera coffeella, Lithocolletis* spp., for example *Lithocolletis blancardella, Lithophane antennata, Lobesia* spp., for example *Lobesia botrana, Loxagrotis albicosta, Lymantria* spp., for example *Lymantria dispar, Lyonetia* spp., for example *Lyonetia clerkella, Malacosoma neustria, Maruca testulalis, Mamestra brassicae, Melanitis leda, Mocis* spp., *Monopis obviella, Mythimna separata, Nemapogon cloacellus, Nymphula* spp., *Oiketicus* spp., *Oria* spp., *Orthaga* spp., *Ostrinia* spp., for example *Ostrinia nubilalis, Oulema melanopus, Oulema oryzae, Panolis flammea, Parnara* spp., *Pectinophora* spp., for example *Pectinophora gossypiella, Perileucoptera* spp., *Phthorimaea* spp., for example *Phthorimaea operculella, Phyllocnistis citrella, Phyllonorycter* spp., for example *Phyllonorycter blancardella, Phyllonorycter crataegella, Pieris* spp., for example *Pieris rapae, Platynota stultana, Plodia interpunctella, Plusia* spp., *Plutella xylostella* (=*Plutella maculipennis*), *Prays* spp., *Prodenia* spp., *Protoparce* spp., *Pseudaletia* spp., for example *Pseudaletia unipuncta, Pseudoplusia includens, Pyrausta nubilalis, Rachiplusia nu, Schoenobius* spp., for example *Schoenobius bipunctifer, Scirpophaga* spp., for example *Scirpophaga innotata, Scotia segetum, Sesamia* spp., for example *Sesamia inferens, Sparganothis* spp., *Spodoptera* spp., for example *Spodoptera eradiana, Spodoptera exigua, Spodoptera frugiperda, Spodoptera praefica, Stathmopoda* spp., *Stomopteryx subsecivella, Synanthedon* spp., *Tecia solanivora, Thermesia gemmatalis, Tinea cloacella, Tinea pellionella, Tineola bisselliella, Tortrix* spp., *Trichophaga tapetzella, Trichoplusia* spp., for example *Trichoplusia ni, Tryporyza incertulas, Tuta absoluta, Virachola* spp.;

from the order of the Orthoptera or Saltatoria, for example *Acheta domesticus, Dichroplus* spp., *Gryllotalpa* spp., for example *Gryllotalpa gryllotalpa, Hieroglyphus* spp., *Locusta* spp., for example *Locusta migratoria, Melanoplus* spp., for example *Melanoplus devastator, Paratlanticus ussuriensis, Schistocerca gregaria*;

from the order of the Phthiraptera, for example *Damalinia* spp., *Haematopinus* spp., *Linognathus* spp., *Pediculus* spp., *Phylloxera vastatrix, Phthirus pubis, Trichodectes* spp.;

from the order of the Psocoptera, for example *Lepinotus* spp., *Liposcelis* spp.;

from the order of the Siphonaptera, for example *Ceratophyllus* spp., *Ctenocephalides* spp., for example *Ctenocephalides canis, Ctenocephalides felis, Pulex irritans, Tunga penetrans, Xenopsylla cheopis*;

from the order of the Thysanoptera, for example *Anaphothrips obscurus, Baliothrips biformis, Drepanothrips reuteri, Enneothrips flavens, Frankliniella* spp., for example *Frankliniella fusca, Frankliniella occidentalis, Frankliniella schultzei, Frankliniella tritici, Frankliniella vaccinii, Frankliniella williamsi, Heliothrips* spp., *Hercinothrips femoralis, Rhipiphorothrips cruentatus, Scirtothrips* spp., *Taeniothrips cardamomi, Thrips* spp., for example *Thrips palmi, Thrips tabaci*;

from the order of the Zygentoma (=Thysanura), for example *Ctenolepisma* spp., *Lepisma saccharina, Lepismodes inquilinus, Thermobia domestica*;

from the class of the Symphyla, for example *Scutigerella* spp., for example *Scutigerella immaculata*;

pests from the phylum of the Mollusca, in particular from the class of the Bivalvia, for example *Dreissena* spp.;

and also from the class of the Gastropoda, for example *Arion* spp., for example *Arion ater rufus, Biomphalaria* spp., *Bulinus* spp., *Deroceras* spp., for example *Deroceras laeve, Galba* spp., *Lymnaea* spp., *Oncomelania* spp., *Pomacea* spp., *Succinea* spp.;

animal and human parasites from the phyla of the Platyhelminthes and Nematoda, for example *Aelurostrongylus* spp., *Amidostomum* spp., *Ancylostoma* spp., *Angiostrongylus* spp., *Anisakis* spp., *Anoplocephala* spp., *Ascaris* spp., *Ascaridia* spp., *Baylisascaris* spp., *Brugia* spp., *Bunostomum* spp., *Capillaria* spp., *Chabertia* spp., *Clonorchis* spp., *Cooperia* spp., *Crenosoma* spp., *Cyathostoma* spp., *Dicrocoelium* spp., *Dictyocaulus* spp., *Diphyllobothrium* spp., *Dipylidium* spp., *Dirofilaria* spp., *Dracunculus* spp., *Echinococcus* spp., *Echinostoma* spp., *Enterobius* spp., *Eucoleus* spp., *Fasciola* spp., *Fascioloides* spp., *Fasciolopsis* spp., *Filaroides* spp., *Gongylonema* spp., *Gyrodactylus* spp., *Habronema* spp., *Haemonchus* spp., *Heligmosomoides* spp., *Heterakis* spp., *Hymenolepis* spp., *Hyostrongylus* spp., *Litomosoides* spp., *Loa* spp., *Metastrongylus* spp., *Metorchis* spp., *Mesocestoides* spp., *Moniezia* spp., *Muellerius* spp., *Necator* spp., *Nematodirus* spp., *Nippostrongylus* spp., *Oesophagostomum* spp., *Ollulanus* spp., *Onchocerca* spp., *Opisthorchis* spp., *Oslerus* spp., *Ostertagia* spp., *Oxyuris* spp., *Paracapillaria* spp., *Parafilaria* spp., *Paragonimus* spp., *Paramphistomum* spp., *Paranoplocephala* spp., *Parascaris* spp., *Passalurus* spp., *Protostrongylus* spp., *Schistosoma* spp., *Setaria* spp., *Spirocerca* spp., *Stephanofilaria* spp., *Stephanurus* spp., *Strongyloides* spp., *Strongylus* spp., *Syngamus* spp., *Taenia* spp., *Teladorsagia* spp., *Thelazia* spp., *Toxascaris* spp., *Toxocara* spp., *Trichinella* spp., *Trichobilharzia* spp., *Trichostrongylus* spp., *Trichuris* spp., *Uncinaria* spp., *Wuchereria* spp.;

plant pests from the phylum of the Nematoda, i.e. phytoparasitic nematodes, especially *Aglenchus* spp., *for example Aglenchus agricola, Anguina* spp., for example *Anguina tritici, Aphelenchoides* spp., for example *Aphelenchoides arachidis, Aphelenchoides fragariae, Belonolaimus* spp., for example *Belonolaimus gracilis, Belonolaimus longicaudatus, Belonolaimus nortoni, Bursaphelenchus* spp., for example *Bursaphelenchus cocophilus, Bursaphelenchus eremus, Bursaphelenchus xylophilus, Cacopaurus* spp., for example *Cacopaurus pestis*, *Criconemella* spp., for example *Criconemella curvata*, *Criconemella onoensis*, *Criconemella ornata*, *Criconemella rusium*, *Criconemella xenoplax* (=*Mesocriconema xenoplax*), *Criconemoides* spp., for example *Criconemoides ferniae*, *Criconemoides onoense*, *Criconemoides ornatum*, *Ditylenchus* spp., for example *Ditylenchus dipsaci*, *Dolichodorus* spp., *Globodera* spp., for example *Globodera pallida*, *Globodera rostochiensis*, *Helicotylenchus* spp., for example *Helicotylenchus dihystera*, *Hemicriconemoides* spp., *Hemicycliophora* spp., *Heterodera* spp., *for example Heterodera avenae*, *Heterodera glycines*, *Heterodera schachtii*, *Hoplolaimus* spp., *Longidorus* spp., for example *Longidorus africanus*, *Meloidogyne* spp., for example *Meloidogyne chitwoodi*, *Meloidogyne fallax*, *Meloidogyne hapla*, *Meloidogyne incognita*, *Meloinema* spp., *Nacobbus* spp., *Neotylenchus* spp., *Paraphelenchus* spp., *Paratrichodorus* spp., for example *Paratrichodorus minor*, *Pratylenchus* spp., for example *Pratylenchus penetrans*, *Pseudohalenchus* spp., *Psilenchus* spp., *Punctodera* spp., *Quinisulcius* spp., *Radopholus* spp., for example *Radopholus citrophilus*, *Radopholus similis*, *Rotylenchulus* spp., *Rotylenchus* spp., *Scutellonema* spp., *Subanguina* spp., *Trichodorus* spp., *for example Trichodorus obtusus*, *Trichodorus primitivus*, *Tylenchorhynchus* spp., for example *Tylenchorhynchus annulatus*, *Tylenchulus* spp., for example *Tylenchulus semipenetrans*, *Xiphinema* spp., for example *Xiphinema index*.

In addition, it is possible to control, from the sub-kingdom of the Protozoa, the order of the Coccidia, for example *Eimeria* spp.

The compounds of the formula (I) can, as the case may be, at certain concentrations or application rates, also be used as herbicides, safeners, growth regulators or agents to improve plant properties, as microbicides or gametocides, for example as fungicides, antimycotics, bactericides, virucides (including agents against viroids) or as agents against MLO (*mycoplasma*-like organisms) and RLO (*rickettsia*-like organisms). They can, as the case may be, also be used as intermediates or precursors for the synthesis of other active ingredients.

Formulations

The present invention further relates to formulations and use forms prepared therefrom as pesticides, for example drench, drip and spray liquors, comprising at least one compound of the formula (I). Optionally, the use forms comprise further pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulphate or diammonium hydrogenphosphate and/or retention promoters, for example dioctyl sulphosuccinate or hydroxypropylguar polymers and/or humectants, for example glycerol and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations, in addition to one or more compounds of the formula (I), optionally comprise further agrochemically active ingredients.

Preference is given to formulations or use forms comprising auxiliaries, for example extenders, solvents, spontaneity promoters, carriers, emulsifiers, dispersants, frost protection agents, biocides, thickeners and/or further auxiliaries, for example adjuvants. An adjuvant in this context is a component which enhances the biological effect of the formulation, without the component itself having any biological effect. Examples of adjuvants are agents which promote retention, spreading, attachment to the leaf surface or penetration.

These formulations are prepared in a known way, for example by mixing the compounds of the formula (I) with auxiliaries, for example extenders, solvents and/or solid carriers and/or other auxiliaries, for example surfactants. The formulations are produced either in suitable facilities or else before or during application.

The auxiliaries used may be substances suitable for imparting special properties, such as certain physical, technical and/or biological properties, to the formulation of the compounds of the formula (I), or to the use forms prepared from these formulations (for example ready-to-use pesticides such as spray liquors or seed dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the simple and substituted amines, amides, lactams (such as N-alkylpyrrolidones) and lactones, the sulfones and sulphoxides (such as dimethyl sulphoxide).

If the extender utilized is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and water.

In principle, it is possible to use all suitable solvents. Examples of suitable solvents are aromatic hydrocarbons, such as xylene, toluene or alkylnaphthalenes, chlorinated aromatic or aliphatic hydrocarbons, such as chlorobenzene, chloroethylene or methylene chloride, aliphatic hydrocarbons, such as cyclohexane, paraffins, mineral oil fractions, mineral and vegetable oils, alcohols, such as methanol, ethanol, isopropanol, butanol or glycol and their ethers and esters, ketones such as acetone, methyl ethyl ketone, methyl isobutyl ketone or cyclohexanone, strongly polar solvents, such as dimethyl sulphoxide, and also water.

In principle, it is possible to use all suitable carriers. Useful carriers especially include: for example ammonium salts and ground natural minerals such as kaolins, clays, talc, chalk, quartz, attapulgite, montmorillonite or diatomaceous earth, and ground synthetic minerals such as finely divided silica, alumina and natural or synthetic silicates, resins, waxes and/or solid fertilizers. It is likewise possible to use mixtures of such carriers. Useful carriers for granules include: for example crushed and fractionated natural rocks such as calcite, marble, pumice, sepiolite, dolomite, and synthetic granules of inorganic and organic flours, and also granules of organic material such as sawdust, paper, coconut shells, maize cobs and tobacco stalks.

It is also possible to use liquefied gaseous extenders or solvents. Especially suitable are those extenders or carriers which are gaseous at standard temperature and under atmospheric pressure, for example aerosol propellants such as halogenated hydrocarbons, and also butane, propane, nitrogen and carbon dioxide.

Examples of emulsifiers and/or foam formers, dispersants or wetting agents having ionic or nonionic properties or mixtures of these surface-active substances are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyl taurates), phosphoric esters of polyethoxylated alcohols or phenols, fatty acid esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is advantageous if one of the compounds of the formula (I) and/or one of the inert carriers is insoluble in water and if the application takes place in water.

Further auxiliaries which may be present in the formulations and the use forms derived therefrom are dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

Additional components which may be present are stabilizers, such as cold stabilizers, preservatives, antioxidants, light stabilizers, or other agents which improve chemical and/or physical stability. Foam generators or antifoams may also be present.

In addition, the formulations and the use forms derived therefrom may also comprise, as additional auxiliaries, stickers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids. Further auxiliaries may be mineral and vegetable oils.

It is possible if appropriate for still further auxiliaries to be present in the formulations and the use forms derived therefrom. Examples of such additives are fragrances, protective colloids, binders, adhesives, thickeners, thixotropic agents, penetrants, retention promoters, stabilizers, sequestrants, complexing agents, humectants, spreaders. In general, the compounds of the formula (I) can be combined with any solid or liquid additive commonly used for formulation purposes.

Useful retention promoters include all those substances which reduce dynamic surface tension, for example dioctyl sulphosuccinate, or increase viscoelasticity, for example hydroxypropylguar polymers.

Useful penetrants in the present context are all those substances which are typically used to improve the penetration of active agrochemical ingredients into plants. Penetrants are defined in this context by their ability to penetrate from the (generally aqueous) application liquor and/or from the spray coating into the cuticle of the plant and hence increase the mobility of the active ingredients in the cuticle. The method described in the literature (Baur et al., 1997, Pesticide Science 51, 131-152) can be used for determining this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulphate or diammonium hydrogenphosphate.

The formulations preferably comprise between 0.00000001% and 98% by weight of the compound of the formula (I), more preferably between 0.01% and 95% by weight of the compound of the formula (I), most preferably between 0.5% and 90% by weight of the compound of the formula (I), based on the weight of the formulation.

The content of the compound of the formula (I) in the use forms prepared from the formulations (in particular pesticides) may vary within wide ranges. The concentration of the compound of the formula (I) in the use forms may typically be between 0.00000001% and 95% by weight of the compound of the formula (I), preferably between 0.00001% and 1% by weight, based on the weight of the use form. Application is accomplished in a customary manner appropriate for the use forms.

Mixtures

The compounds of the formula (I) can also be used in a mixture with one or more suitable fungicides, bactericides, acaricides, molluscicides, nematicides, insecticides, microbiological agents, beneficial organisms, herbicides, fertilizers, bird repellents, phytotonics, sterilants, safeners, semiochemicals and/or plant growth regulators, in order thus, for example, to broaden the spectrum of action, prolong the period of action, enhance the rate of action, prevent repellency or prevent evolution of resistance. In addition, active ingredient combinations of this kind can improve plant growth and/or tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processibility of the harvested products.

In addition, the compounds of the formula (I) may be present in a mixture with other active ingredients or semiochemicals such as attractants and/or bird repellents and/or plant activators and/or growth regulators and/or fertilizers. Likewise, the compounds of the formula (I) can be used in mixtures with agents to improve plant properties, for example growth, yield and quality of the harvested material.

In a particular embodiment according to the invention, the compounds of the formula (I) are present in formulations or in the use forms prepared from these formulations in a mixture with further compounds, preferably those as described below.

If one of the compounds mentioned below can occur in different tautomeric forms, these forms are also included even if not explicitly mentioned in each case.

Insecticides/Acaricides/Nematicides

The active ingredients specified here with their common names are known and are described for example in "The Pesticide Manual", 16th ed., British Crop Protection Council 2012, or can be searched for on the Internet (e.g. http//www.alanwood.net/pesticides).

(1) Acetylcholinesterase (AChE) inhibitors, for example carbamates, e.g. alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, e.g. acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel antagonists, for example cyclodiene-organochlorines, e.g. chlordane and endosulfan or phenylpyrazoles (fiproles), e.g. ethiprole and fipronil.

(3) Sodium channel modulators/voltage-gated sodium channel blockers, for example pyrethroids, e.g. acrinathrin, allethrin, d-cis-trans allethrin, d-trans allethrin, bifenthrin, bioallethrin, bioallethrin S-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomers], deltamethrin, empenthrin [(EZ)-(1R) isomers], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans isomer], prallethrin, pyrethrins (pyrethrum), resmethrin, silafluofen, tefluthrin, tetramethrin, tetramethrin [(1R) isomers)], tralomethrin and transfluthrin or DDT or methoxychlor.

(4) Nicotinergic acetylcholine receptor (nAChR) agonists, for example neonicotinoids, e.g. acetamiprid, clothianidin, dinotefuran, imidacloprid, nitenpyram, thiacloprid and thiamethoxam or nicotine or sulfoxaflor or flupyradifurone.

(5) Nicotinergic acetylcholine receptor (nAChR) allosteric activators, for example spinosyns, e.g. spinetoram and spinosad.

(6) Chloride channel activators, for example avermectins/milbemycins, e.g. abamectin, emamectin benzoate, lepimectin and milbemectin.

(7) Juvenile hormone imitators, for example, juvenile hormone analogues e.g. hydroprene, kinoprene and methoprene or fenoxycarb or pyriproxyfen.

(8) Active ingredients with unknown or non-specific mechanisms of action, for example alkyl halides, e.g. methyl bromide and other alkyl halides; or chloropicrin or sulphuryl fluoride or borax or tartar emetic.

(9) Selective antifeedants, e.g. pymetrozine or flonicamid.

(10) Mite growth inhibitors, e.g. clofentezine, hexythiazox and diflovidazin or etoxazole.

(11) Microbial disruptors of insect midgut membranes, e.g. *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis*, and BT plant proteins: Cry1Ab, Cry1Ac, Cry1Fa, Cry2Ab, mCry3A, Cry3Ab, Cry3Bb, Cry34/35Ab1.

(12) Oxidative phosphorylation inhibitors, ATP disruptors, for example diafenthiuron or organotin compounds, e.g. azocyclotin, cyhexatin and fenbutatin oxide or propargite or tetradifon.

(13) Uncouplers of oxidative phosphorylation via disruption of the H proton gradient, for example chlorfenapyr, DNOC and sulfluramid.

(14) Nicotinic acetylcholine receptor antagonists, for example bensultap, cartap hydrochloride, thiocyclam, and thiosultap-sodium.

(15) Inhibitors of chitin biosynthesis, type 0, for example bistrifluron, chlorfluazuron, diflubenzuron, flucycloxuron, flufenoxuron, hexaflumuron, lufenuron, novaluron, noviflumuron, teflubenzuron and triflumuron.

(16) Inhibitors of chitin biosynthesis, type 1, for example buprofezin.

(17) Moulting disruptors (especially for Diptera, i.e. dipterans), for example cyromazine.

(18) Ecdysone receptor agonists, for example chromafenozide, halofenozide, methoxyfenozide and tebufenozide.

(19) Octopaminergic agonists, for example amitraz.

(20) Complex III electron transport inhibitors, for example hydramethylnon or acequinocyl or fluacrypyrim.

(21) Complex I electron transport inhibitors, for example METI acaricides, e.g. fenazaquin, fenpyroximate, pyrimidifen, pyridaben, tebufenpyrad and tolfenpyrad or rotenone (Derris).

(22) Voltage-gated sodium channel blockers, for example indoxacarb or metaflumizone.

(23) Inhibitors of acetyl-CoA carboxylase, for example tetronic and tetramic acid derivatives, e.g. spirodiclofen, spiromesifen and spirotetramat.

(24) Complex IV electron transport inhibitors, for example phosphines, e.g. aluminium phosphide, calcium phosphide, phosphine and zinc phosphide or cyanide.

(25) Complex II electron transport inhibitors, for example cyenopyrafen and cyflumetofen.

(28) Ryanodine receptor effectors, for example diamides, e.g. chlorantraniliprole, cyantraniliprole and flubendiamide.

Further active compounds having an unknown or unclear mechanism of action, for example afidopyropen, afoxolaner, azadirachtin, benclothiaz, benzoximate, bifenazate, broflanilide, bromopropylate, chinomethionat, cryolite, cyclaniliprole, cycloxaprid, cyhalodiamide, dicloromezotiaz, dicofol, diflovidazin, flometoquin, fluensulfone, flufenerim, flufenoxystrobin, flufiprole, fluhexafon, fluopyram, fluralaner, fufenozide, guadipyr, heptafluthrin, imidaclothiz, iprodione, lotilaner, meperfluthrin, paichongding, pyflubumide, pyridalyl, pyrifluquinazon, pyriminostrobin, sarolaner, tetramethylfluthrin, tetraniliprole, tetrachlorantraniliprole, tioxazafen, triflumezopyrim and iodomethane; and additionally preparations based on *Bacillus firmus* (I-1582, BioNeem, Votivo), and the following known active compounds: 1-{2-fluoro-4-methyl-5-[(2,2,2-trifluoroethyl)sulphinyl]phenyl}-3-(trifluoromethyl)-1H-1,2,4-triazole-5-amine (known from WO2006/043635), {1'-[(2E)-3-(4-chlorophenyl)prop-2-en-1-yl]-5-fluorospiro[indole-3,4'-piperidin]-1(2H)-yl}(2-chloropyridin-4-yl)methanone (known from WO2003/106457), 2-chloro-N-[2-{-[(2E)-3-(4-chlorophenyl)prop-2-en-1-yl]piperidin-4-yl}-4-(trifluoromethyl)phenyl]isonicotinamide (known from WO2006/

003494), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diazaspiro[4.5]dec-3-en-4-ylethyl carbonate (known from WO2009/049851), 4-(but-2-yn-1-yloxy)-6-(3,5-dimethylpiperidin-1-yl)-5-fluoropyrimidine (known from WO2004/099160), 4-(but-2-yn-1-yloxy)-6-(3-chlorophenyl)pyrimidine (known from WO2003/076415), PF1364 (CAS Reg. No. 1204776-60-2), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (known from WO2005/085216), N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN102057925), 8-chloro-N-[(2-chloro-5-methoxyphenyl)sulfonyl]-6-(trifluoromethyl)imidazo[1,2-a]pyridine-2-carboxamide (known from WO2010/129500), 4-[5-(3,5-dichlorophenyl)-5-(trifluoromethyl)-4,5-dihydro-1,2-oxazol-3-yl]-2-methyl-N-(1-oxidothietan-3-yl)benzamide (known from WO2009/080250), N-[(2E)-1-[(6-chloropyridin-3-yl)methyl]pyridin-2(1H)-ylidene]-2,2,2-trifluoroacetamide (known from WO2012/029672), 1-[(2-chloro-1,3-thiazol-5-yl)methyl]-4-oxo-3-phenyl-4H-pyrido[1,2-a]pyrimidin-1-ium-2-olate (known from WO2009/099929), 1-[(6-chloropyridin-3-yl)methyl]-4-oxo-3-phenyl-4H-pyrido[1,2-a]pyrimidin-1-ium-2-olate (known from WO2009/099929), 4-(3-{2,6-dichloro-4-[(3,3-dichloroprop-2-en-1-yl)oxy]phenoxy}propoxy)-2-methoxy-6-(trifluoromethyl)pyrimidine (known from CN101337940), N-[2-(tert-butylcarbamoyl)-4-chloro-6-methylphenyl]-1-(3-chloropyridin-2-yl)-3-(fluoromethoxy)-1H-pyrazole-5-carboxamide (known from WO2008/134969, 3-[benzoyl(methyl)amino]-N-[2-bromo-4-[1,2,2,2-tetrafluoro-1-(trifluoromethyl)ethyl]-6-(trifluoromethyl)phenyl]-2-fluorobenzamide (known from WO 2010018714), butyl [2-(2,4-dichlorophenyl)-3-oxo-4-oxaspiro[4.5]dec-1-en-1-yl]carbonate (known from CN 102060818), 4-[5-(3,5-dichlorophenyl)-5-(trifluoromethyl)-4H-isoxazol-3-yl]-N—[(Z)-methoxyiminomethyl]-2-methylbenzamide (known from WO2007/026965), (3E)-3-[1-[(6-chloro-3-pyridyl)methyl]-2-pyridylidene]-1,1,1-trifluoropropan-2-one (known from WO2013/144213, N-(methylsulfonyl)-6-[2-(pyridin-3-yl)-1,3-thiazol-5-yl]pyridine-2-carboxamide (known from WO2012/000896), N-[3-(benzylcarbamoyl)-4-chlorophenyl]-1-methyl-3-(pentafluoroethyl)-4-(trifluoromethyl)-1H-pyrazole-5-carboxamide (known from WO2010/051926).

Fungicides

The active compounds specified herein by their common name are known and described, for example, in "Pesticide Manual" or on the Internet (for example: http://www.alanwood.net/pesticides).

All the fungicidal mixing components listed in classes (1) to (15) may optionally form salts with corresponding bases or acids if suitable functional groups are present. In addition, the fungicidal mixing components listed in classes (1) to (15) also include tautomeric forms if tautomerism is possible.

1) inhibitors of the ergosterol biosynthesis, for example (1.01) aldimorph, (1.02) azaconazole, (1.03) bitertanol, (1.04) bromuconazole, (1.05) cyproconazole, (1.06) diclobutrazole, (1.07) difenoconazole, (1.08) diniconazole, (1.09) diniconazole-M, (1.10) dodemorph, (1.11) dodemorph acetate, (1.12) epoxiconazole, (1.13) etaconazole, (1.14) fenarimol, (1.15) fenbuconazole, (1.16) fenhexamide, (1.17) fenpropidin, (1.18) fenpropimorph, (1.19) fluquinconazole, (1.20) flurprimidol, (1.21) flusilazole, (1.22) flutriafol, (1.23) furconazole, (1.24) furconazole-cis, (1.25) hexaconazole, (1.26) imazalil, (1.27) imazalil sulphate, (1.28) imibenconazole, (1.29) ipconazole, (1.30) metconazole, (1.31) myclobutanil, (1.32) naftifine, (1.33) nuarimol, (1.34) oxpoconazole, (1.35) paclobutrazole, (1.36) pefurazoate, (1.37) penconazole, (1.38) piperalin, (1.39) prochloraz, (1.40) propiconazole, (1.41) prothioconazole, (1.42) pyributicarb, (1.43) pyrifenox, (1.44) quinconazole, (1.45) simeconazole, (1.46) spiroxamine, (1.47) tebuconazole, (1.48) terbinafin, (1.49) tetraconazole, (1.50) triadimefon, (1.51) triadimenol, (1.52) tridemorph, (1.53) triflumizole, (1.54) triforin, (1.55) triticonazole, (1.56) uniconazole, (1.57) uniconazole-p, (1.58) viniconazole, (1.59) voriconazole, (1.60) 1-(4-chlorophenyl)-2-(1H-1,2,4-triazol-1-yl)cycloheptanol, (1.61) 1-(2,2-dimethyl-2,3-dihydro-1H-inden-1-yl)-1H-imidazole-5-carboxylic acid methyl ester, (1.62) N'-{5-(difluoromethyl)-2-methyl-4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy]phenyl}imidoformamide, (1.64) O-[1-(4-methoxyphenoxy)-3,3-dimethylbutan-2-yl]-1H-imidazole-1-carbothioate, (1.65) pyrisoxazole, (1.66) 2-{[3-(2-chlorophenyl)-2-(2,4-difluorophenyl)oxiran-2-yl]methyl}-2,4-dihydro-3H-1,2,4-triazole-3-thione, (1.67) 1-{[3-(2-chlorophenyl)-2-(2,4-difluorophenyl)oxiran-2-yl]methyl}-1H-1,2,4-triazol-5-ylthiocyanate, (1.68) 5-(allylsulfanyl)-1-{[3-(2-chlorophenyl)-2-(2,4-difluorophenyl)oxiran-2-yl]methyl}-1H-1,2,4-triazole, (1.69) 2-[1-(2,4-dichlorophenyl)-5-hydroxy-2,6,6-trimethylheptan-4-yl]-2,4-dihydro-3H-1,2,4-triazole-3-thione, (1.70) 2-{[rel(2R,3S)-3-(2-chlorophenyl)-2-(2,4-difluorophenyl)oxiran-2-yl]methyl}-2,4-dihydro-3H-1,2,4-triazole-3-thione, (1.71) 2-{[rel(2R,3R)-3-(2-chlorophenyl)-2-(2,4-difluorophenyl)oxiran-2-yl]methyl}-2,4-dihydro-3H-1,2,4-triazole-3-thione, (1.72) 1-{[rel(2R,3S)-3-(2-chlorophenyl)-2-(2,4-difluorophenyl)oxiran-2-yl]methyl}-1H-1,2,4-triazol-5-ylthiocyanate, (1.73) 1-{[rel(2R,3R)-3-(2-chlorophenyl)-2-(2,4-difluorophenyl)oxiran-2-yl]methyl}-1H-1,2,4-triazol-5-ylthiocyanate, (1.74) 5-(allylsulfanyl)-1-{[rel(2R,3S)-3-(2-chlorophenyl)-2-(2,4-difluorophenyl)oxiran-2-yl]methyl}-1H-1,2,4-triazole, (1.75) 5-(allylsulfanyl)-1-{[rel(2R,3R)-3-(2-chlorophenyl)-2-(2,4-difluorophenyl)oxiran-2-yl]methyl}-1H-1,2,4-triazole, (1.76) 2-[(2S,4S,5S)-1-(2,4-dichlorophenyl)-5-hydroxy-2,6,6-trimethylheptan-4-yl]-2,4-dihydro-3H-1,2,4-triazole-3-thione, (1.77) 2-[(2R,4S,5S)-1-(2,4-dichlorophenyl)-5-hydroxy-2,6,6-trimethylheptan-4-yl]-2,4-dihydro-3H-1,2,4-triazole-3-thione, (1.78) 2-[(2R,4R,5R)-1-(2,4-dichlorophenyl)-5-hydroxy-2,6,6-trimethylheptan-4-yl]-2,4-dihydro-3H-1,2,4-triazole-3-thione, (1.79) 2-[(2S,4R,5R)-1-(2,4-dichlorophenyl)-5-hydroxy-2,6,6-trimethylheptan-4-yl]-2,4-dihydro-3H-1,2,4-triazole-3-thione, (1.80) 2-[(2S,4S,5R)-1-(2,4-dichlorophenyl)-5-hydroxy-2,6,6-trimethylheptan-4-yl]-2,4-dihydro-3H-1,2,4-triazole-3-thione, (1.81) 2-[(2R,4S,5R)-1-(2,4-dichlorophenyl)-5- hydroxy-2,6,6-trimethylheptan-4-yl]-2,4-dihydro-3H-1,2,4-triazole-3-thione, (1.82) 2-[(2R,4R,5S)-1-(2,4-dichlorophenyl)-5-hydroxy-2,6,6-trimethylheptan-4-yl]-2,4-dihydro-3H-1,2,4-triazole-3-thione, (1.83) 2-[(2S,4R,5S)-1-(2,4-dichlorophenyl)-5-hydroxy-2,6,6-trimethylheptan-4-yl]-2,4-dihydro-3H-1,2,4-triazole-3-thione, (1.84) 2-[4-(4-chlorophenoxy)-2-(trifluoromethyl)phenyl]-1-(1H-1,2,4-triazol-1-yl)propan-2-ol, (1.85) 2-[4-(4-chlorophenoxy)-2-(trifluoromethyl)phenyl]-1-(1H-1,2,4-triazol-1-yl)butan-2-ol, (1.86) 2-[4-(4-chlorophenoxy)-2-(trifluoromethyl)phenyl]-1-(1H-1,2,4-triazol-1-yl)pentan-2-ol, (1.87) 2-[2-chloro-4-(4-chlorophenoxy)phenyl]-1-(1H-1,2,4-triazol-1-yl)butan-2-ol, (1.88) 2-[2-chloro-4-(2,4-dichlorophenoxy)phenyl]-1-(1H-1,2,4-triazol-1-yl)propan-2-ol, (1.89) (2R)-2-(1-chlorocyclopropyl)-4-[(1R)-2,2-dichlorocyclopropyl]-1-(1H-1,2,4-triazol-1-yl)butan-2-ol, (1.90) (2R)-2-(1-chlorocyclopropyl)-4-[(1 S)-2,2-dichlorocyclopropyl]-1-(1H-1,2,4-triazol-1-yl)butan-2-ol, (1.91) (2S)-2-(I-chlorocyclopropyl)-4-[(1S)-2,2-dichlorocyclopropyl]-1-(1H-1,2,4-triazol-1-yl)butan-2-ol, (1.92) (2S)-2-(1-chlorocyclopropyl)-4-[(1R)-2,2-dichlorocyclopropyl]-1-(1H-1,2,4-triazol-1-yl)butan-2-ol, (1.93) (1S,2R,5R)-5-(4-chlorobenzyl)-2-(chloromethyl)-2-methyl-1-(1H-1,2,4-triazol-1-ylmethyl)cyclopentanol, (1.94) (1R,2S,5S)-5-(4-chlorobenzyl)-2-(chloromethyl)-2-methyl-1-(1H-1,2,4-triazol-1-ylmethyl)cyclopentanol, (1.95) 5-(4-chlorobenzyl)-2-(chloromethyl)-2-methyl-1-(1H-1,2,4-triazol-1-ylmethyl)cyclopentanol.

2) Inhibitors of complex I or II of the respiratory chain, for example (2.01) bixafen, (2.02) boscalid, (2.03) carboxin, (2.04) diflumetorim, (2.05) fenfuram, (2.06) fluopyram, (2.07) flutolanil, (2.08) fluxapyroxad, (2.09) furametpyr, (2.10) furmecyclox, (2.11) isopyrazam (mixture of syn-epimeric racemate 1RS,4SR,9RS and anti-epimeric racemate 1RS,4SR,9SR), (2.12) isopyrazam (anti-epimeric racemate 1RS,4SR,9SR), (2.13) isopyrazam (anti-epimeric enantiomer 1R,4S,9S), (2.14) isopyrazam (anti-epimeric enantiomer 1S,4R,9R), (2.15) isopyrazam (syn-epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil, (2.19) oxycarboxin, (2.20) penflufen, (2.21) penthiopyrad, (2.22) sedaxane, (2.23) thifluzamide, (2.24) 1-methyl-N-[2-(1,1,2,2-tetrafluoroethoxy)phenyl]-3-(trifluoromethyl)-H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide, (2.28) 5,8-difluoro-N-[2-(2-fluoro-4-{[4-(trifluoromethyl)pyridin-2-yl]oxy}phenyl)ethyl]quinazolin-4-amine, (2.29) benzovindiflupyr, (2.30) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (2.31) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.32) 3-(difluoromethyl)-1-methyl-N-(1,1,3-trimethyl-2,3-dihydro-1H-inden-4-yl)-1H-pyrazole-4-carboxamide, (2.33) 1,3,5-trimethyl-N-(1,1,3-trimethyl-2,3-dihydro-1H-inden-4-yl)-1H-pyrazole-4-carboxamide, (2.34) 1-methyl-3-(trifluoromethyl)-N-(1,1,3-trimethyl-2,3-dihydro-1H-inden-4-yl)-1H-pyrazole-4-carboxamide, (2.35) 1-methyl-3-(trifluoromethyl)-N-[(3R)-1,1,3-trimethyl-2,3-dihydro-1H-inden-4-yl]-1H-pyrazole-4-carboxamide, (2.36) 1-methyl-3-(trifluoromethyl)-N-[(3S)-1,1,3-trimethyl-2,3-dihydro-1H-inden-4-yl]-1H-pyrazole-4-carboxamide, (2.37) 3-(difluoromethyl)-1-methyl-N-[(3S)-1,1,3-trimethyl-2,3-dihydro-1H-inden-4-yl]-1H-pyrazole-4-carboxamide, (2.38) 3-(difluoromethyl)-1-methyl-N-[(3R)-1,1,3-trimethyl-2,3-dihydro-1H-inden-4-yl]-1H-pyrazole-4-carboxamide, (2.39) 1,3,5-trimethyl-N-[(3R)-1,1,3-trimethyl-2,3-dihydro-1H-inden-4-yl]-1H-pyrazole-4-carboxamide, (2.40) 1,3,5-trimethyl-N-[(3S)-1,1,3-trimethyl-2,3-dihydro-H-inden-4-yl]-1H-pyrazole-4-carboxamide, (2.41) benodanil, (2.42) 2-chloro-N-(1,1,3-trimethyl-2,3-dihydro-1H-inden-4-yl)pyridine-3-carboxamide, (2.43) isofetamide, (2.44) 1-methyl-3-(trifluoromethyl)-N-[2'-(trifluoromethyl)biphenyl-2-yl]-1H-pyrazole-4-carboxamide, (2.45) N-(4'-chlorobiphenyl-2-yl)-3-(difluoromethyl)-1-methyl-1H-pyrazole-4-carboxamide, (2.46) N-(2',4'-dichlorobiphenyl-2-yl)-3-(difluoromethyl)-1-methyl-1H-pyrazole-4-carboxamide, (2.47) 3-(difluoromethyl)-1-methyl-N-[4'-(trifluoromethyl)biphenyl-2-yl]-1H-pyrazole-4-carboxamide, (2.48) N-(2',5'-difluorobiphenyl-2-yl)-1-methyl-3-(trifluoromethyl)-1H-pyrazole-4-carboxamide, (2.49) 3-(difluoromethyl)-1-methyl-N-[4'-(prop-1-yn-1-yl)biphenyl-2-yl]-1H-pyrazole-4-carboxamide, (2.50) 5-fluoro-1,3-dimethyl-N-[4'-(prop-1-yn-1-yl)biphenyl-2-yl]-1H-pyrazole-4-carboxamide, (2.51) 2-chloro-N-[4'-(prop-1-yn-1-yl)biphenyl-2-yl]nicotinamide, (2.52) 3-(difluoromethyl)-N-[4'-(3,3-dimethylbut-1-yn-1-yl)biphenyl-2-yl]-1-methyl-1H-pyrazole-4-carboxamide, (2.53) N-[4'-(3,3-dimethylbut-1-yn-1-yl)biphenyl-2-yl]-5-fluoro-1,3-dimethyl-1H-pyrazole-4-carboxamide, (2.54) 3-(difluoromethyl)-N-(4'-ethynylbiphenyl-2-yl)-1-methyl-1H-pyrazole-4-carboxamide, (2.55) N-(4'-ethynylbiphenyl-2-yl)-5-fluoro-1,3-dimethyl-1H-pyrazole-4-carboxamide, (2.56) 2-chloro-N-(4'-ethynylbiphenyl-2-yl)nicotinamide, (2.57) 2-chloro-N-[4'-(3,3-dimethylbut-1-yn-1-yl)biphenyl-2-yl]nicotinamide, (2.58) 4-(difluoromethyl)-2-methyl-N-[4'-(trifluoromethyl)biphenyl-2-yl]-1,3-thiazole-5-carboxamide, (2.59) 5-fluoro-N-[4'-(3-hydroxy-3-methylbut-1-yn-1-yl)biphenyl-2-yl]-1,3-dimethyl-1H-pyrazole-4-carboxamide, (2.60) 2-chloro-N-[4'-(3-hydroxy-3-methylbut-1-yn-1-yl)biphenyl-2-yl]nicotinamide, (2.61) 3-(difluoromethyl)-N-[4'-(3-methoxy-3-methylbut-1-yn-1-yl)biphenyl-2-yl]-1-methyl-1H-pyrazole-4-carboxamide, (2.62) 5-fluoro-N-[4'-(3-methoxy-3-methylbut-1-yn-1-yl)biphenyl-2-yl]-1,3-dimethyl-1H-pyrazole-4-carboxamide, (2.63) 2-chloro-N-[4'-(3-methoxy-3-methylbut-1-yn-1-yl)biphenyl-2-yl]nicotinamide, (2.64) 1,3-dimethyl-N-(1,1,3-trimethyl-2,3-dihydro-1H-inden-4-yl)-1H-pyrazole-4-carboxamide, (2.65) 1,3-dimethyl-N-[(3R)-1,1,3-trimethyl-2,3-dihydro-1H-inden-4-yl]-1H-pyrazole-4-carboxamide, (2.66) 1,3-dimethyl-N-[(3S)-1,1,3-trimethyl-2,3-dihydro-H-inden-4-yl]-1H-pyrazole-4-carboxamide, (2.67) 3-(difluoromethyl)-N-methoxy-1-methyl-N-[1-(2,4,6-trichlorophenyl)propan-2-yl]-1H-pyrazole-4-carboxamide, (2.68) 3-(difluoromethyl)-N-(7-fluoro-1,1,3-trimethyl-2,3-dihydro-1H-inden-4-yl)-1-methyl-1H-pyrazole-4-carboxamide, (2.69) 3-(difluoromethyl)-N-[(3R)-7-fluoro-1,1,3-trimethyl-2,3-dihydro-1H-inden-4-yl]-1-methyl-1H-pyrazole-4-carboxamide, (2.70) 3-(difluoromethyl)-N-[(3S)-7-fluoro-1,1,3-trimethyl-2,3-dihydro-1H-inden-4-yl]-1-methyl-1H-pyrazole-4-carboxamide.

3) Inhibitors of the respiratory chain on complex III, for example (3.01) ametoctradin, (3.02) amisulbrom, (3.03) azoxystrobin, (3.04) cyazofamid, (3.05) coumethoxystrobin, (3.06) coumoxystrobin, (3.07) dimoxystrobin, (3.08) enoxastrobin, (3.09) famoxadon, (3.10) fenamidon, (3.11) flufenoxystrobin, (3.12) fluoxastrobin, (3.13) kresoxim-methyl, (3.14) metominostrobin, (3.15) orysastrobin, (3.16) picoxystrobin, (3.17) pyraclostrobin, (3.18) pyrametostrobin, (3.19) pyraoxystrobin, (3.20) pyribencarb, (3.21) triclopyricarb, (3.22) trifloxystrobin, (3.23) (2E)-2-(2-{[6-(3-chloro-2-methylphenoxy)-5-fluoropyrimidin-4-yl]oxy}phenyl)-2-(methoxyimino)-N-methylacetamide, (3.24) (2E)-2-(methoxyimino)-N-methyl-2-(2-{[({(1E)-1-[3-(trifluoromethyl)phenyl]ethyliden}amino)oxy]methyl}phenyl)acetamide, (3.25) (2E)-2-(methoxyimino)-N-methyl-2-{2-[(E)-({1-[3-(trifluoromethyl)phenyl]ethoxy}imino)methyl]phenyl}acetamide, (3.26) (2E)-2-{2-[({[(1E)-1-(3-{[(E)-1-fluoro-2-phenylvinyl]oxy}phenyl)ethyliden]amino}oxy)methyl]phenyl}-2-(methoxyimino)-N-methylacetamide, (3.27) fenaminostrobin, (3.28) 5-methoxy-2-methyl-4-(2-{[({(1E)-1-[3-(trifluoromethyl)phenyl]ethyliden}amino)oxy]methyl}phenyl)-2,4-dihydro-3H-1,2,4-triazol-3-one, (3.29) (2E)-2-{2-[({cyclopropyl[(4-methoxyphenyl)imino]methyl}sulfanyl)methyl]phenyl}-3-methoxyacrylic acid methyl ester, (3.30) N-(3-ethyl-3,5,5-trimethylcyclohexyl)-3-formamido-2-hydroxybenzamide, (3.31) 2-{2-[(2,5-dimethylphenoxy)methyl]phenyl}-2-methoxy-N-methylacetamide, (3.32) 2-{2-[(2,5-dimethylphenoxy)methyl]phenyl}-2-methoxy-N-methylacetamide, (3.33) (2E,3Z)-5-{[1-(4-chlorophenyl)-1H-pyrazol-3-yl]oxy}-2-(methoxyimino)-N,3-dimethylpent-3-enamide.

4) Mitosis and cell division inhibitors, for example (4.01) benomyl, (4.02) carbendazim, (4.03) chlorfenazole, (4.04) diethofencarb, (4.05) ethaboxam, (4.06) fluopicolide, (4.07) fuberidazole, (4.08) pencycuron, (4.09) thiabendazole, (4.10) thiophanate-methyl, (4.11) thiophanate, (4.12) zoxamide, (4.13) 5-chloro-7-(4-methylpiperidin-1-yl)-6-(2,4,6-trifluorophenyl)[1,2,4]triazolo[1,5-a]pyrimidine, (4.14) 3-chloro-5-(6-chloropyridin-3-yl)-6-methyl-4-(2,4,6-trifluorophenyl)pyridazine.

5) Compounds capable of having multisite action, for example (5.01) Bordeaux mixture, (5.02) captafol, (5.03) captan, (5.04) chlorothalonil, (5.05) copper hydroxide, (5.06) copper naphthenate, (5.07) copper oxide, (5.08) copper oxychloride, (5.09) copper (2+) sulphate, (5.10) dichlofluanid, (5.11) dithianon, (5.12) dodine, (5.13) dodine free base, (5.14) ferbam, (5.15) fluorofolpet, (5.16) folpet, (5.17) guazatine, (5.18) guazatine acetate, (5.19) iminoctadine, (5.20) iminoctadine albesilate, (5.21) iminoctadine triacetate, (5.22) mancopper, (5.23) mancozeb, (5.24) maneb, (5.25) metiram, (5.26) metiram zinc, (5.27) oxine-copper, (5.28) propamidine, (5.29) propineb, (5.30) sulphur and sulphur preparations including calcium polysulphide, (5.31) thiram, (5.32) tolylfluanid, (5.33) zineb, (5.34) ziram, (5.35) anilazine.

6) Compounds capable of inducing host defence, for example (6.01) acibenzolar-S-methyl, (6.02) isotianil, (6.03) probenazole, (6.04) tiadinil, (6.05) laminarin.

7) Amino acid and/or protein biosynthesis inhibitors, for example (7.01) andoprim, (7.02) blasticidin-S, (7.03) cyprodinil, (7.04) kasugamycin, (7.05) kasugamycin hydrochloride hydrate, (7.06) mepanipyrim, (7.07) pyrimethanil, (7.08) 3-(5-fluoro-3,3,4,4-tetramethyl-3,4-dihydroisoquinolin-1-yl)quinoline, (7.09) oxytetracycline, (7.10) streptomycin.

8) ATP production inhibitors, for example (8.01) fentin acetate, (8.02) fentin chloride, (8.03) fentin hydroxide, (8.04) silthiofam.

9) Cell wall synthesis inhibitors, for example (9.01) benthiavalicarb, (9.02) dimethomorph, (9.03) flumorph, (9.04) iprovalicarb, (9.05) mandipropamide, (9.06) polyoxins, (9.07) polyoxorim, (9.08) validamycin A, (9.09) valifenalate, (9.10) polyoxin B, (9.11) (2E)-3-(4-tert-butylphenyl)-3-(2-chloropyridin-4-yl)-1-(morpholin-4-yl)prop-2-en-1-one, (9.12) (2Z)-3-(4-tert-butylphenyl)-3-(2-chloropyridin-4-yl)-1-(morpholin-4-yl)prop-2-en-1-one.

10) Lipid and membrane synthesis inhibitors, for example (10.01) biphenyl, (10.02) chloroneb, (10.03) dicloran, (10.04) edifenphos, (10.05) etridiazole, (10.06) iodocarb, (10.07) iprobenfos, (10.08) isoprothiolane, (10.09) propamocarb, (10.10) propamocarb hydrochloride, (10.11) prothiocarb, (10.12) pyrazophos, (10.13) quintozene, (10.14) tecnazene, (10.15) tolclofos-methyl.

11) Melanin biosynthesis inhibitors, for example (11.01) carpropamide, (11.02) diclocymet, (11.03) fenoxanil, (11.04) phthalide, (11.05) pyroquilon, (11.06) tricyclazole, (11.07) 2,2,2-trifluoroethyl {3-methyl-1-[(4-methylbenzoyl)amino]butan-2-yl}carbamate.

12) Nucleic acid synthesis inhibitors, for example (12.01) benalaxyl, (12.02) benalaxyl-M (kiralaxyl), (12.03) bupirimate, (12.04) clozylacon, (12.05) dimethirimol, (12.06) ethirimol, (12.07) furalaxyl, (12.08) hymexazole, (12.09) metalaxyl, (12.10) metalaxyl-M (mefenoxam), (12.11) ofurace, (12.12) oxadixyl, (12.13) oxolinic acid, (12.14) octhilinone.

13) Signal transduction inhibitors, for example (13.01) chlozolinate, (13.02) fenpiclonil, (13.03) fludioxonil, (13.04) iprodione, (13.05) procymidone, (13.06) quinoxyfen, (13.07) vinclozolin, (13.08) proquinazid.

14) Compounds capable of acting as uncouplers, for example (14.01) binapacryl, (14.02) dinocap, (14.03) ferimzone, (14.04) fluazinam, (14.05) meptyldinocap.

15) Further compounds, for example (15.001) benthiazole, (15.002) bethoxazin, (15.003) capsimycin, (15.004) carvone, (15.005) quinomethionate, (15.006) pyrifenone (chlazafenone), (15.007) cufraneb, (15.008) cyflufenamid, (15.009) cymoxanil, (15.010) cyprosulphamide, (15.011) dazomet, (15.012) debacarb, (15.013) dichlorophen, (15.014) diclomezin, (15.015) difenzoquat, (15.016) difenzoquat metilsulphate, (15.017) diphenylamine, (15.018) Ecomate, (15.019) fenpyrazamine, (15.020) flumetover, (15.021) fluoroimide, (15.022) flusulphamide, (15.023) flutianil, (15.024) fosetyl-aluminium, (15.025) fosetyl-calcium, (15.026) fosetyl-sodium, (15.027) hexachlorobenzene, (15.028) irumamycin, (15.029) methasulphocarb, (15.030) methyl isothiocyanate, (15.031) metrafenone, (15.032) mildiomycin, (15.033) natamycin, (15.034) nickel dimethyldithiocarbamate, (15.035) nitrothal-isopropyl, (15.036) oxamocarb, (15.037) oxyfenthiin, (15.038) pentachlorophenol and salts, (15.039) phenothrin, (15.040) phosphorous acid and salts thereof, (15.041) propamocarb-fosetylate, (15.042) propanosin-sodium, (15.043) pyrimorph, (15.044) pyrrolnitrin, (15.045) tebufloquin, (15.046) tecloftalam, (15.047) tolnifanid, (15.048) triazoxide, (15.049) trichlamid, (15.050) zarilamid, (15.051) 2-methylpropanoic acid (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl ester, (15.052) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.053) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.054) oxathiapiproline, (15.055) 1H-imidazole-1-carboxylic acid 1-(4-methoxyphenyl)-3,3-dimethylbutan-2-yl ester, (15.056) 2,3,5,6-tetrachloro-4-(methylsulfonyl)pyridine, (15.057) 2,3-dibutyl-6-chlorothieno[2,3-d]pyrimidin-4(3H)-one, (15.058) 2,6-dimethyl-1H,5H-[1,4]dithiino[2,3-c:5,6-d]dipyrrole-1,3,5,7(2H,6H)-tetrone, (15.059) 2-[5-methyl-3-(trifluoromethyl)-H-pyrazol-1-yl]-1-(4-{4-[(5R)-5-phenyl-4,5-dihydro-1,2-oxazol-3-yl]-1,3-thiazol-2-yl}piperidin-1-yl)ethanone, (15.060) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, (15.061) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, (15.062) 2-butoxy-6-iodo-3-propyl-4H-chromen-4-one, (15.063) 2-chloro-5-[2-chloro-1-(2,6-difluoro-4-methoxyphenyl)-4-methyl-1H-imidazol-5-yl]pyridine, (15.064) 2-phenylphenol and salts, (15.065) 3-(4,4,5-trifluoro-3,3-dimethyl-3,4-dihydroisoquinolin-1-yl)quinoline, (15.066) 3,4,5-trichloropyridine-2,6-dicarboxylic acid nitrile, (15.067) 3-chloro-5-(4-chlorophenyl)-4-(2,6-difluorophenyl)-6-methylpyridazine, (15.068) 4-(4-chlorophenyl)-5-(2,6-difluorophenyl)-3,6-dimethylpyridazine, (15.069) 5-amino-1,3,4-thiadiazole-2-thiol, (15.070) 5-chloro-N'-phenyl-N'-(prop-2-in-1-yl)thiophene-2-sulphonohydrazide, (15.071) 5-fluoro-2-[(4-fluorobenzyl)oxy]pyrimidin-4-amine, (15.072) 5-fluoro-2-[(4-methylbenzyl)oxy]pyrimidin-4-amin, (15.073) 5-methyl-6-octyl[1,2,4]triazolo[1,5-a]pyrimidin-7-amin, (15.074) (2Z)-3-amino-2-cyano-3-phenylacrylic acid ethyl ester, (15.075) N'-(4-{[3-(4-chlorobenzyl)-1,2,4-thiadiazol-5-yl]oxy}-2,5-dimethylphenyl)-N-ethyl-N-methylimidoformamide, (15.076) N-(4-chlorobenzyl)-3-[3-methoxy-4-(prop-2-in-1-yloxy)phenyl]propanamide, (15.077) N-[(4-chlorophenyl)(cyano)methyl]-3-[3-methoxy-4-(prop-2-in-1-yloxy)phenyl]propanamide, (15.078) N-[(5-bromo-3-chloropyridin-2-yl)methyl]-2,4-dichloronicotinamide, (15.079) N-[1-(5-bromo-3-chloropyridin-2-yl)ethyl]-2,4-dichloronicotinamide, (15.080) N-[1-(5-bromo-3-chloropyridin-2-yl)ethyl]-2-fluoro-4-iodonicotinamide, (15.081) N-{(E)-[(cyclopropylmethoxy)imino][6-(difluoromethoxy)-2,3-difluorophenyl]methyl}-2-phenylacetamide, (15.082) N—{(Z)-[(cyclopropylmethoxy)imino][6-(difluoromethoxy)-2,3-difluorophenyl]methyl}-2-phenylacetamide, (15.083) N'-{4-[(3-tert-butyl-4-cyano-1,2-thiazol-5-yl)oxy]-2-chloro-5-methylphenyl}-N-ethyl-N-methylimidoformamide, (15.084) N-methyl-2-(1-{[5-methyl-3-(trifluoromethyl)-1H-pyrazol-1-yl]acetyl}piperidin-4-yl)-N-(1,2,3,4-tetrahydronaphthalin-1-yl)-1,3-thiazole-4-carboxamide, (15.085) N-methyl-2-(1-{[5-methyl-3-(trifluoromethyl)-1H-pyrazol-1-yl]acetyl}piperidin-4-yl)-N-[(1R)-1,2,3,4-tetrahydronaphthalin-1-yl]-1,3-thiazole-4-carboxamide, (15.086) N-methyl-2-(1-{[5-methyl-3-(trifluoromethyl)-1H-pyrazol-1-yl]acetyl}piperidin-4-yl)-N-[(1S)-1,2,3,4-tetrahydronaphthalin-1-yl]-1,3-thiazole-4-carboxamide, (15.087) {6-[({[(1-methyl-1H-tetrazol-5-yl)(phenyl)methylen]amino}oxy)methyl]pyridin-2-yl}carbamic acid pentyl ester, (15.088) phenazine-1-carboxylic acid, (15.089) quinolin-8-ol, (15.090) quinolin-8-ol sulphate (2:1), (15.091) {6-[({[(1-methyl-1H-tetrazol-5-yl)(phenyl)methylen]amino) oxy)methyl]pyridin-2-yl}carbamic acid tert-butyl ester, (15.092) (5-bromo-2-methoxy-4-methylpyridin-3-yl)(2,3,4-trimethoxy-6-methylphenyl)methanone, (15.093) N-[2-(4-{[3-(4-chlorophenyl)prop-2-yn-1-yl]oxy}-3-methoxyphenyl)ethyl]-N2-(methylsulfonyl)valinamide, (15.094) 4-oxo-4-[(2-phenylethyl)amino]butanoic acid, (15.095) (6-[({[(Z)-(1-methyl-1H-tetrazol-5-yl)(phenyl)methylen]amino}oxy)methyl]pyridin-2-yl}carbamic acid but-3-yn-1-yl ester, (15.096) 4-amino-5-fluoropyrimidin-2-ol (tautomeric form: 4-amino-5-fluoropyrimidin-2(1H)-one), (15.097) propyl 3,4,5-trihydroxybenzoate, (15.098) [3-(4-chloro-2-fluorophenyl)-5-(2,4-difluorophenyl)-1,2-oxazol-4-yl](pyridin-3-yl)methanol, (15.099) (S)-[3-(4-chloro-2-fluorophenyl)-5-(2,4-difluorophenyl)-1,2-oxazol-4-yl](pyridin-3-yl)methanol, (15.100) (R)-[3-(4-chloro-2-fluorophenyl)-5-(2,4-difluorophenyl)-1,2-oxazol-4-yl](pyridin-3-yl)methanol, (15.101) 2-fluoro-6-(trifluoromethyl)-N-(1,1,3-trimethyl-2,3-dihydro-1H-inden-4-yl)benzamide, (15.102) 2-(6-benzylpyridin-2-yl)quinazoline, (15.103) 2-[6-(3-fluoro-4-methoxyphenyl)-5-methylpyridin-2-yl]quinazoline, (15.104) 3-(4,4-difluoro-3,3-dimethyl-3,4-dihydroisoquinolin-1-yl)quinoline, (15.105) abscisic acid, (15.106) N'-[5-bromo-6-(2,3-dihydro-1H-inden-2-yloxy)-2-methylpyridin-3-yl]-N-ethyl-N-methylimidoformamide, (15.107) N'-{5-bromo-6-[1-(3,5-difluorophenyl)ethoxy]-2-methylpyridin-3-yl}-N-ethyl-N-methylimidoformamide, (15.108) N'-{5-bromo-6-[(1R)-1-(3,5-difluorophenyl)ethoxy]-2-methylpyridin-3-yl}-N-ethyl-N-methylimidoformamide, (15.109) N'-{5-bromo-6-[(1S)-1-(3,5-difluorophenyl)ethoxy]-2-methylpyridin-3-yl}-N-ethyl-N-methylimidoformamide, (15.110) N'-{5-bromo-6-[(cis-4-isopropylcyclohexyl)oxy]-2-methylpyridin-3-yl}-N-ethyl-N-methylimidoformamide, (15.111) N'-{5-bromo-6-[(trans-4-isopropylcyclohexyl)oxy]-2-methylpyridin-3-yl}-N-ethyl-N-methylimidoformamide, (15.112) N-cyclopropyl-3-(difluoromethyl)-5-fluoro-N-(2-isopropylbenzyl)-1-methyl-1H-pyrazole-4-carboxamide, (15.113) N-cyclopropyl-N-(2-cyclopropylbenzyl)-3-(difluoromethyl)-5-fluoro-1-methyl-1H-pyrazole-4-carboxamide, (15.114) N-(2-tert-butylbenzyl)-N-cyclopropyl-3-(difluoromethyl)-5-fluoro-1-methyl-1H-pyrazole-4-carboxamide, (15.115) N-(5-chloro-2-ethylbenzyl)-N-cyclopropyl-3-(difluoromethyl)-5-fluoro-1-methyl-1H-pyrazole-4-carboxamide, (15.116) N-(5-chloro-2-isopropylbenzyl)-N-cyclopropyl-3-(difluoromethyl)-5-fluoro-1-methyl-1H-pyrazole-4-carboxamide, (15.117) N-cyclopropyl-3-(difluoromethyl)-N-(2-ethyl-5-fluorobenzyl)-5-fluoro-1-methyl-1H-pyrazole-4-carboxamide, (15.118) N-cyclopropyl-3-(difluoromethyl)-5-fluoro-N-(5-fluoro-2-isopropylbenzyl)-1-methyl-1H-pyrazole-4-carboxamide, (15.119) N-cyclopropyl-N-(2-cyclopropyl-5-fluorobenzyl)-3-(difluoromethyl)-5-fluoro-1-methyl-1H-pyrazole-4-carboxamide, (15.120) N-(2-cyclopentyl-5-fluorobenzyl)-N-cyclopropyl-3-(difluoromethyl)-5-fluoro-1-methyl-1H-pyrazole-4-carboxamide, (15.121) N-cyclopropyl-3-(difluoromethyl)-5-fluoro-N-(2-fluoro-6-isopropylbenzyl)-1-methyl-1H-pyrazole-4-carboxamide, (15.122) N-cyclopropyl-3-(difluoromethyl)-N-(2-ethyl-5-methylbenzyl)-5-fluoro-1-methyl-1H-pyrazole-4-carboxamide, (15.123) N-cyclopropyl-3-(difluoromethyl)-5-fluoro-N-(2-isopropyl-5-methylbenzyl)-1-methyl-1H-pyrazole-4-carboxamide, (15.124) N-cyclopropyl-N-(2-cyclopropyl-5-methylbenzyl)-3-(difluoromethyl)-5-fluoro-1-methyl-1H-pyrazole-4-carboxamide, (15.125) N-(2-tert-butyl-5-methylbenzyl)-N-cyclopropyl-3-(difluoromethyl)-5- fluoro-1-methyl-1H-pyrazole-4-carboxamide, (15.126) N-[5-chloro-2-(trifluoromethyl)benzyl]-N-cyclopropyl-3-(difluoromethyl)-5-fluoro-1-methyl-1H-pyrazole-4-carboxamide, (15.127) N-cyclopropyl-3-(difluoromethyl)-5-fluoro-1-methyl-N-[5-methyl-2-(trifluoromethyl)benzyl]-1H-pyrazole-4-carboxamide, (15.128) N-[2-chloro-6-(trifluoromethyl)benzyl]-N-cyclopropyl-3-(difluoromethyl)-5-fluoro-1-methyl-1H-pyrazole-4-carboxamide, (15.129) N-[3-chloro-2-fluoro-6-(trifluoromethyl)benzyl]-N-cyclopropyl-3-(difluoromethyl)-5-fluoro-1-methyl-1H-pyrazole-4-carboxamide, (15.130) N-cyclopropyl-3-(difluoromethyl)-N-(2-ethyl-4,5-dimethylbenzyl)-5-fluoro-1-methyl-1H-pyrazole-4-carboxamide, (15.131) N-cyclopropyl-3-(difluoromethyl)-5-fluoro-N-(2-isopropylbenzyl)-1-methyl-1H-pyrazole-4-carbothioamide, (15.132) N'-(2,5-dimethyl-4-phenoxyphenyl)-N-ethyl-N-methylimidoformamide, (15.133) N'-{4-[(4,5-dichloro-1,3-thiazol-2-yl)oxy]-2,5-dimethylphenyl}-N-ethyl-N-methylimidoformamide, (15.134) N-(4-chloro-2,6-difluorophenyl)-4-(2-chloro-4-fluorophenyl)-1,3-dimethyl-1H-pyrazol-5-amine, (15.135) 9-fluoro-2,2-dimethyl-5-(quinolin-3-yl)-2,3-dihydro-1,4-benzoxazepine, (15.136) 2-{2-fluoro-6-[(8-fluoro-2-methylquinolin-3-yl)oxy]phenyl}propan-2-ol, (15.137) 2-{2-[(7,8-difluoro-2-methylquinolin-3-yl)oxy]-6-fluorophenyl}propan-2-ol, (15.138) 4-(2-chloro-4-fluorophenyl)-N-(2-fluorophenyl)-1,3-dimethyl-1H-pyrazol-5-amine, (15.139) 4-(2-chloro-4-fluorophenyl)-N-(2,6-difluorophenyl)-1,3-dimethyl-1H-pyrazol-5-amine, (15.140) 4-(2-chloro-4-fluorophenyl)-N-(2-chloro-6-fluorophenyl)-1,3-dimethyl-1H-pyrazol-5-amine, (15.141) 4-(2-bromo-4-fluorophenyl)-N-(2-chloro-6-fluorophenyl)-1,3-dimethyl-1H-pyrazol-5-amine, (15.142) N-(2-bromo-6-fluorophenyl)-4-(2-chloro-4-fluorophenyl)-1,3-dimethyl-1H-pyrazol-5-amine, (15.143) 4-(2-bromo-4-fluorophenyl)-N-(2-bromophenyl)-1,3-dimethyl-1H-pyrazol-5-amine, (15.144) 4-(2-bromo-4-fluorophenyl)-N-(2-bromo-6-fluorophenyl)-1,3-dimethyl-H-pyrazol-5-amine, (15.145) 4-(2-bromo-4-fluorophenyl)-N-(2-chlorophenyl)-1,3-dimethyl-1H-pyrazol-5-amine, (15.146) N-(2-bromophenyl)-4-(2-chloro-4-fluorophenyl)-1,3-dimethyl-1H-pyrazol-5-amine, (15.147) 4-(2-chloro-4-fluorophenyl)-N-(2-chlorophenyl)-1,3-dimethyl-1H-pyrazol-5-amine, (15.148) 4-(2-bromo-4-fluorophenyl)-N-(2,6-difluorophenyl)-1,3-dimethyl-1H-pyrazol-5-amine, (15.149) 4-(2-bromo-4-fluorophenyl)-N-(2-fluorophenyl)-1,3-dimethyl-1H-pyrazol-5-amine, (15.150) N'-(4-{3-[(difluoromethyl)sulfanyl]phenoxy}-2,5-dimethylphenyl)-N-ethyl-N-methylimidoformamide, (15.151) N'-(2,5-dimethyl-4-{3-[(1,1,2,2-tetrafluoroethyl)sulfanyl]phenoxy}phenyl)-N-ethyl-N-methylimidoformamide, (15.152) N'-(2,5-dimethyl-4-{3-[(2,2,2-trifluoroethyl)sulfanyl]phenoxy}phenyl)-N-ethyl-N-methylimidoformamide, (15.153) N'-(2,5-dimethyl-4-{3-[(2,2,3,3-tetrafluoropropyl)sulfanyl]phenoxy}phenyl)-N-ethyl-N-methylimidoformamide, (15.154) N'-(2,5-dimethyl-4-{3-[(pentafluoroethyl)sulfanyl]phenoxy}phenyl)-N-ethyl-N-methylimidoformamide, (15.155) N'-(4-{[3-(difluoromethoxy)phenyl]sulfanyl}-2,5-dimethylphenyl)-N-ethyl-N-methylimidoformamide, (15.156) N'-(2,5-dimethyl-4-{[3-(1,1,2,2-tetrafluoroethoxy)phenyl]sulfanyl}phenyl)-N-ethyl-N-methylimidoformamide, (15.157) N'-(2,5-dimethyl-4-{[3-(2,2,2-trifluoroethoxy)phenyl]sulfanyl}phenyl)-N-ethyl-N-methylimidoformamide, (15.158) N'-(2,5-dimethyl-4-{[3-(2,2,3,3-tetrafluoropropoxy)phenyl]sulfanyl}phenyl)-N-ethyl-N-methylimidoformamide, (15.159) N'-(2,5-dimethyl-4-{[3-(pentafluoroethoxy)phenyl]sulfanyl}phenyl)-N-ethyl-N-methylimidoformamide, (15.160) 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, (15.161) 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.162) 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, (15.163) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate, (15.164) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.165) 2-[3,5-bis(difluoromethyl)-1H-pyrazol-1-yl]-1-[4-(4-{(5S)-5-[2-(prop-2-yn-1-yloxy)phenyl]-4,5-dihydro-1,2-oxazol-3-yl}-1,3-thiazol-2-yl)piperidin-1-yl]ethanone, (15.166) 2-[3,5-bis(difluoromethyl)-1H-pyrazol-1-yl]-1-[4-(4-{(5R)-5-[2-(prop-2-yn-1-yloxy)phenyl]-4,5-dihydro-1,2-oxazol-3-yl}-1,3-thiazol-2-yl)piperidin-1-yl]ethanone, (15.167) 2-[3,5-bis(difluoromethyl)-1H-pyrazol-1-yl]-1-[4-(4-{(5S)-5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.168) 2-[3,5-bis(difluoromethyl)-1H-pyrazol-1-yl]-1-[4-(4-{(5R)-5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.169) 2-[3,5-bis(difluoromethyl)-1H-pyrazol-1-yl]-1-[4-(4-{(5S)-5-[2-chloro-6-(prop-2-yn-1-yloxy)phenyl]-4,5-dihydro-1,2-oxazol-3-yl}-1,3-thiazol-2-yl)piperidin-1-yl]ethanone, (15.170) 2-[3,5-bis(difluoromethyl)-1H-pyrazol-1-yl]-1-[4-(4-{(5R)-5-[2-chloro-6-(prop-2-yn-1-yloxy)phenyl]-4,5-dihydro-1,2-oxazol-3-yl})-1,3-thiazol-2-yl)piperidin-1-yl]ethanone, (15.171) 2-{((5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate, (15.172) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate, (15.173) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.174) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate.

Biological Pesticides as Mixing Components

The compounds of the formula (I) can be combined with biological pesticides.

Biological pesticides especially include bacteria, fungi, yeasts, plant extracts and products formed by microorganisms, including proteins and secondary metabolites.

Biological pesticides include bacteria such as spore-forming bacteria, root-colonizing bacteria and bacteria which act as biological insecticides, fungicides or nematicides.

Examples of such bacteria which are used or can be used as biological pesticides are:

*Bacillus amyloliquefaciens*, strain FZB42 (DSM 231179), or *Bacillus cereus*, especially *B. cereus* strain CNCM 1-1562 or *Bacillus firmus*, strain 1-1582 (Accession number CNCM 1-1582) or *Bacillus pumilus*, especially strain GB34 (Accession No. ATCC 700814) and strain QST2808 (Accession No. NRRL B-30087), or *Bacillus subtilis*, especially strain GB03 (Accession No. ATCC SD-1397), or *Bacillus subtilis* strain QST713 (Accession No. NRRL B-21661) or *Bacillus subtilis* strain OST 30002 (Accession No. NRRL B-50421) *Bacillus thuringiensis*, especially *B. thuringiensis* subspecies *israelensis* (serotype H-14), strain AM65-52 (Accession No. ATCC1276), or *B. thuringiensis* subsp. *aizawai*, especially strain ABTS-1857 (SD-1372), or *B. thuringiensis* subsp. *kurstaki* strain HD-1, or *B. thuringiensis* subsp. *tenebrionis* strain NB 176 (SD-5428), *Pasteuria penetrans, Pasteuria* spp. (*Rotylenchulus reniformis* nematode)-PR3 (Accession Number ATCC SD-5834), *Streptomyces microflavus* strain AQ6121 (=QRD 31.013, NRRL B-50550), *Streptomyces galbus* strain AQ 6047 (Accession Number NRRL 30232).

Examples of fungi and yeasts which are used or can be used as biological pesticides are:
*Beauveria bassiana*, in particular strain ATCC 74040, *Coniothyrium minitans*, in particular strain CON/M/91-8 (Accession No. DSM-9660), *Lecanicillium* spp, in particular strain HRO LEC12, *Lecanicillium lecanii* (formerly known as *Verticillium lecanii*), in particular strain KV01, *Metarhizium anisopliae*, in particular strain F52 (DSM3884/ATCC 90448), *Metschnikowia fructicola*, in particular strain NRRL Y-30752, *Paecilomyces fumosoroseus* (new: *Isaria fumosorosea*), in particular strain IFPC 200613, or strain Apopka 97 (Accession No. ATCC 20874), *Paecilomyces lilacinus*, in particular *P. lilacinus* strain 251 (AGAL 89/030550), *Talaromyces flavus*, in particular strain V117b, *Trichoderma atroviride*, in particular strain SC1 (Accession Number CBS 122089), *Trichoderma harzianum*, in particular *T. harzianum rifai* T39 (accession number CNCM 1-952).

Examples of viruses which are used or can be used as biological pesticides are:
*Adoxophyes orana* (summer fruit *tortrix*) granulosis virus (GV), *Cydia pomonella* (codling moth) granulosis virus (GV), *Helicoverpa armigera* (cotton bollworm) nuclear polyhedrosis virus (NPV), *Spodoptera exigua* (beet armyworm) mNPV, *Spodoptera frugiperda* (fall armyworm) mNPV, *Spodoptera littoralis* (African cotton leafworm) NPV.

Also included are bacteria and fungi which are added as 'inoculant' to plants or plant parts or plant organs and which, by virtue of their particular properties, promote plant growth and plant health. Examples include:
*Agrobacterium* spp., *Azorhizobium caulinodans, Azospirillum* spp., *Azotobacter* spp., *Bradyrhizobium* spp., *Burkholderia* spp., especially *Burkholderia cepacia* (formerly known as *Pseudomonas cepacia*), *Gigaspora* spp., or *Gigaspora monosporum, Glomus* spp., *Laccaria* spp., *Lactobacillus buchneri, Paraglomus* spp., *Pisolithus tinctorus, Pseudomonas* spp., *Rhizobium* spp., especially *Rhizobium trifolii, Rhizopogon* spp., *Scleroderma* spp., *Suillus* spp., *Streptomyces* spp.

Examples of plant extracts and products formed by microorganisms, including proteins and secondary metabolites, which are used or can be used as biological pesticides are:
*Allium sativum, Artemisia absinthium*, azadirachtin, Biokeeper WP, *Cassia nigricans, Celastrus angulatus, Chenopodium anthelminticum*, chitin, Armour-Zen, *Dryopteris filix-mas, Equisetum arvense*, Fortune Aza, Fungastop, Heads Up (*Chenopodium quinoa* saponin extract), pyrethrum/pyrethrins, *Quassia amara, Quercus*, Quillaja, Regalia, "Requiem™ Insecticide", rotenone, ryania/ryanodine, *Symphytum officinale, Tanacetum vulgare*, thymol, Triact 70, TriCon, *Tropaeulum majus, Urtica dioica*, Veratrin, Viscum album, Brassicaceae extract, especially oilseed rape powder or mustard powder.

Safeners as Mixing Components

The compounds of the formula (I) can be combined with safeners, for example benoxacor, cloquintocet (-mexyl), cyometrinil, cyprosulfamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, 2-methoxy-N-({4-[(methylcarbamoyl)amino]phenyl}sulfonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Plants and Plant Parts

All plants and plant parts can be treated in accordance with the invention. Plants are understood here to mean all plants and populations of plants, such as desirable and undesirable wild plants or crop plants (including naturally occurring crop plants), for example cereals (wheat, rice, triticale, barley, rye, oats), maize, soya bean, potato, sugar beet, sugar cane, tomatoes, peas and other vegetable species, cotton, tobacco, oilseed rape, and also fruit plants (with the fruits apples, pears, citrus fruits and grapes). Crop plants may be plants which can be obtained by conventional breeding and optimization methods or by biotechnological and genetic engineering methods or combinations of these methods, including the transgenic plants and including the plant cultivars which are protectable or non-protectable by plant breeders' rights. Plant parts shall be understood to mean all parts and organs of the plants above and below ground, such as shoot, leaf, flower and root, examples given being leaves, needles, stalks, stems, flowers, fruit bodies, fruits and seeds, and also roots, tubers and rhizomes. Plant parts also include harvested material and vegetative and generative propagation material, for example cuttings, tubers, rhizomes, slips and seeds.

Treatment according to the invention of the plants and plant parts with the compounds of the formula (I) is carried out directly or by allowing the compounds to act on their surroundings, habitat or storage space by the customary treatment methods, for example by immersion, spraying, evaporation, fogging, scattering, painting on, injection and, in the case of propagation material, in particular in the case of seeds, also by applying one or more coats.

As already mentioned above, it is possible to treat all plants and parts thereof in accordance with the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. Particular preference is given in accordance with the invention to treating plants of the respective commercially customary plant cultivars or those that are in use. Plant cultivars are understood to mean plants having new properties ("traits") which have been grown by conventional breeding, by mutagenesis or by recombinant DNA techniques. They may be cultivars, varieties, biotypes or genotypes.

Transgenic Plants, Seed Treatment and Integration Events

The preferred transgenic plants or plant cultivars (those obtained by genetic engineering) which are to be treated in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher harvest yields, higher quality and/or higher nutritional value of the harvested products, better capability for storage and/or processability of the harvested products. Further and particularly emphasized examples of such properties are increased resistance of the plants against animal and microbial pests, such as insects, arachnids, nematodes, mites, slugs and snails, owing, for example, to toxins formed in the plants, in particular those formed in the plants by the genetic material from *Bacillus thuringiensis* (for example by the genes CryIA(a), CryIA(b), CryIA(c), CrylllA, CryIIA, CryIIIB2, Cry9c, Cry2Ab, Cry3Bb and CryIF and also combinations thereof), and also increased resistance of the plants against phytopathogenic fungi, bacteria and/or viruses caused, for example, by systemic acquired resistance (SAR), systemin, phytoalexins, elicitors and resistance genes and correspondingly expressed proteins and toxins, and also increased tolerance of the plants to certain herbicidally active ingredients, for example imidazolinones, sulfonylureas, glyphosates or phosphinothricin (for example the "PAT" gene). The genes which impart the desired properties ("traits") in question may also be present in combinations with one another in the transgenic plants. Examples of transgenic plants include the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (with the fruits apples, pears, citrus fruits and grapes), particular emphasis being given to maize, soya beans, wheat, rice, potatoes, cotton, sugar cane, tobacco and oilseed rape. Properties ("traits") which are particularly emphasized are the increased resistance of the plants to insects, arachnids, nematodes and slugs and snails.

Crop Protection—Types of Treatment

The plants and plant parts are treated with the compounds of the formula (I) directly or by action on their surroundings, habitat or storage space using customary treatment methods, for example by dipping, spraying, atomizing, irrigating, evaporating, dusting, fogging, broadcasting, foaming, painting, spreading-on, injecting, watering (drenching), drip irrigating and, in the case of propagation material, in particular in the case of seed, additionally by dry seed treatment, liquid seed treatment, slurry treatment, by incrusting, by coating with one or more coats, etc. It is furthermore possible to apply the compounds of the formula (I) by the ultra-low volume method or to inject the application form or the compound of the formula (I) itself into the soil.

A preferred direct treatment of the plants is foliar application, i.e. compounds of the formula (I) are applied to the foliage, where treatment frequency and the application rate should be adjusted according to the level of infestation with the pest in question.

In the case of systemically active compounds, the compounds of the formula (I) also access the plants via the root system. The plants are then treated by the action of the compounds of the formula (I) on the habitat of the plant. This can be accomplished, for example, by drenching, or by mixing into the soil or the nutrient solution, meaning that the locus of the plant (e.g. soil or hydroponic systems) is impregnated with a liquid form of the compounds of the formula (I), or by soil application, meaning that the compounds of the formula (I) are introduced in solid form (e.g. in the form of granules) into the locus of the plants. In the case of paddy rice crops, this can also be accomplished by metering the compound of the formula (I) in a solid application form (for example as granules) into a flooded paddy field.

Seed Treatment

The control of animal pests by the treatment of the seed of plants has long been known and is the subject of constant improvements. Nevertheless, the treatment of seed entails a series of problems which cannot always be solved in a satisfactory manner. Thus, it is desirable to develop methods for protecting the seed and the germinating plant which dispense with, or at least reduce considerably, the additional application of pesticides during storage, after sowing or after emergence of the plants. It is additionally desirable to optimize the amount of active ingredient used so as to provide optimum protection for the seed and the germinating plant from attack by animal pests, but without damage to the plant itself by the active ingredient used. In particular, methods for the treatment of seed should also take account of the intrinsic insecticidal or nematicidal properties of pest-resistant or -tolerant transgenic plants in order to achieve optimal protection of the seed and the germinating plant with a minimum expenditure on pesticides.

The present invention therefore in particular also relates to a method for the protection of seed and germinating plants from attack by pests, by treating the seed with one of the compounds of the formula (I). The method according to the invention for protecting seed and germinating plants against attack by pests further comprises a method in which the seed is treated simultaneously in one operation or sequentially with a compound of the formula (I) and a mixing component. It further also comprises a method where the seed is treated at different times with a compound of the formula (I) and a mixing component.

The invention also relates to the use of the compounds of the formula (I) for the treatment of seed for protecting the seed and the resulting plant from animal pests.

The invention further relates to seed which has been treated with a compound of the formula (I) for protection from animal pests. The invention also relates to seed which has been treated simultaneously with a compound of the formula (I) and a mixing component. The invention further relates to seed which has been treated at different times with a compound of the formula (I) and a mixing component. In the case of seed which has been treated at different times with a compound of the formula (I) and a mixing component, the individual substances may be present on the seed in different layers. In this case, the layers comprising a compound of the formula (I) and a mixing component may optionally be separated by an intermediate layer. The invention also relates to seed in which a compound of the formula (I) and a mixing component have been applied as part of a coating or as a further layer or further layers in addition to a coating.

The invention further relates to seed which, after the treatment with a compound of the formula (I), is subjected to a film-coating process to prevent dust abrasion on the seed.

One of the advantages encountered with a systemically acting compound of the formula (I) is the fact that, by treating the seed, not only the seed itself but also the plants resulting therefrom are, after emergence, protected against animal pests. In this way, the immediate treatment of the crop at the time of sowing or shortly thereafter can be dispensed with.

A further advantage is that the treatment of the seed with a compound of the formula (I) can enhance germination and emergence of the treated seed.

It is likewise considered to be advantageous that compounds of the formula (I) can especially also be used for transgenic seed.

Furthermore, compounds of the formula (I) can be employed in combination with compositions of signalling technology, leading to better colonization by symbionts such as, for example, *rhizobia*, mycorrhizae and/or endophytic bacteria or fungi, and/or to optimized nitrogen fixation.

The compounds of the formula (I) are suitable for protection of seed of any plant variety which is used in agriculture, in the greenhouse, in forests or in horticulture. More particularly, this includes seed of cereals (for example wheat, barley, rye, millet and oats), maize, cotton, soya beans, rice, potatoes, sunflowers, coffee, tobacco, canola, oilseed rape, beet (for example sugar beet and fodder beet), peanuts, vegetables (for example tomatoes, cucumbers, beans, cruciferous vegetables, onions and lettuce), fruit plants, lawns and ornamental plants. Of particular significance is the treatment of the seed of cereals (such as wheat, barley, rye and oats), maize, soya beans, cotton, canola, oilseed rape and rice.

As already mentioned above, the treatment of transgenic seed with a compound of the formula (I) is also of particular importance. This involves the seed of plants which generally contain at least one heterologous gene which controls the expression of a polypeptide having insecticidal and/or nematicidal properties in particular. The heterologous genes in transgenic seed may originate in this case from microorganisms such as *Bacillus, Rhizobium, Pseudomonas, Serratia, Trichoderma, Clavibacter, Glomus* or *Gliocladium*. The present invention is particularly suitable for the treatment of transgenic seed containing at least one heterologous gene originating from *Bacillus* sp. The heterologous gene is more preferably derived from *Bacillus thuringiensis*.

In the context of the present invention, the compound of the formula (I) is applied to the seed. The seed is preferably treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content which allows storage. Alternatively, it is also possible to use seed which, after drying, has been treated with, for example, water and then dried again, for example priming. In the case of rice seed, it is also possible to use seed which has been pre-swollen in water up to a certain stage (pigeon breast stage) for example, which leads to improved germination and more uniform emergence.

When treating the seed, care must generally be taken that the amount of the compound of the formula (I) applied to the seed and/or the amount of further additives is chosen in such a way that the germination of the seed is not adversely affected, or that the resulting plant is not damaged. This has to be ensured particularly in the case of active ingredients which can exhibit phytotoxic effects at certain application rates.

In general, the compounds of the formula (I) are applied to the seed in the form of a suitable formulation. Suitable formulations and processes for seed treatment are known to the person skilled in the art.

The compounds of the formula (I) can be converted to the customary seed-dressing formulations, such as solutions, emulsions, suspensions, powders, foams, slurries or other coating compositions for seed, and also ULV formulations.

These formulations are prepared in a known manner, by mixing compounds of the formula (I) with customary additives such as, for example, customary extenders and also solvents or diluents, dyes, wetting agents, dispersants, emulsifiers, antifoams, preservatives, secondary thickeners, adhesives, gibberellins and also water.

Dyes which may be present in the seed-dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed-dressing formulations usable in accordance with the invention are all substances which promote wetting and which are customary for the formulation of active agrochemical ingredients. Alkyl naphthalenesulphonates, such as diisopropyl or diisobutyl naphthalenesulphonates, can be used with preference.

Suitable dispersants and/or emulsifiers which may be present in the seed-dressing formulations usable in accordance with the invention are all nonionic, anionic and cationic dispersants customary for the formulation of active agrochemical ingredients. Nonionic or anionic dispersants or mixtures of nonionic or anionic dispersants can be used with preference. Suitable nonionic dispersants especially include ethylene oxide/propylene oxide block polymers, alkylphenol polyglycol ethers and tristyrylphenol polyglycol ethers, and the phosphated or sulphated derivatives thereof. Suitable anionic dispersants are especially lignosulphonates, polyacrylic acid salts and arylsulphonate-formaldehyde condensates.

Antifoams which may be present in the seed-dressing formulations usable in accordance with the invention are all foam-inhibiting substances customary for the formulation of active agrochemical ingredients. Silicone antifoams and magnesium stearate can be used with preference.

Preservatives which may be present in the seed-dressing formulations usable in accordance with the invention are all substances usable for such purposes in agrochemical compositions. Examples include dichlorophene and benzyl alcohol hemiformal.

Secondary thickeners which may be present in the seed-dressing formulations usable in accordance with the invention are all substances which can be used for such purposes in agrochemical compositions. Preferred examples include cellulose derivatives, acrylic acid derivatives, xanthan, modified clays and finely divided silica.

Useful stickers which may be present in the seed-dressing formulations usable in accordance with the invention are all customary binders usable in seed-dressing products. Preferred examples include polyvinylpyrrolidone, polyvinyl acetate, polyvinyl alcohol and tylose.

Gibberellins which may be present in the seed-dressing formulations usable in accordance with the invention are preferably the gibberellins A1, A3 (=gibberellic acid), A4 and A7; particular preference is given to using gibberellic acid. The gibberellins are known (cf. R. Wegler "Chemie der Pflanzenschutz-und Schädlingsbekämpfungsmittel", vol. 2, Springer Verlag, 1970, pp. 401-412).

The seed-dressing formulations usable in accordance with the invention can be used to treat a wide variety of different kinds of seed, either directly or after prior dilution with water. For instance, the concentrates or the preparations obtainable therefrom by dilution with water can be used to dress the seed of cereals, such as wheat, barley, rye, oats and triticale, and also the seed of maize, rice, oilseed rape, peas, beans, cotton, sunflowers, soya beans and beets, or else a wide variety of different vegetable seed. The seed-dressing formulations usable in accordance with the invention, or the dilute use forms thereof, can also be used to dress seed of transgenic plants.

For the treatment of seed with the seed-dressing formulations usable in accordance with the invention, or use forms prepared therefrom, all mixing units usable customarily for the seed dressing are useful. Specifically, the procedure in seed dressing is to place the seed into a mixer in batchwise or continuous operation, to add the particular desired amount of seed-dressing formulations, either as such or after prior dilution with water, and to mix until the formulation is distributed homogeneously on the seed. If appropriate, this is followed by a drying operation.

The application rate of the seed dressing formulations usable in accordance with the invention can be varied within a relatively wide range. It is guided by the particular content of the compounds of the formula (I) in the formulations and by the seed. The application rates of the compound of the formula (I) are generally between 0.001 and 50 g per kilogram of seed, preferably between 0.01 and 15 g per kilogram of seed.

Animal Health

In the animal health field, i.e. the field of veterinary medicine, the compounds of the formula (I) are active against animal parasites, in particular ectoparasites or endoparasites. The term "endoparasites" includes especially helminths and protozoa, such as coccidia. Ectoparasites are typically and preferably arthropods, especially insects and acarids.

In the field of veterinary medicine, the compounds of the formula (I) having favourable endotherm toxicity are suitable for controlling parasites which occur in animal breeding and animal husbandry in livestock, breeding animals, zoo animals, laboratory animals, experimental animals and domestic animals. They are active against all or specific stages of development of the parasites.

Agricultural livestock include, for example, mammals such as sheep, goats, horses, donkeys, camels, buffalo, rabbits, reindeer, fallow deer, and particularly cattle and pigs; poultry such as turkeys, ducks, geese, and particularly chickens; fish and crustaceans, for example in aquaculture, and also insects such as bees.

Domestic animals include, for example, mammals, such as hamsters, guinea pigs, rats, mice, chinchillas, ferrets, and particularly dogs, cats, caged birds, reptiles, amphibians and aquarium fish.

In a preferred embodiment, the compounds of the formula (I) are administered to mammals.

In another preferred embodiment, the compounds of the formula (I) are administered to birds, namely caged birds and particularly poultry.

Use of the compounds of the formula (I) for the control of animal parasites is intended to reduce or prevent illness, cases of death and reductions in performance (in the case of meat, milk, wool, hides, eggs, honey and the like), such that more economical and simpler animal husbandry is enabled and better animal well-being is achievable.

In relation to the field of animal health, the term "control" or "controlling" means that the compounds of the formula (I) are effective in reducing the incidence of the particular parasite in an animal infected with such parasites to an innocuous degree. More specifically, "controlling" in the present context means that the compound of the formula (I) can kill the respective parasite, inhibit its growth, or inhibit its proliferation.

Arthropods include:

from the order Anoplurida, for example *Haematopinus* spp., *Linognathus* spp., *Pediculus* spp., *Phtirus* spp., *Solenopotes* spp.; from the order Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; from the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; from the order Siphonapterida, for example *Pulex* spp., *Ctenocephalides* spp., *Tunga* spp., *Xenopsylla* spp., *Ceratophyllus* spp.;

from the order Heteropterida, for example *Cimex* spp., *Triatoma* spp., *Rhodnius* spp., *Panstrongylus* spp.; and also nuisance and hygiene pests from the order Blattarida.

Arthropods further include:

from the subclass Acari (Acarina) and the order Metastigmata, for example from the family Argasidae like *Argas* spp., *Ornithodorus* spp., *Otobius* spp., from the family Ixodidae like *Ixodes* spp., *Amblyomma* spp., *Rhipicephalus* (*Boophilus*) spp., *Dermacentor* spp., *Haemophysalis* spp., *Hyalomma* spp., *Rhipicephalus* spp. (the original genus of multi-host ticks); from the order Mesostigmata like *Dermanyssus* spp., *Ornithonyssus* spp., *Pneumonyssus* spp., *Raillietia* spp., *Pneumonyssus* spp., *Sternostoma* spp., *Varroa* spp., *Acarapis* spp.; from the order Actinedida (Prostigmata), for example *Acarapis* spp., *Cheyletiella* spp., *Ornithocheyletia* spp., *Myobia* spp., *Psorergates* spp., *Demodex* spp., *Trombicula* spp., *Neotrombiculla* spp., *Listrophorus* spp.; and from the order Acaridida (Astigmata), for example *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

Parasitic protozoa include:

Mastigophora (*Flagellata*), for example Trypanosomatidae, for example *Trypanosoma b. brucei, T.b. gambiense, T.b. rhodesiense, T. congolense, T. cruzi, T. evansi, T. equinum, T. lewisi, T. percae, T. simiae, T. vivax, Leishmania brasiliensis, L. donovani, L. tropica,* for example Trichomonadidae, for example *Giardia lamblia, G. canis;*

Sarcomastigophora (Rhizopoda) such as Entamoebidae, for example *Entamoeba histolytica,* Hartmanellidae, for example *Acanthamoeba* sp., *Harmanella* sp.;

Apicomplexa (Sporozoa) such as Eimeridae, for example *Eimeria acervulina, E. adenoides, E. alabamensis, E. anatis, E. anserina, E. arloingi, E. ashata, E. auburnensis, E. bovis, E. brunetti, E. canis, E. chinchillae, E. clupearum, E. columbae, E. contorta, E. crandalis, E. debliecki, E. dispersa, E. ellipsoidales, E. falciformis, E. faurei, E. flavescens, E. gallopavonis, E. hagani, E. intestinalis, E. iroquoina, E. irresidua, E. labbeana, E. leucarti, E. magna, E. maxima, E. media, E. meleagridis, E. meleagrimitis, E. mitis, E. necatrix, E. ninakohlyakimovae, E. ovis, E. parva,*

*E. pavonis, E. perforans, E. phasani, E. piriformis, E. praecox, E. residua, E. scabra, E.* spec., *E. stiedai, E. suis, E. tenella, E. truncata, E. truttae, E. zuernii, Globidium* spec., *Isospora belli, I. canis, I. felis, I. ohioensis, I. rivolta, I.* spec., *I. suis, Cystisospora* spec., *Cryptosporidium* spec., in particular *C. parvum*; such as Toxoplasmadidae, for example *Toxoplasma gondii, Hammondia heydornii, Neospora caninum, Besnoitia besnoitii*; such as Sarcocystidae, for example *Sarcocystis bovicanis, S. bovihominis, S. ovicanis, S. ovifelis, S. neurona, S.* spec., *S. suihominis*, such as Leucozoidae, for example *Leucozytozoon simondi*, such as Plasmodiidae, for example *Plasmodium berghei, P. falciparum, P. malariae, P. ovale, P. vivax, P.* spec., such as Piroplasmea, for example *Babesia argentina, B. bovis, B. canis, B.* spec., *Theileria parva, Theileria* spec., such as Adeleina, for example *Hepatozoon canis, H.* spec.

Pathogenic endoparasites which are helminths include Platyhelmintha (e.g. Monogenea, cestodes and trematodes), nematodes, Acanthocephala, and Pentastoma. These include:

Monogenea: for example: *Gyrodactylus* spp., *Dactylogyrus* spp., *Polystoma* spp.;

Cestodes: from the order of Pseudophyllidea, for example: *Diphyllobothrium* spp., *Spirometra* spp., *Schistocephalus* spp., *Ligula* spp., *Bothridium* spp., *Diphlogonoporus* spp.; from the order Cyclophyllida, for example: *Mesocestoides* spp., *Anoplocephala* spp., *Paranoplocephala* spp., *Moniezia* spp., *Thysanosoma* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diorchis* spp., *Dipylidium* spp., *Joyeuxiella* spp., *Diplopylidium* spp.

Trematodes: from the class of Digenea, for example: *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fascioloides* spp., *Fasciolopsis* spp., *Cyclocoelum* spp., *Typhlocoelum* spp., *Paramphistomum* spp., *Calicophoron* spp., *Cotylophoron* spp., *Gigantocotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp., *Metorchis* spp., *Heterophyes* spp., *Metagonimus* spp.;

Nematodes: Trichinellida, for example: *Trichuris* spp., *Capillaria* spp., *Paracapillaria* spp., *Eucoleus* spp., *Trichomosoides* spp., *Trichinella* spp.;

from the order Tylenchida, for example: *Micronema* spp., *Strongyloides* spp.;

from the order Rhabditida, for example: *Strongylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Ancylostoma* spp., *Uncinaria* spp., *Necator* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp., *Parelaphostrongylus* spp., *Crenosoma* spp., *Paracrenosoma* spp., *Oslerus* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Teladorsagia* spp., *Marshallagia* spp., *Cooperia* spp., *Nippostrongylus* spp., *Heligmosomoides* spp., *Nematodirus* spp., *Hyostrongylus* spp., *Obeliscoides* spp., *Amidostomum* spp., *Ollulanus* spp.;

from the order Spirurida, for example: *Oxyuris* spp., *Enterobius* spp., *Passalurus* spp., *Syphacia* spp., *Aspiculuris* spp., *Heterakis* spp.; *Ascaris* spp., *Toxascaris* spp., *Toxocara* spp., *Baylisascaris* spp., *Parascaris* spp., *Anisakis* spp., *Ascaridia* spp.; *Gnathostoma* spp., *Physaloptera* spp., *Thelazia* spp., *Gongylonema* spp., *Habronema* spp., *Parabronema* spp., *Draschia* spp., *Dracunculus* spp.; *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp., *Spirocerca* spp.;

Acanthocephala: from the order of Oligacanthorhynchida, for example: *Macracanthorhynchus* spp., *Prosthenorchis* spp.; from the order Polymorphida for example: *Filicollis* spp.; from the order Moniliformida for example: *Moniliformis* spp.;

from the order Echinorhynchida, for example *Acanthocephalus* spp., *Echinorhynchus* spp., *Leptorhynchoides* spp.;

Pentastoma: from the order Porocephalida, for example *Linguatula* spp.

In the veterinary field and in animal husbandry, the compounds of the formula (I) are administered by methods generally known in the art, such as via the enteral, parenteral, dermal or nasal route in the form of suitable preparations. Administration may be prophylactic or therapeutic.

Thus, one embodiment of the present invention refers to the use of a compound of the formula (I) as a medicament.

A further aspect refers to the use of a compound of the formula (I) as an antiendoparasitic agent, in particular a helminthicidal agent or antiprotozoic agent. Compounds of the formula (I) are suitable for use as an antiendoparasitic agent, especially as a helminthicidal agent or antiprotozoic agent, for example in animal breeding, in animal husbandry, in animal houses and in the hygiene sector.

A further aspect in turn relates to the use of a compound of the formula (I) as an antiectoparasitic agent, in particular an arthropodicide such as an insecticide or an acaricide. A further aspect relates to the use of a compound of the formula (I) as an antiectoparasitic agent, in particular an arthropodicide such as an insecticide or an acaricide, for example in animal husbandry, in animal breeding, in animal houses or in the hygiene sector.

Anthelmintic Mixing Components

The following anthelmintic mixing components may be mentioned by way of example:

anthelmintically active compounds including trematicidally and cestocidally active compounds:

from the class of the macrocyclic lactones, for example: abamectin, doramectin, emamectin, eprinomectin, ivermectin, milbemycin, moxidectin, nemadectin, selamectin;

from the class of the benzimidazoles and probenzimidazoles, for example: albendazole, albendazole-sulphoxide, cambendazole, cyclobendazole, febantel, fenbendazole, flubendazole, mebendazole, netobimin, oxfendazole, oxibendazole, parbendazole, thiabendazole, thiophanate, triclabendazole;

from the class of the cyclooctadepsipeptides, for example: emodepside, PF1022;

from the class of the aminoacetonitrile derivatives, for example: monepantel;

from the class of the tetrahydropyrimidines, for example: morantel, pyrantel, oxantel;

from the class of the imidazothiazoles, for example: butamisole, levamisole, tetramisole;
from the class of the salicylanilides, for example: bromoxanide, brotianide, clioxanide, closantel, niclosamide, oxyclozanide, rafoxanide, tribromsalan;
from the class of the paraherquamides, for example: derquantel, paraherquamide;
from the class of the aminophenylamidines, for example: amidantel, deacylated amidantel (dAMD), tribendimidine;
from the class of the organophosphates, for example: coumaphos, crufomate, dichlorvos, haloxone, naphthalofos, trichlorfon;
from the class of the substituted phenols, for example: bithionol, disophenol, hexachlorophene, niclofolan, meniclopholan, nitroxynil;
from the class of the piperazinones, for example: praziquantel, epsiprantel;
from various other classes, for example: amoscanate, bephenium, bunamidine, clonazepam, clorsulon, diamfenetid, dichlorophen, diethylcarbamazine, emetine, hetolin, hycanthone, lucanthone, Miracil, mirasan, niclosamide, niridazole, nitroxynil, nitroscanate, oltipraz, omphalotin, oxamniquin, paromomycin, piperazine, resorantel.

Vector Control

The compounds of the formula (I) can also be used in vector control. In the context of the present invention, a vector is an arthropod, especially an insect or arachnid, capable of transmitting pathogens, for example viruses, worms, single-cell organisms and bacteria, from a reservoir (plant, animal, human, etc.) to a host. The pathogens can be transmitted either mechanically (for example trachoma by non-stinging flies) to a host or after injection (for example malaria parasites by mosquitoes) into a host.

Examples of vectors and the diseases or pathogens they transmit are:
1) Mosquitoes
   *Anopheles*: malaria, filariasis;
   *Culex*: Japanese encephalitis, filariasis, other viral diseases, transmission of worms;
   *Aedes*: yellow fever, dengue fever, filariasis, other viral diseases;
   Simuliidae: transmission of worms, in particular *Onchocerca volvulus*;
2) Lice: skin infections, epidemic typhus;
3) Fleas: plague, endemic typhus;
4) Flies: sleeping sickness (trypanosomiasis); cholera, other bacterial diseases;
5) Mites: acariosis, epidemic typhus, rickettsialpox, tularaemia, Saint Louis encephalitis, tick-borne encephalitis (TBE), Crimean-Congo haemorrhagic fever, borreliosis;
6) Ticks: borellioses such as *Borrelia duttoni*, tick-borne encephalitis, Q fever (*Coxiella burnetii*), babesioses (*Babesia canis canis*).

Examples of vectors in the context of the present invention are insects, such as aphids, flies, leafhoppers or *thrips*, which can transmit plant viruses to plants. Other vectors capable of transmitting plant viruses are spider mites, lice, beetles and nematodes.

Further examples of vectors in the context of the present invention are insects and arachnids such as mosquitoes, especially of the genera *Aedes, Anopheles*, for example *A. gambiae, A. arabiensis, A. funestus, A. dirus* (malaria) and *Culex*, lice, fleas, flies, mites and ticks, which can transmit pathogens to animals and/or humans.

Vector control is also possible if the compounds of the formula (I) are resistance-breaking.

Compounds of the formula (I) are suitable for use in the prevention of diseases and/or pathogens transmitted by vectors. Thus, a further aspect of the present invention is the use of compounds of the formula (I) for vector control, for example in agriculture, in horticulture, in forests, in gardens and in leisure facilities, and also in the protection of materials and stored products.

Protection of Industrial Materials

The compounds of the formula (I) are suitable for protecting industrial materials against attack or destruction by insects, for example from the orders Coleoptera, Hymenoptera, Isoptera, Lepidoptera, Psocoptera and Zygentoma.

Industrial materials in the present context are understood to mean inanimate materials, such as preferably plastics, adhesives, sizes, papers and cards, leather, wood, processed wood products and coating compositions. The use of the invention for protection of wood is particularly preferred.

In a further embodiment, the compounds of the formula (I) are used together with at least one further insecticide and/or at least one fungicide.

In a further embodiment, the compounds of the formula (I) are present as a ready-to-use pesticide, i.e. it can be applied to the material in question without further modifications. Suitable further insecticides or fungicides are in particular those mentioned above.

Surprisingly, it has also been found that the compounds of the formula (I) can be employed for protecting objects which come into contact with saltwater or brackish water, in particular hulls, screens, nets, buildings, moorings and signalling systems, against fouling. It is equally possible to use the compounds of the formula (I), alone or in combinations with other active ingredients, as antifouling agents.

Control of Animal Pests in the Hygiene Sector

The compounds of the formula (I) are suitable for controlling animal pests in the hygiene sector. More particularly, the invention can be used in the domestic protection sector, in the hygiene protection sector and in the protection of stored products, particularly for control of insects, arachnids and mites encountered in enclosed spaces, for example dwellings, factory halls, offices, vehicle cabins. For controlling animal pests, the compounds of the formula (I) are used alone or in combination with other active ingredients and/or auxiliaries. They are preferably used in domestic insecticide products. The compounds of the formula (I) are effective against sensitive and resistant species, and against all developmental stages.

These pests include, for example, pests from the class Arachnida, from the orders Scorpiones, Araneae and Opiliones, from the classes Chilopoda and Diplopoda, from the class Insecta the order Blattodea, from the orders Coleoptera, Dermaptera, Diptera, Heteroptera, Hymenoptera, Isoptera, Lepidoptera, Phthiraptera, Psocoptera, Saltatoria or Orthoptera, Siphonaptera and Zygentoma and from the class Malacostraca the order Isopoda.

Application is carried out, for example, in aerosols, unpressurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or bait stations.

Intermediates

One aspect of the present invention relates to intermediates of the formula (II)

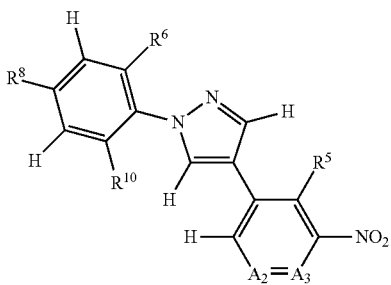

(II)

where

A$_2$, A$_3$, R$^5$, R$^6$, R$^8$ and R$^{10}$ have the definitions specified herein. In a preferred embodiment, A$_2$, A$_3$, R$^5$, R$^6$, R$^8$ and R$^{10}$ have the definitions as described above and also for compounds of the formula (I').

A further aspect of the present invention relates to intermediates of the formula (III),

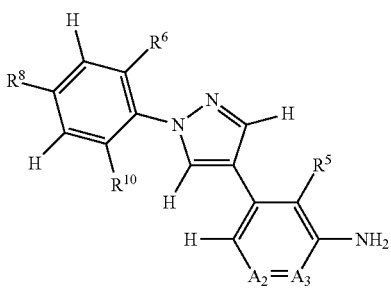

(III)

where

A$_2$, A$_3$, R$^5$, R$^6$, R$^8$ and R$^{10}$ have the definitions specified herein. In a preferred embodiment, A$_2$, A$_3$, R$^5$, R$^6$, R$^8$ and R$^{10}$ have the definitions as described above and also for compounds of the formula (I').

Preparation Methods

Compounds according to the invention of the general structure (Ia) may be prepared analogously to the peptide coupling methods known from the literature from the corresponding anilines or azinylamines (III) reacted with (VII-a) or (VII-b) [WO 2010/051926; WO 2010/133312].

The intermediates of the general structure (II) and (III) may be prepared by methods known from the literature by means of palladium-catalyzed reactions of the reaction partners (IV) and (V-a, V-b) or (VI-a, VI-b) [WO 2005/040110; WO 2009/089508]. The appropriate boronic acids (V-a, VI-a) or boron pinacolates (V-b, VI-b) are commercially available. It is possible to prepare the halopyrazole (IV) analogously to DE3509567.

Alternatively, the anilines or azinylamines (III) may be prepared from the corresponding nitro precursors (II) by reduction [WO 2012/080376].

Inventive compounds of the general structure (I-b) can be produced by alkylation reactions, which are sufficiently well known to those skilled in the art, of amides of the structure (I-a) with alkylating reagents (VIII), preferably in the presence of basic reaction auxiliaries.

Inventive compounds of the general structure (I-c) can be prepared in analogy to thionating processes known from the literature from compounds of the general structure (I-a) [WO 2012/056372; WO 2003/066050].

Reaction Scheme 1

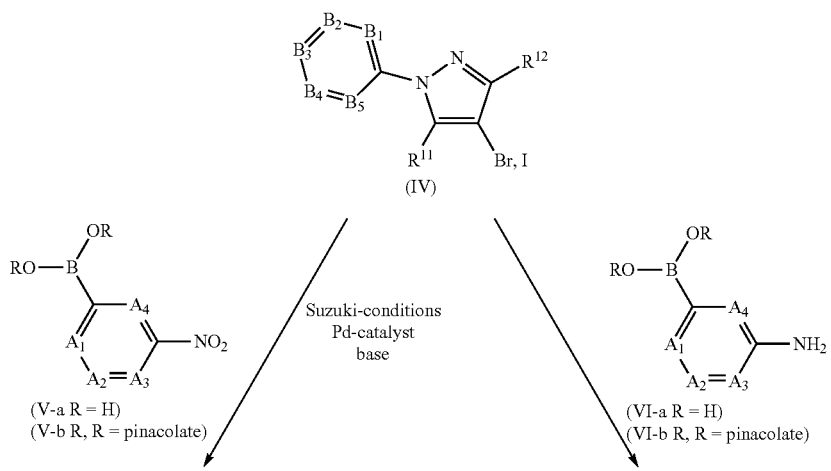

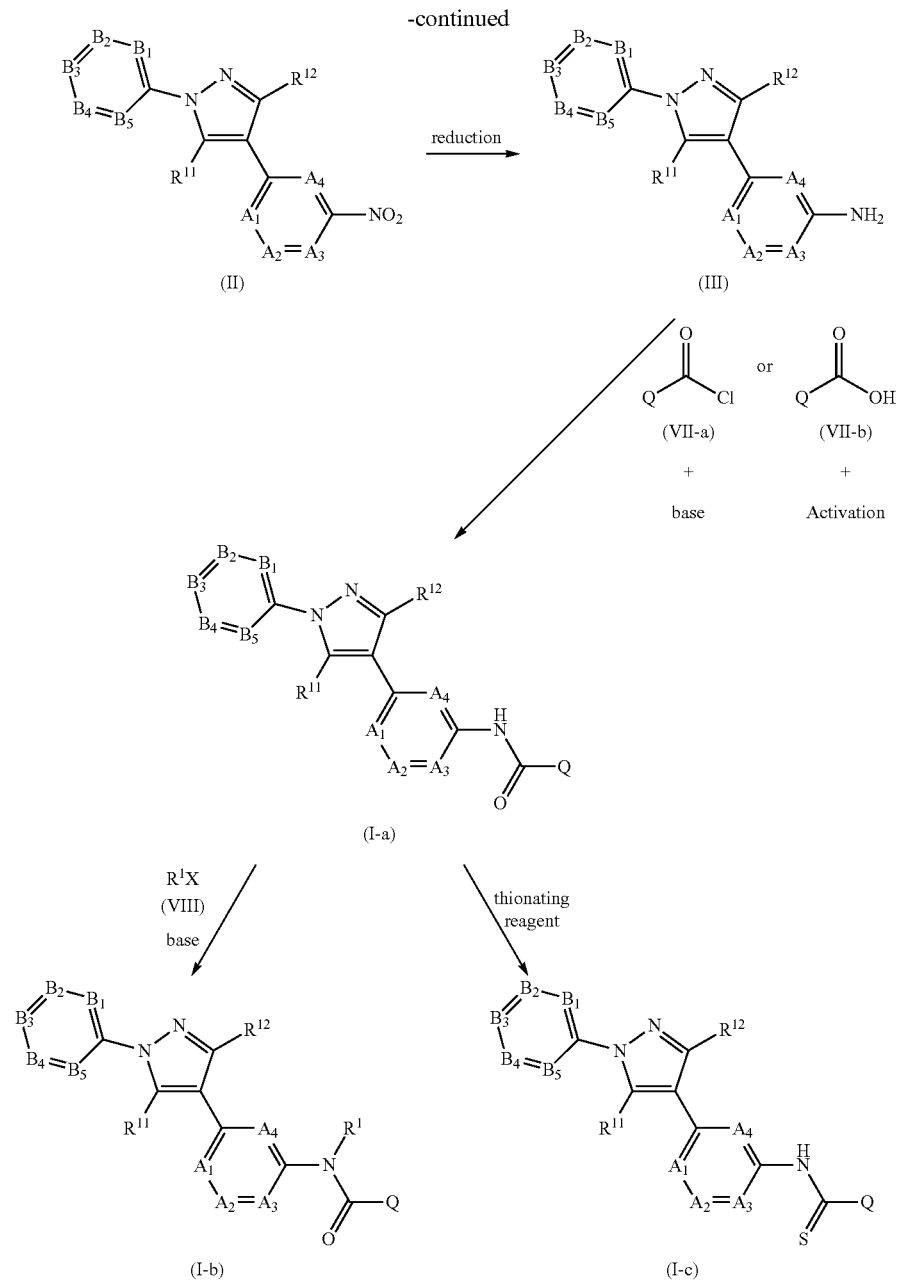

The $A_1$ to $A_4$, $B_1$ to $B_5$, Q, $R^1$, $R^{11}$ and $R^{12}$ radicals are each as defined above.

Oxidizing agents for the oxidation of alcoholic groups are known (cf., for example, oxidation reagents in Organic Synthesis by Oxidation with Metal Compounds, Mijs, de Jonge, Plenum Verlag, New York, 1986; Manganese Compounds as Oxidizing Agents in Organic Chemistry, Arndt, Open Court Publishing Company, La Salle, Ill., 1981; The Oxidation of Organic Compounds by Permanganate Ion and Hexavalent Chromium, Lee, Open Court Publishing Company, La Salle, Ill., 1980). An oxidation can be conducted, for example, in the presence of permanganates (e.g. potassium permanganate), metal oxides (e.g. manganese dioxide, chromium oxides, which are used, for example, in dipyridinechromium(VI) oxide as Collins reagent (cf. J. C. Collins et al., Tetrahedron Lett. 30, 3363-3366, 1968). Likewise in the presence of pyridinium chlorochromate (e.g. Corey's reagent) (cf. also R. O. Hutchins et al., Tetrahedron Lett. 48, 4167-4170, 1977; D. Landini et al. Synthesis 134-136, 1979) or ruthenium tetroxide (cf. S.-I. Murahashi, N. Komiya Ruthenium-catalyzed Oxidation of Alkenes, Alcohols, Amines, Amides, β-Lactams, Phenols and Hydrocarbons, in: Modern Oxidation Methods, Baeckvall, Jan-Erling (Eds.), Wiley-VCH-Verlag GmbH & Co. KGaA, 2004). Likewise suitable are ultrasound-induced oxidation reactions, and the use of potassium permanganate (cf. J. Yamawaki et al., Chem. Lett. 3, 379-380, 1983).

For deblocking/detachment of protecting groups (PG), it is possible to use any known suitable acidic or basic reaction auxiliaries by the procedures described in the literature. When protecting groups of the carbamate type are used for amino groups, preference is given to using acidic reaction auxiliaries. When the t-butylcarbamate protecting group (BOC group) is used, for example, mixtures of mineral acids such as hydrochloric acid, hydrobromic acid, nitric acid, sulphuric acid, phosphoric acid, or organic acids such as benzoic acid, formic acid, acetic acid, trifluoroacetic acid, methanesulphonic acid, benzenesulphonic acid or toluenesulphonic acid, and a suitable diluent such as water and/or an organic solvent such as tetrahydrofuran, dioxane, dichloromethane, chloroform, ethyl acetate, ethanol or methanol are used. Preference is given to mixtures of hydrochloric acid or acetic acid with water and/or an organic solvent such as ethyl acetate.

It is known that certain reactions and preparation processes can be carried out particularly efficiently in the presence of diluents or solvents and basic or acidic reaction auxiliaries. It is also possible to use mixtures of the diluents or solvents. The diluents or solvents are advantageously employed in such an amount that the reaction mixture is readily stirrable during the entire process.

Suitable diluents or solvents for carrying out the processes according to the invention are, in principle, all organic solvents which are inert under the specific reaction conditions. Examples include: halohydrocarbons (e.g. chlorohydrocarbons such as tetraethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene), alcohols (e.g. methanol, ethanol, isopropanol, butanol), ethers (e.g. ethyl propyl ether, methyl tert-butyl ether, n-butyl ether, anisole, phenetole, cyclohexyl methyl ether, dimethyl ether, diethyl ether, dipropyl ether, diisopropyl ether, di-n-butyl ether, diisobutyl ether, diisoamyl ether, ethylene glycol dimethyl ether, tetrahydrofuran, dioxane, dichlorodiethyl ether and polyethers of ethylene oxide and/or propylene oxide), amines (e.g. trimethyl-, triethyl-, tripropyl-, tributylamine, N-methylmorpholine, pyridine and tetramethylenediamine), nitrohydrocarbons (e.g. nitromethane, nitroethane, nitropropane, nitrobenzene, chloronitrobenzene, o-nitrotoluene; nitriles such as acetonitrile, propionitrile, butyronitrile, isobutyronitrile, benzonitrile, m-chlorobenzonitrile), tetrahydrothiophene dioxide, dimethyl sulphoxide, tetramethylene sulfoxide, dipropyl sulfoxide, benzyl methyl sulfoxide, diisobutyl sulfoxide, dibutyl sulfoxide, diisoamyl sulfoxide, sulfones (e.g. dimethyl, diethyl, dipropyl, dibutyl, diphenyl, dihexyl, methyl ethyl, ethyl propyl, ethyl isobutyl and pentamethylene sulfone) aliphatic, cycloaliphatic or aromatic hydrocarbons (e.g. pentane, hexane, heptane, octane, nonane and industrial hydrocarbons) also white spirits with components having boiling points in the range, for example, from 40° C. to 250° C., cymene, benzine fractions within a boiling point range from 70° C. to 190° C., cyclohexane, methylcyclohexane, petroleum ether, ligroin, octane, benzene, toluene, chlorobenzene, bromobenzene, nitrobenzene, xylene, esters (e.g. methyl, ethyl, butyl and isobutyl acetate, dimethyl, dibutyl and ethylene carbonate); amides (e.g. hexamethylenephosphoramide, formamide, N-methylformamide, N,N-dimethylformamide, N,N-dipropylformamide, N,N-dibutylformamide, N-methylpyrrolidone, N-methylcaprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine, N,N'-1,4-diformylpiperazine) and ketones (e.g. acetone, acetophenone, methyl ethyl ketone, methyl butyl ketone).

The basic reaction auxiliaries used to perform the processes according to the invention may be all suitable acid binders. Examples include: alkaline earth metal or alkali metal compounds (e.g. hydroxides, hydrides, oxides and carbonates of lithium, sodium, potassium, magnesium, calcium and barium), amidine bases or guanidine bases (e.g. 7-methyl-1,5,7-triazabicyclo[4.4.0]dec-5-ene (MTBD); diazabicyclo[4.3.0]nonene (DBN), diazabicyclo[2.2.2]octane (DABCO), 1,8-diazabicyclo[5.4.0]undecene (DBU), cyclohexyltetrabutylguanidine (CyTBG), cyclohexyltetramethylguanidine (CyTMG), N,N,N,N-tetramethyl-1,8-naphthalenediamine, pentamethylpiperidine) and amines, especially tertiary amines (e.g. triethylamine, trimethylamine, tribenzylamine, triisopropylamine, tributylamine, tricyclohexylamine, triamylamine, trihexylamine, N,N-dimethylaniline, N,N-dimethyltoluidine, N,N-dimethyl-p-aminopyridine, N-methylpyrrolidine, N-methylpiperidine, N-methylimidazole, N-methylpyrazole, N-methylmorpholine, N-methylhexamethylenediamine, pyridine, 4-pyrrolidinopyridine, 4-dimethylaminopyridine, quinoline, α-picoline, R-picoline, isoquinoline, pyrimidine, acridine, N,N,N', N'-tetramethylenediamine, N,N,N',N'-tetraethylenediamine, quinoxaline, N-propyldiisopropylamine, N-ethyldiisopropylamine, N,N'-dimethylcyclohexylamine, 2,6-lutidine, 2,4-lutidine or triethyldiamine).

Acidic reaction auxiliaries used for performance of the processes according to the invention may be all mineral acids (e.g. hydrohalic acids such as hydrofluoric acid, hydrochloric acid, hydrobromic acid or hydriodic acid, and also sulphuric acid, phosphoric acid, phosphorous acid, nitric acid), Lewis acids (e.g. aluminium(III) chloride, boron trifluoride or its etherate, titanium(V) chloride, tin(V) chloride, and organic acids (e.g. formic acid, acetic acid, propionic acid, malonic acid, lactic acid, oxalic acid, fumaric acid, adipic acid, stearic acid, tartaric acid, oleic acid, methanesulphonic acid, benzoic acid, benzenesulphonic acid or para-toluenesulphonic acid).

If protecting groups are envisaged in the reaction schemes, it is possible to use any commonly known protecting groups. Especially those which are described by Greene T. W., Wuts P. G. W. in Protective Groups in Organic Synthesis; John Wiley & Sons, Inc. 1999, "Protection for the hydroxyl group including 1,2- and 1,3-diols".

Also suitable are protective groups
of the substituted methyl ether type (e.g. methoxymethyl ether (MOM), methylthiomethyl ether (MTM), (phenyldimethylsilyl)methoxymethyl ether (SNOM-OR), benzyloxymethyl ether (BOM-OR) para-methoxybenzyloxymethyl ether (PMBM-OR), para-nitrobenzyloxymethyl ether, ortho-nitrobenzyloxymethyl ether (NBOM-OR), (4-methoxyphenoxy)methyl ether (p-AOM-OR), guaiacolmethyl ether (GUM-OR), t-butoxymethyl ether, 4-pentyloxymethyl ether (POM-OR), silyloxymethyl ether, 2-methoxyethoxymethyl ether (MEM-OR), 2,2,2-trichloroethoxymethyl ether, bis(2-chloroethoxy)methyl ether, 2-(trimethylsilyl)ethoxymethyl ether (SEM-OR), methoxymethyl ether (MM-OR));

of the substituted ethyl ether type (e.g. 1-ethoxyethyl ethers (EE-OR), 1-(2-chloroethoxy)ethyl ethers (CEE-OR), 1-[2-(trimethylsilyl)ethoxy]ethyl ethers (SEE-OR), 1-methyl-1-methoxyethyl ethers (MIP-OR), 1-methyl-1-benzyloxyethyl ethers (MBE-OR), 1-methyl-1-benzyloxy-2-fluoroethyl ethers (MIP-OR), 1-methyl-1-phenoxyethyl ether, 2,2,-trichloroethyl ethers, 1,1-dianisyl-2,2,2-trichloroethyl ethers (DATE-OR), 1,1,1,3,3,3-hexafluoro-2-phenylisopropyl ethers (HIP-OR), 2-trimethylsilylethyl ethers, 2-(benzylthio)ethyl ethers, 2-(phenylselenyl)ethyl ethers), of an ether (e.g. tetrahydropyranyl ethers (THP-OR), 3-bromotetrahydropyranyl ethers (3-BrTHP-OR), tetrahydrothiopyranyl ethers, 1-methoxycyclohexyl ethers, 2- and 4-picolyl ethers, 3-methyl-2-picolyl-N-oxide ethers, 2-quinolinylmethyl ethers (Qm-OR), 1-pyrenylmethyl ethers, diphenylmethyl ethers (DPM-OR), para, para'-dinitrobenzhydryl ethers (DNB-OR), 5-dibenzosuberyl ethers, triphenylmethyl ethers (Tr-OR), alpha-naphthyldiphenylmethyl ethers, para-methoxyphenyldiphenylmethyl ethers (MMTrOR), di(para-methoxyphenyl)phenylmethyl ethers (DMTr-OR), tri(para-methoxyphenyl)phenylmethyl ethers (TMTr-OR), 4-(4'-bromophenacyloxy)phenyldiphenylmethyl ethers, 4,4',4''-tris(4,5-dichlorophthalimidophenyl)methyl ethers (CPTr-OR), 4,4',4''-tris(benzoyloxyphenyl)methyl ethers (TBTr-OR), 4,4'-dimethoxy-3''-[N-(imidazolylmethyl)]trityl ethers (IDTr-OR), 4,4'-dimethoxy-3''-[N-(imidazolylethyl)carbamoyl]trityl ethers (IETr-OR), 1,1-bis(4-methoxyphenyl)-1'-pyrenylmethyl ethers (Bmpm-OR), 9-anthryl ethers, 9-(9-phenyl)xanthenyl ethers (pixyl-OR), 9-(9-phenyl-10-oxo)anthryl (tritylon ethers), 4-methoxytetrahydropyranyl ethers (MTHP-OR), 4-methoxytetrahydrothiopyranyl ethers, 4-methoxytetrahydrothiopyranyl-S,S-dioxide, 1-[(2-chloro-4-methyl)phenyl]-4-methoxypiperidin-4-yl ethers (CTMP-OR), 1-(2-fluorophenyl)-4-methoxypiperidin-4-yl ethers (Fpmp-OR), 1,4-dioxan-2-yl ethers, tetrahydrofuranyl ethers, tetrahydrothiofuranyl ethers, 2,3,3a,4,5,6,7,7a-octahydro-7,8,8-trimethyl-4,7-methanebenzofuran-2-yl ethers (MBF-OR), t-butyl ethers, allyl ethers, propargyl ethers, parachlorophenyl ethers, para-methoxyphenyl ethers, paranitrophenyl ethers, para-2,4-dinitrophenyl ethers (DNP-OR), 2,3,5,6-tetrafluoro-4-(trifluoromethyl)phenyl ethers, benzyl ethers (Bn-OR));

of the substituted benzyl ether type (for example paramethoxybenzyl ether (MPM-OR), 3,4-dimethoxybenzyl ether (DMPM-OR), ortho-nitrobenzyl ether, para-nitrobenzyl ether, para-halobenzyl ether, 2,6-dichlorobenzyl ether, para-aminoacylbenzyl ether (PAB-OR), para-azidobenzyl ether (Azb-OR), 4-azido-3-chlorobenzyl ether, 2-trifluoromethylbenzyl ether, para-(methylsulphinyl)benzyl ether (Msib-OR));

of the silyl ether type (for example trimethylsilyl ether (TMS-OR), triethylsilyl ether (TES-OR), triisopropylsilyl ether (TIPS-OR), dimethylisopropylsilyl ether (IPDMS-OR), diethylisopropylsilyl ether (DEIPS-OR), dimethylhexylsilyl ether (TDS-OR), t-butyldimethylsilyl ether (TBDMS-OR), t-butyldiphenylsilyl ether (TBDPS-OR), tribenzylsilyl ether, tri-para-xylylsilyl ether, triphenylsilyl ether (TPS-OR), diphenylmethylsilyl ether (DPMS-OR), di-t-butylmethylsilyl ether (DTBMS-OR), tris(trimethylsilyl)silyl ether (sisyl ether), di-t-butylmethylsilyl ether (DTBMS-OR), tris(trimethylsilyl)silyl ether (sisyl ether), (2-hydroxystyryl)dimethylsilyl ether (HSDMS-OR), (2-hydroxystyryl)diisopropylsilyl ether (HSDIS-OR), t-butylmethoxyphenylsilyl ether (TBMPS-OR), t-butoxydiphenylsilyl ether (DPTBOS-OR));

of the ester type (for example formate ester, benzoylformate ester, acetate ester (Ac-OR), chloroacetate ester, dichloroacetate ester, trichloroacetate ester, trifluoroacetate ester (TFA-OR), methoxyacetate ester, triphenylmethoxyacetate ester, phenoxyacetate ester, para-chlorophenoxyacetate ester, phenylacetate ester, diphenylacetate ester (DPA-OR), nicotinate ester, 3-phenylpropionate ester, 4-pentoate ester, 4-oxopentoate ester (levulinate) (Lev-OR), 4,4-(ethylenedithio)pentanoate ester (LevS-OR), 5-[3-bis(4-methoxyphenyl)hydroxymethoxyphenoxy]levulinate ester, pivaloate ester (Pv-OR), 1-adamantanoate ester, crotonate ester, 4-methoxycrotonate ester, benzoate ester (Bz-OR), paraphenylbenzoate ester, 2,4,6-trimethylbenzoate ester (mesitoate), 4-(methylthiomethoxy)butyrate ester (MTMB-OR), 2-(methylthiomethoxymethyl)benzoate ester (MTMT-OR), of the ester type (e.g. methyl carbonate, methoxymethyl carbonate, 9-fluorenylmethyl carbonate (Fmoc-OR), ethyl carbonate, 2,2,2-trichloroethyl carbonate (Troc-OR), 1,1-dimethyl-2,2,2-trichloroethyl carbonate (TCBOC-OR), 2-(trimethylsilyl)ethyl carbonate (TMS-OR), 2-(phenylsulfonyl)ethyl carbonate (Ps-OR), 2-(triphenylphosphonio)ethyl carbonate (Peoc-OR), t-butyl carbonate (Boc-OR), isobutyl carbonate, vinyl carbonate, allyl carbonate (Alloc-OR), para-nitrophenyl carbonate, benzyl carbonate (Z-OR), para-methoxybenzyl carbonate, 3,4-dimethoxybenzyl carbonate, ortho-nitrobenzyl carbonate, para-nitrobenzyl carbonate, 2-dansylethyl carbonate (Dnseoc-OR), 2-(4-nitrophenyl)ethyl carbonate (Npeoc-OR), 2-(2,4-dinitrophenyl)ethyl carbonate (Dnpeoc)), and of the sulphate type (for example allylsulphonate (Als-OR), methanesulphonate (Ms-OR), benzylsulphonate, tosylate (Ts-OR), 2-[(4-nitrophenyl)ethyl]sulphonate (Npes-OR)).

Catalysts suitable for performance of a catalytic hydrogenation in the process according to the invention are all the customary hydrogenation catalysts, for example platinum catalysts (e.g. platinum sheet, platinum sponge, platinum black, colloidal platinum, platinum oxide, platinum wire), palladium catalysts (e.g. palladium sponge, palladium black, palladium oxide, palladium-charcoal, colloidal palladium, palladium barium sulphate, palladium barium carbonate, palladium hydroxide), nickel catalysts (e.g. reduced nickel, nickel oxide, Raney nickel), ruthenium catalysts, cobalt catalysts (e.g. reduced cobalt, Raney cobalt), copper catalysts (e.g. reduced copper, Raney copper, Ullmann copper). Preference is given to using noble metal catalysts (e.g. platinum and palladium or ruthenium catalysts) which have optionally been applied to a suitable support (e.g. carbon or silicon), rhodium catalysts (e.g. tris(triphenylphosphine)rhodium(I) chloride in the presence of triphenylphosphine). Furthermore, it is possible to use "chiral hydrogenation catalysts" (for example those comprising chiral diphosphine ligands such as (2S,3S)-(−)-2,3-bis(diphenylphosphino)butane [(S,S)-chiraphos] or (R)-(+)-2,2'- or (S)-(−)-2,2'-bis(diphenylphosphino)-1,1'-binaphthalene [R(+)-BINAP or S(−)-BINAP]), whereby the proportion of an isomer in the isomer mixture is increased or the formation of another isomer is virtually completely suppressed.

Salts of the compounds according to the invention are prepared by standard methods. Representative acid addition salts are, for example, those formed by reaction with inorganic acids, such as, for example, sulphuric acid, hydrochloric acid, hydrobromic acid, phosphoric acid, or organic carboxylic acids such as acetic acid, trifluoroacetic acid, citric acid, succinic acid, butyric acid, lactic acid, formic acid, fumaric acid, maleic acid, malonic acid, camphoric acid, oxalic acid, phthalic acid, propionic acid, glycolic acid, glutaric acid, stearic acid, salicylic acid, sorbic acid, tartaric acid, cinnamic acid, valeric acid, picric acid, benzoic acid or organic sulphonic acids such as methanesulphonic acid and 4-toluenesulphonic acid.

Also representative are salts of compounds according to the invention which are formed from organic bases, for example pyridine or triethylamines, or those which are formed from inorganic bases, for example hydrides, hydroxides or carbonates of sodium, lithium, calcium, magnesium or barium, when the compounds of the general formula (I) have a structural element suitable for formation of this salt.

Synthesis methods for preparation of heterocyclic N-oxides and t-amines are known. They can be obtained with peroxy acids (e.g. peracetic acid and meta-chloroperbenzoic acid (MCPBA), hydrogen peroxide), alkyl hydroperoxides (e.g. t-butyl hydroperoxide), sodium perborate and dioxiranes (e.g. dimethyldioxirane). These methods are described, for example, by T. L. Gilchrist, in Comprehensive Organic Synthesis, vol. 7, p. 748-750, 1992, S. V. Ley, (Ed.), Pergamon Press; M. Tisler, B. Stanovnik, in Comprehensive Heterocyclic Chemistry, vol. 3, p. 18-20, 1984, A. J. Boulton, A. McKillop, (Eds.), Pergamon Press; M. R. Grimmett, B. R. T. Keene in Advances in Heterocyclic Chemistry, vol. 43, p. 149-163, 1988, A. R. Katritzky, (Ed.), Academic Press; M. Tisler, B. Stanovnik, in Advances in Heterocyclic Chemistry, vol. 9, p. 285-291, 1968, A. R. Katritzky, A. J. Boulton (Eds.), Academic Press; G. W. H. Cheeseman, E. S. G. Werstiuk in Advances in Heterocyclic Chemistry, vol. 22, p. 390-392, 1978, A. R. Katritzky, A. J. Boulton, (Eds.), Academic Press.

EXPERIMENTAL SECTION $^1$H-NMR Data $^1$H-NMR data were recorded using a Bruker Avance 400 equipped with a flow cell (60 μl volume), or using a Bruker AVIII 400 equipped with a 1.7 mm cryo-CPTCI sample head, or using a Bruker AVII 600 (600.13 MHz) equipped with a 5 mm cryo-TCI sample head, or using a Bruker AVIII 600 (601.6 MHz) equipped with a 5 mm cryo-CPMNP sample head. This was done using tetramethylsilane as reference (0.0 ppm) and CD$_3$CN, CDCl$_3$ or D$_6$-DMSO as deuterated solvent.

Synthesis Example Synthesis of N-[2-chloro-5-[1-[2,6-dimethyl-4-[1,2,2,2-tetrafluoro-1-(trifluoromethyl)ethyl]phenyl]pyrazol-4-yl]phenyl]-4-fluorobenzamide (Table 1, Ex. No. 4)

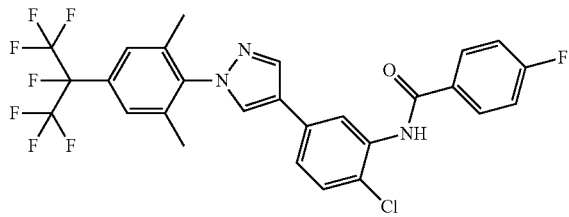 [SMILES: Cc1cc(C(F)(C(F)(F)F)C(F)(F)F)cc(C)c1-n1cc(-c2ccc(Cl)c(NC(=O)c3ccc(F)cc3)c2)cn1]

Step 1

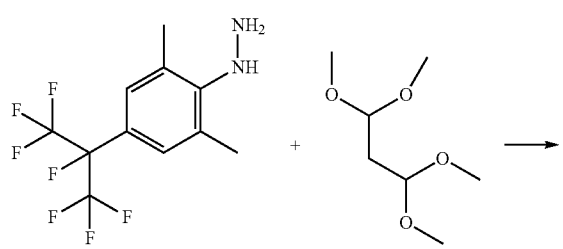

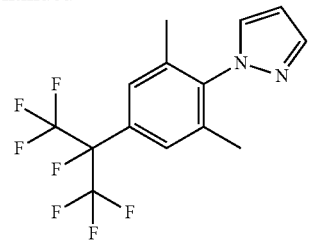

A 25 ml flask was initially charged with 3.41 g (11.2 mmol) of [2,6-dimethyl-4-[1,2,2,2-tetrafluoro-1-(trifluoromethyl)ethyl]phenyl]hydrazine (free base, known from US2003/187233) in 13 ml of ethanol. Then 1.84 g (11.2 mmol) of tetramethoxypropane and subsequently 0.55 g (5.6 mmol) of 96% sulphuric acid were added. The reaction mixture was heated to reflux for 2 h. Ethanol was evaporated off on a rotary evaporator under reduced pressure. The residue was partitioned between ethyl acetate and saturated aqueous sodium hydrogencarbonate solution. The organic phase was removed, dried with sodium sulphate and concentrated on a rotary evaporator under reduced pressure. The residue was distilled in a Kugelrohr under reduced pressure at 1 mbar and 150° C., and gave 2.5 g of 1-[2,6-dimethyl-4-[1,2,2,2-tetrafluoro-1-(trifluoromethyl)ethyl]phenyl]pyrazole.

Step 2

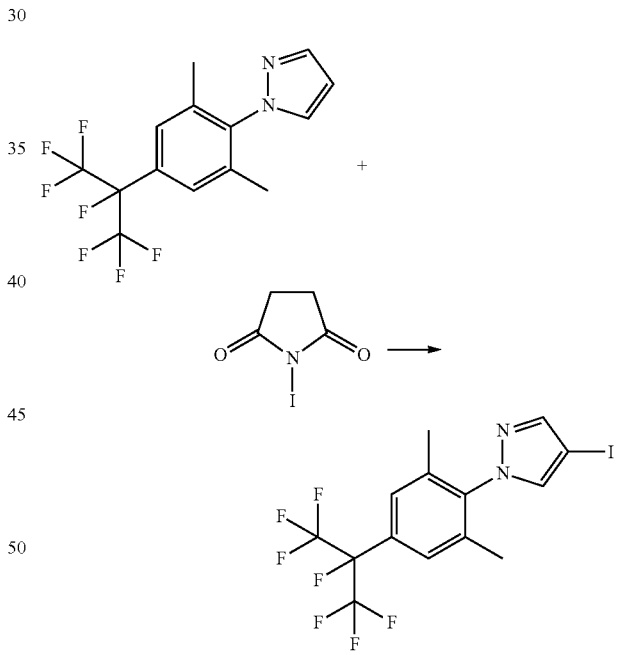

A 250 ml flask was initially charged with 2.5 g (7.34 mmol) of 1-[2,6-dimethyl-4-[1,2,2,2-tetrafluoro-1-(trifluoromethyl)ethyl]phenyl]pyrazole in 30 ml of acetonitrile, and 8.3 g (36.9 mmol) of N-iodosuccinimide in 50 ml of acetonitrile were added dropwise. Subsequently, the mixture was heated to reflux. For workup, the mixture was concentrated and the residue was partitioned between water and ethyl acetate. The organic phase was removed, washed first with saturated aqueous sodium hydrogensulphite solution, then with saturated sodium chloride solution, dried with sodium sulphate and concentrated. The residue was purified by chromatography with silica gel by means of a gradient from 90:10 to 70:30 (v/v) in cyclohexane/ethyl acetate. After concentration of the fractions containing the product, 2.5 g of a residue were obtained, which consisted of 1-[2,6-dimethyl-4-[1,2,2,2-tetrafluoro-1-(trifluoromethyl)ethyl]phenyl]-4-iodopyrazole and some toluene.
Step 3

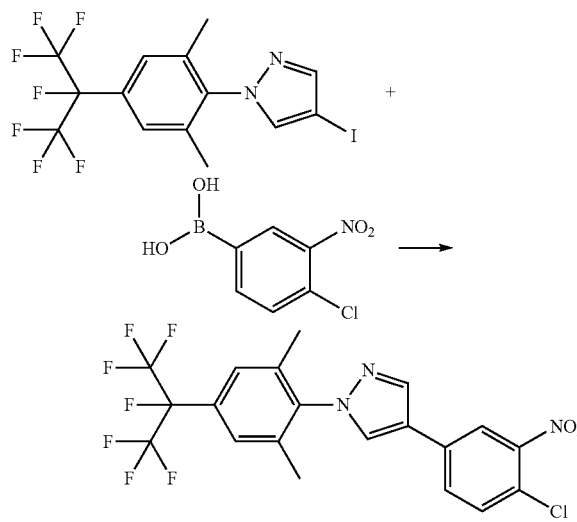

1 g (2.14 mmol) of 1-[2,6-dimethyl-4-[1,2,2,2-tetrafluoro-1-(trifluoromethyl)ethyl]phenyl]-4-iodopyrazole and 0.675 g (3 mmol) of 3-nitro-4-chlorophenylboronic acid were initially charged in 18 ml of 1,4-dioxane, and 0.16 g (0.21 mmol) of 1,1'-bis(diphenylphosphino)ferrocenepalladium(II) chloride and 9.6 ml of a 2M aqueous $Na_2CO_3$ solution were added. The mixture was stirred at 100° C. until conversion was complete. After the reaction mixture had cooled down, the complete mixture was concentrated on silica gel on a rotary evaporator and then chromatographed using silica gel (cyclohexane/ethyl acetate gradient). 0.86 g (78.1% of theory) were obtained as a colourless solid.

$^1$H-NMR, 400 MHz, $d_6$-DMSO, δ 8.71 (s, 1H), 8.44 (s, 1H), 8.39 (s, 1H), 8.02 (d, 1H), 7.82 (d, 1H), 7.60 (s, 2H), 2.13 (s, 6H).

lgP=5.39; MH+=496.0
Step 4

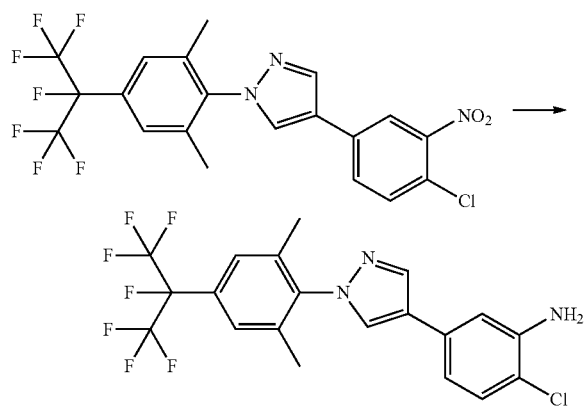

0.86 g (10.7 mmol) of 4-(4-chloro-3-nitrophenyl)-1-[2,6-dimethyl-4-[1,2,2,2-tetrafluoro-1-(trifluoromethyl)ethyl]phenyl]pyrazole (step 1) was dissolved in 9 mL of 1,4-dioxane and 0.94 g (4.16 mmol) of tin(II) chloride dihydrate was added at room temperature. The reaction mixture was cooled to 0° C., then 6.5 ml of conc. HCl were added dropwise and then the mixture was stirred under reflux for 2 hours. After completion of the reaction, the volume of the reaction mixture was concentrated to two thirds on the rotary evaporator, then made alkaline with saturated aqueous sodium carbonate solution. The aqueous mixture was extracted repeatedly with dichloromethane, the combined organic phases were dried over magnesium sulfate, filtered and concentrated, and the residue was chromatographed over silica gel (cyclohexane/ethyl acetate gradient). 0.48 g (73.5% of theory) of a yellowish oil were obtained.

$^1$H-NMR, 400 MHz, $d_6$-DMSO, δ 8.38 (s, 1H), 8.07 (s, 1H), 7.58 (s, 2H), 7.20 (d, 1H), 7.05 (s, 1H), 6.86 (d, 1H), 5.34 (s, 2H, $NH_2$), 2.11 (s, 6H).

lgP=4.93; MH+=466.0
Step 5

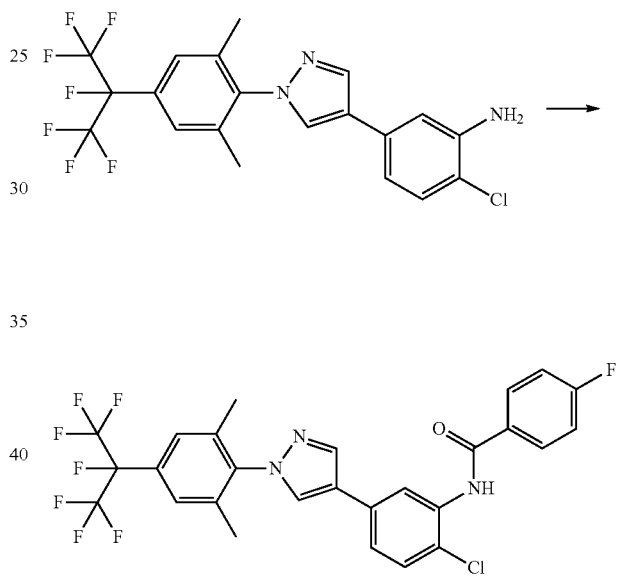

80 mg (0.17 mmol) of 2-chloro-5-[1-[2,6-dimethyl-4-[1,2,2,2-tetrafluoro-1-(trifluoromethyl)ethyl]phenyl]pyrazol-4-yl]aniline (step 2) were dissolved in 3 ml of THF and 27.2 mg (0.17 mmol) of 4-fluorobenzoyl chloride and 17.4 mg (0.17 mmol) of triethylamine were added at room temperature, and the mixture was stirred under reflux until conversion was complete, with monitoring by TLC. After cooling, 5 ml of water were added and the mixture was extracted repeatedly with dichloromethane. The combined organic phases were dried over magnesium sulphate, filtered and concentrated, and the residue was chromatographed using silica gel (cyclohexane/ethyl acetate gradient). 70 mg (67.4% of theory) of the target compound were obtained as a yellowish oil.

$^1$H-NMR, 400 MHz, $d_6$-DMSO, δ 10.21 (s, 1H, NH), 8.58 (s, 1H), 8.30 (s, 1H), 8.11-8.07 (dd, 2H), 7.85 (d, 1H), 7.64-7.57 (m, 4H), 7.42-7.37 (t, 2H), 2.13 (s, 6H).

lgP=5.57; MH+=588.1

The compounds listed in Table 1 were prepared using the preparation processes described above.

TABLE 1

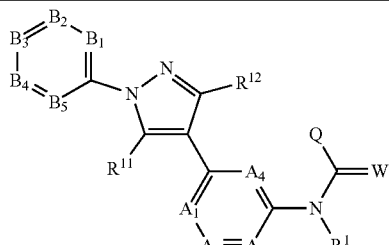

$A_1$, $B_2$, $B_4$ = C—H; $R^{11}$ and $R^{12}$ = H; W = O.

| Ex. No. | $B_1$ | $B_3$ | $B_5$ | $R^1$ | $A_2$ | $A_3$ | $A_4$ | Q | lgP[a] or retention time [min][b] | Mass [m/z][1] |
|---|---|---|---|---|---|---|---|---|---|---|
| 1 | C—Cl | CF3 | C—Cl | H | C—H | C—H | C—H | 3-Cl-pyridyl | lgP 4.19 | 511.0; 513.0 |
| 2 | C—CH3 | C-i-C3F7 | C—CH3 | H | C—H | C—Cl | C—H | 4pyridyl | lgP 4.41 | 571.1 |
| 3 | C—Cl | CF3 | C—Cl | H | C—H | C—H | C—H | 4pyridyl | lgP 3.2 | 477.0 |
| 4 | C—CH3 | C-i-C3F7 | C—CH3 | H | C—H | C—Cl | C—H | 4-F-phenyl | lgP 5.57 | 588.1 |
| 5 | C—CH3 | C-i-C3F7 | C—CH3 | H | C—H | C—F | C—H | 4-F-phenyl | lgP 5.07 | 572.1 |
| 6 | C—CH3 | C-i-C3F7 | C—CH3 | H | C—H | C—F | C—H | 4pyridyl | lgP 4.04 | 555.1 |
| 7 | C—CH3 | C-i-C3F7 | C—CH3 | H | C—H | C—F | C—F | 4-F-phenyl | lgP 4.84 | 590.1 |
| 8 | C—CH3 | C-i-C3F7 | C—CH3 | H | C—H | C—Cl | C—H | 3-F-phenyl | lgP 5.59 | 588.1 |
| 9 | C—CH3 | C-i-C3F7 | C—CH3 | H | C—H | C—F | C—F | 4pyridyl | lgP 3.92 | 573.1 |
| 10 | C—CH3 | C-i-C3F7 | C—CH3 | H | C—H | C—Cl | C—H | 2-F-phenyl | lgP 6.06 | 588.1 |
| 11 | C—CH3 | C-i-C3F7 | C—CH3 | H | N | C—Cl | C—H | 4-F-phenyl | lgP 5.14 | 589.1 |
| 12 | C—CH3 | C-i-C3F7 | C—CH3 | H | N | C—Cl | C—H | 4pyridyl | lgP 3.97 | 572.1 |
| 13 | C—CH3 | C-i-C3F7 | C—CH3 | H | N | C—Cl | C—H | 1-CN-1-cyclopropyl | lgP 4.69 | 560.0 |
| 14 | C—CH3 | C-i-C3F7 | C—CH3 | H | C—H | N | C—H | 4-F-phenyl | lgP 4.69 | 555.1 |
| 15 | C—CH3 | C-i-C3F7 | C—CH3 | H | C—H | C—F | C—H | 5-pyrimidinyl | lgP 3.95 | 556.1 |
| 16 | C—CH3 | C-i-C3F7 | C—CH3 | H | C—H | C—F | C—H | 6-pyrimidinyl | lgP 5.04 | 556.0 |
| 17 | C—Cl | C-i-C3F7 | C—Cl | H | N | C—CH3 | C—H | 4-F-phenyl | rt 1.19 | 609 |
| 18 | C—Cl | C-i-C3F7 | C—Cl | H | N | C—CH3 | C—H | 4pyridyl | rt 1.05 | 592 |
| 19 | C—Cl | C-i-C3F7 | C—Cl | H | N | C—F | C—H | 4pyridyl | rt 3.75[c] | 596 |
| 20 | C—CH3 | C-i-C3F7 | C—CH3 | H | C—H | C—N(CH3)2 | C—H | 4pyridyl | rt 1.30 | 580 |
| 21 | C—CH3 | C-i-C3F7 | C—CH3 | H | C—H | C—N(CH3)2 | C—H | 4-F-phenyl | rt 1.43 | 597 |
| 22 | C—Cl | C-i-C3F7 | C—Cl | H | C—H | C—F | C—H | 3-CH3O-4-F-phenyl | rt 1.36 | 642 |
| 23 | C—CH3 | C-i-C3F7 | C—CF3 | H | C—H | C—F | C—F | 4-F-phenyl | rt 1.43 | 644 |
| 24 | C—CH3 | C-i-C3F7 | C—CF3 | H | N | C—Cl | C—H | 3-CH3O-4-F-phenyl | rt 1.37 | 673 |
| 25 | C—CH3 | C-i-C3F7 | C—CF3 | H | C—H | C—F | C—F | 4pyridyl | rt 1.17 | 627 |
| 26 | C—CH3 | C-i-C3F7 | C—CF3 | H | C—H | C—F | C—F | 2-thiophenyl | rt 1.27 | 632 |
| 27 | C—CH3 | C-i-C3F7 | C—CF3 | H | C—H | C—F | C—F | 3-CH3O-4-F-phenyl | rt 1.31 | 674 |
| 28 | C—CH3 | C-i-C3F7 | C—CF3 | H | C—H | C—F | C—H | 3-CH3O-4-F-phenyl | rt 4.69[c] | 656 |
| 29 | C—CH3 | C-i-C3F7 | C—CF3 | H | C—H | C—F | C—H | 3-EtO-4-phenyl | rt 4.88[c] | 670 |
| 30 | C—CH3 | C-i-C3F7 | C—CF3 | H | C—H | C—F | C—H | 1-CH3-1-cyclopropyl | rt 1.39 | 586 |
| 31 | C—CH3 | C-i-C3F7 | C—CF3 | H | C—H | C—F | C—H | 3-thiophenyl | rt 1.36 | 614 |
| 32 | C—CH3 | C-i-C3F7 | C—CF3 | H | C—H | C—F | C—H | 3-CH3O-phenyl | rt 1.40 | 638 |
| 33 | C—CH3 | C-i-C3F7 | C—CF3 | H | C—H | C—F | C—H | 4-CN-phenyl | rt 4.48[c] | 633 |
| 35 | C—CH3 | C-i-C3F7 | C—CF3 | H | C—H | C—F | C—F | 3-CH3O-4-CN-phenyl | rt 1.37 | 663 |
| 36 | C—CH3 | C-i-C3F7 | C—CF3 | H | C—H | C—N(CH3)2 | C—H | 1-CH3-1-cyclopropyl | rt 1.51 | 611 |
| 37 | C—CH3 | C-i-C3F7 | C—CF3 | H | C—H | C—N(CH3)2 | C—H | 3-thiophenyl | rt 1.42 | 639 |
| 38 | C—CH3 | C-i-C3F7 | C—CF3 | H | C—H | C—N(CH3)2 | C—H | 3-CH3O-4-F-phenyl | rt 1.30 | 610 |
| 39 | C—CH3 | C-i-C3F7 | C—CF3 | H | C—H | C—F | C—F | 2-F-5-pyridyl | rt 1.34 | 627 |
| 40 | C—CH3 | C-i-C3F7 | C—CF3 | H | C—H | C—F | C—F | 2-F-5-pyridyl | rt 1.30 | 645 |
| 41 | C—CH3 | C-i-C3F7 | C—CF3 | CH3 | C—H | C—F | C—F | 2-F-5-pyridyl | rt 1.37 | 659 |
| 42 | C—CH3 | C-i-C3F7 | C—CF3 | H | C—H | C—H | C—F | 2-F-5-pyridyl | rt 1.33 | 627 |
| 43 | C—CH3 | C-i-C3F7 | C—CF3 | H | C—H | C—H | C—F | phenyl | rt 1.41 | 608 |
| 44 | C—CH3 | C-i-C3F7 | C—CF3 | CH3 | C—H | C—H | C—F | 2-F-5-pyridyl | rt 1.36 | 641 |
| 45 | C—CH3 | C-i-C3F7 | C—CF3 | CH3 | C—H | C—H | C—F | phenyl | rt 1.38 | 622 |
| 46 | C—CH3 | C-i-C3F7 | C—CF3 | H | C—H | C—F | C—H | 2-CN-5-pyridyl | rt 1.30 | 634 |
| 47 | C—CH3 | C-i-C3F7 | C—CF3 | H | C—H | C—F | C—H | 3-CH3O-4-CH3-phenyl | rt 1.41 | 652 |
| 48 | C—CH3 | C-i-C3F7 | C—CF3 | CH3 | C—H | C—F | C—H | 2-F-5-pyridyl | rt 1.29 | 641 |
| 49 | C—CH3 | C-i-C3F7 | C—CF3 | H | C—H | C—F | C—H | 2-Cl-5-pyridyl | rt 1.35 | 643 |
| 50 | C—CH3 | C-i-C3F7 | C—CF3 | H | C—H | C—F | C—H | 4pyridyl | rt 1.20 | 609 |
| 51 | C—CH3 | C-i-C3F7 | C—CF3 | H | C—H | C—F | C—H | 2-F-4-pyridyl | rt 1.32 | 627 |
| 52 | C—CH3 | C-i-C3F7 | C—CF3 | H | C—H | C—F | C—H | 3,4-(CH3)2-phenyl | rt 1.47 | 636 |
| 53 | C—CH3 | C-i-C3F7 | C—CF3 | H | C—H | C—F | C—H | 3-CH3-4-F-phenyl | rt 1.40 | 640 |
| 54 | C—CH3 | C-i-C3F7 | C—CF3 | H | C—H | C—F | C—H | 3-CH3-4-pyridyl | rt 1.20 | 623 |
| 55 | C—CH3 | C-i-C3F7 | C—CF3 | H | C—H | C—F | C—H | 3-F-4-MeO-phenyl | rt 1.34 | 656 |
| 56 | C—CH3 | C-i-C3F7 | C—CF3 | H | C—H | C—F | C—H | 3-F-4-Cl-phenyl | rt 1.41 | 660 |
| 57 | C—Br | C-i-C3F7 | C—CF3 | H | C—H | C—H | C—F | 4-F-phenyl | rt 1.39 | 672 |
| 58 | C—Br | C-i-C3F7 | C—CF3 | CH3 | C—H | C—H | C—F | 4-F-phenyl | rt 1.37 | 686 |
| 59 | C—Br | C-i-C3F7 | C—CF3 | H | C—H | C—H | C—F | 4pyridyl | | |
| 60 | C—Br | C-i-C3F7 | C—CF3 | CH3 | C—H | C—H | C—F | 4pyridyl | | |
| 61 | C—Cl | C-i-C3F7 | C—CF3 | H | C—H | C—H | C—F | 4-F-phenyl | | |
| 62 | C—Cl | C-i-C3F7 | C—CF3 | CH3 | C—H | C—H | C—F | 4-F-phenyl | | |
| 63 | C—Cl | C-i-C3F7 | C—CF3 | H | C—H | C—H | C—F | 4pyridyl | | |

TABLE 1-continued

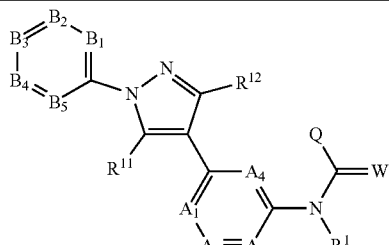

$A_1$, $B_2$, $B_4$ = C—H; $R^{11}$ and $R^{12}$ = H; W = O.

| Ex. No. | $B_1$ | $B_3$ | $B_5$ | $R^1$ | $A_2$ | $A_3$ | $A_4$ | Q | lgP[a] or retention time [min][b] | Mass [m/z][1] |
|---|---|---|---|---|---|---|---|---|---|---|
| 64 | C—Cl | C-i-C3F7 | C—CF3 | CH3 | C—H | C—H | C—F | 4pyridyl | | |
| 65 | C—CH3 | C-i-C3F7 | C—CF3 | H | C—H | C—F | C—F | 3-thietanyl | rt 1.30 | 622 |
| 66 | C—CH3 | C-i-C3F7 | C—CF3 | H | C—H | C—F | C—H | 3-thietanyl | rt 1.33 | 604 |
| 67 | C—CH3 | C-i-C3F7 | C—CF3 | H | C—H | C—H | C—F | 2-F-4-pyridyl | rt 2.46[d] | 627 |
| 68 | C—CH3 | C-i-C3F7 | C—CF3 | H | C—H | C—H | C—F | 4pyridyl | rt 2.30[d] | 609 |
| 69 | C—CH3 | C-i-C3F7 | C—CF3 | H | C—H | C—H | C—F | 2-CN-5-pyridyl | rt 4.43[c] | 634 |
| 70 | C—CH3 | C-i-C3F7 | C—CF3 | H | C—H | C—H | C—F | 2-Cl-5-pyridyl | rt 2.51[d] | 643 |
| 71 | C—CH3 | C-i-C3F7 | C—CF3 | H | C—H | C—H | C—F | 3-CH3O-4-F-phenyl | rt 4.69[c] | 656 |
| 72 | C—CH3 | C-i-C3F7 | C—CF3 | H | C—H | C—H | C—F | 3-F-4-CH3O-phenyl | rt 2.57[d] | 656 |
| 73 | C—CH3 | C-i-C3F7 | C—CF3 | H | C—H | C—H | C—F | 3-CH3O-phenyl | rt 2.41[d] | 638 |
| 74 | C—CH3 | C-i-C3F7 | C—CF3 | H | C—H | C—H | C—F | 3-CH3O-4-CN-phenyl | rt 1.32 | 663 |
| 75 | C—CH3 | C-i-C3F7 | C—CF3 | H | C—H | C—H | C—F | 3-thienyl | rt 1.33 | 614 |
| 76 | C—CH3 | C-i-C3F7 | C—CF3 | H | C—H | C—H | C—F | 2-thienyl | rt 1.33 | 614 |
| 77 | C—CH3 | C-i-C3F7 | C—CF3 | H | C—H | C—H | C—F | 4-oxazolyl | rt 1.39 | 599 |
| 78 | C—CH3 | C-i-C3F7 | C—CF3 | H | C—H | C—H | C—F | 4-F-phenyl | lgP 5.22 | 572.1 |
| 79 | C—CH3 | C-i-C3F7 | C—CF3 | H | C—H | C—H | C—F | 3pyridyl | lgP 4.14 | 555.1 |
| 80 | C—CH3 | C-i-C3F7 | C—CF3 | H | C—H | C—H | C—F | 4pyridyl | lgP 4.12 | 555.1 |

TABLE 2

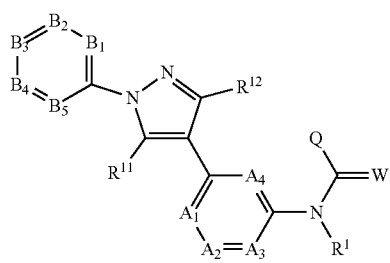

$A_2$, $B_2$, $B_4$ = C—H; $R^{11}$ and $R^{12}$ = H; W = O.

| Ex. No. | $B_1$ | $B_3$ | $B_5$ | $R^1$ | $A_1$ | $A_3$ | $A_4$ | Q | Retention time [min][d] | Mass [m/z][1] |
|---|---|---|---|---|---|---|---|---|---|---|
| 2-01 | C—CH3 | C-i-C3F7 | C—CF3 | H | C—F | C—H | C—H | 2-F-4-pyridyl | rt 2.53 | 627 |
| 2-02 | C—CH3 | C-i-C3F7 | C—CF3 | H | C—F | C—H | C—H | 4pyridyl | rt 2.38 | 609 |
| 2-03 | C—CH3 | C-i-C3F7 | C—CF3 | H | C—F | C—H | C—H | 2-CN-5-pyridyl | rt 2.49 | 634 |
| 2-04 | C—CH3 | C-i-C3F7 | C—CF3 | H | C—F | C—H | C—H | 2-Cl-5-pyridyl | rt 2.57 | 643 |
| 2-05 | C—CH3 | C-i-C3F7 | C—CF3 | H | C—F | C—H | C—H | 3-CH3O-4-F-phenyl | rt 2.62 | 656 |
| 2-06 | C—CH3 | C-i-C3F7 | C—CF3 | H | C—F | C—H | C—H | 3-F-4-CH3O-phenyl | rt 2.59 | 656 |
| 2-07 | C—CH3 | C-i-C3F7 | C—CF3 | H | C—F | C—H | C—H | 3-CH3O-phenyl | rt 2.61 | 638 |
| 2-08 | C—CH3 | C-i-C3F7 | C—CF3 | H | C—F | C—H | C—H | 3-CH3O-4-CN-phenyl | rt 2.55 | 663 |
| 2-09 | C—CH3 | C-i-C3F7 | C—CF3 | H | C—F | C—H | C—H | 3-thienyl | rt 4.67[c] | 613 |
| 2-10 | C—CH3 | C-i-C3F7 | C—CF3 | H | C—F | C—H | C—H | phenyl | rt 1.36[b] | 607 |
| 2-11 | C—CH3 | C-i-C3F7 | C—CF3 | H | C—F | C—H | C—H | 5-oxazolyl | rt 2.35 | 599 |
| 2-12 | C—CH3 | C-i-C3F7 | C—CF3 | H | C—F | C—H | C—H | 4-oxazolyl | rt 1.28[b] | 598 |
| 2-13 | C—Br | C-i-C3F7 | C—CF3 | H | C—F | C—H | C—H | 4pyridyl | rt 2.30 | 673 |
| 2-14 | C—Br | C-i-C3F7 | C—CF3 | H | C—F | C—H | C—H | 4-oxazolyl | rt 1.32 | 662 |

TABLE 3

Intermediates

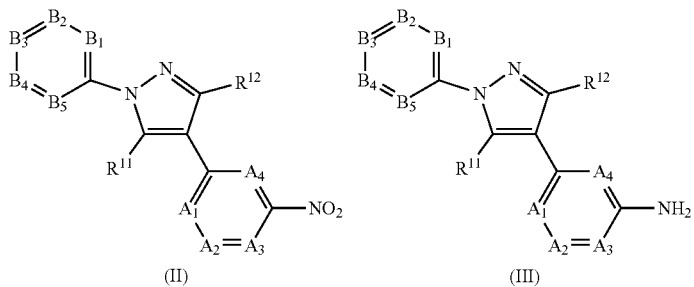

$B_2, B_4 = C-H; R^{11}$ and $R^{12} = H.$

| Ex. No. | $B_1$ | $B_3$ | $B_5$ | $A_1$ | $A_2$ | $A_3$ | $A_4$ | lgP[a] or retention time [min][b] | Mass [m/z][1] |
|---|---|---|---|---|---|---|---|---|---|
| II-1 | C—Cl | C—CF$_3$ | C—Cl | C—H | C—H | C—H | C—H | lgP 4.32 | 402.0; 404.0 |
| II-2 | C—Cl | C—CF$_3$ | C—Cl | C—H | C—H | C—Cl | C—H | | |
| II-3 | C—Cl | C—CF$_3$ | C—Cl | C—H | C—H | C—F | C—H | | |
| II-4 | C—Cl | C—CF$_3$ | C—Cl | C—H | C—H | C—F | C—F | | |
| II-5 | C—Cl | C—CF$_3$ | C—Cl | C—H | C—H | C—H | C—F | | |
| II-6 | C—CH$_3$ | C-i-C$_3$F$_7$ | C—CH$_3$ | C—H | C—H | C—H | C—H | | |
| II-7 | C—CH$_3$ | C-i-C$_3$F$_7$ | C—CH$_3$ | C—H | C—H | C—Cl | C—H | lgP 5.39 | 496.0 |
| II-8 | C—CH$_3$ | C-i-C$_3$F$_7$ | C—CH$_3$ | C—H | C—H | C—F | C—H | | |
| II-9 | C—CH$_3$ | C-i-C$_3$F$_7$ | C—CH$_3$ | C—H | C—H | C—F | C—F | | |
| II-10 | C—CH$_3$ | C-i-C$_3$F$_7$ | C—CH$_3$ | C—H | C—H | C—H | C—F | | |
| II-11 | C—CH$_3$ | C-i-C$_3$F$_7$ | C—CF$_3$ | C—H | C—H | C—H | C—H | | |
| II-12 | C—CH$_3$ | C-i-C$_3$F$_7$ | C—CF$_3$ | C—H | C—H | C—Cl | C—H | | |
| II-13 | C—CH$_3$ | C-i-C$_3$F$_7$ | C—CF$_3$ | C—H | C—H | C—F | C—H | | |
| II-14 | C—CH$_3$ | C-i-C$_3$F$_7$ | C—CF$_3$ | C—H | C—H | C—F | C—F | | |
| II-15 | C—CH$_3$ | C-i-C$_3$F$_7$ | C—CF$_3$ | C—H | C—H | C—H | C—F | | |
| II-16 | C—Cl | C-i-C$_3$F$_7$ | C—CF$_3$ | C—H | C—H | C—H | C—H | | |
| II-17 | C—Cl | C-i-C$_3$F$_7$ | C—CF$_3$ | C—H | C—H | C—Cl | C—H | | |
| II-18 | C—Cl | C-i-C$_3$F$_7$ | C—CF$_3$ | C—H | C—H | C—F | C—H | | |
| II-19 | C—Cl | C-i-C$_3$F$_7$ | C—CF$_3$ | C—H | C—H | C—F | C—F | | |
| II-20 | C—Cl | C-i-C$_3$F$_7$ | C—CF$_3$ | C—H | C—H | C—H | C—F | | |
| II-21 | C—Br | C-i-C$_3$F$_7$ | C—CF$_3$ | C—H | C—H | C—H | C—H | | |
| II-22 | C—Br | C-i-C$_3$F$_7$ | C—CF$_3$ | C—H | C—H | C—Cl | C—H | | |
| II-23 | C—Br | C-i-C$_3$F$_7$ | C—CF$_3$ | C—H | C—H | C—F | C—H | | |
| II-24 | C—Br | C-i-C$_3$F$_7$ | C—CF$_3$ | C—H | C—H | C—F | C—F | | |
| II-25 | C—Br | C-i-C$_3$F$_7$ | C—CF$_3$ | C—H | C—H | C—H | C—F | | |
| II-26 | C—CH$_3$ | C-i-C$_3$F$_7$ | C—CF$_3$ | C—F | C—H | C—H | C—H | | |
| II-27 | C—Br | C-i-C$_3$F$_7$ | C—CF$_3$ | C—F | C—H | C—H | C—H | | |
| II-28 | C—CH$_3$ | C—CH$_3$ | C—CF$_3$ | C—H | C—H | C—H | C—F | | |
| III-1 | C—Cl | CF$_3$ | C—Cl | C—H | C—H | C—H | C—H | lgP 2.90 | 371.9; 373.9 |
| III-2 | C—Cl | CF$_3$ | C—Cl | C—H | C—H | C—Cl | C—H | | |
| III-3 | C—Cl | CF$_3$ | C—Cl | C—H | C—H | C—F | C—H | | |
| III-4 | C—Cl | CF$_3$ | C—Cl | C—H | C—H | C—F | C—F | | |
| III-5 | C—Cl | CF$_3$ | C—Cl | C—H | C—H | C—H | C—F | | |
| III-6 | C—CH$_3$ | C-i-C$_3$F$_7$ | C—CH$_3$ | C—H | C—H | C—H | C—H | rt 1.22 | 432 |
| III-7 | C—CH$_3$ | C-i-C$_3$F$_7$ | C—CH$_3$ | C—H | C—H | C—Cl | C—H | lgP 4.93 | 466.0 |
| III-8 | C—CH$_3$ | C-i-C$_3$F$_7$ | C—CH$_3$ | C—H | C—H | C—F | C—H | lgP 4.47 | 450.1 |
| III-9 | C—CH$_3$ | C-i-C$_3$F$_7$ | C—CH$_3$ | C—H | C—H | C—F | C—F | lgP 4.81 | 468.1 |
| III-10 | C—CH$_3$ | C-i-C$_3$F$_7$ | C—CH$_3$ | C—H | C—H | C—H | C—F | lgP 4.61 | 450.2 |
| III-11 | C—CH$_3$ | C-i-C$_3$F$_7$ | C—CF$_3$ | C—H | C—H | C—H | C—H | | |
| III-12 | C—CH$_3$ | C-i-C$_3$F$_7$ | C—CF$_3$ | C—H | C—H | C—Cl | C—H | rt 1.18 | 521 |
| III-13 | C—CH$_3$ | C-i-C$_3$F$_7$ | C—CF$_3$ | C—H | C—H | C—F | C—H | rt 1.59[e] | 504 |
| III-14 | C—CH$_3$ | C-i-C$_3$F$_7$ | C—CF$_3$ | C—H | C—H | C—F | C—F | rt 1.35 | 522 |
| III-15 | C—CH$_3$ | C-i-C$_3$F$_7$ | C—CF$_3$ | C—H | C—H | C—H | C—F | rt 1.31 | 504 |
| III-16 | C—Cl | C-i-C$_3$F$_7$ | C—CF$_3$ | C—H | C—H | C—H | C—H | | |
| III-17 | C—Cl | C-i-C$_3$F$_7$ | C—CF$_3$ | C—H | C—H | C—Cl | C—H | | |
| III-18 | C—Cl | C-i-C$_3$F$_7$ | C—CF$_3$ | C—H | C—H | C—F | C—H | rt 1.31 | 490 |
| III-19 | C—Cl | C-i-C$_3$F$_7$ | C—CF$_3$ | C—H | C—H | C—F | C—F | | |
| III-20 | C—Cl | C-i-C$_3$F$_7$ | C—CF$_3$ | C—H | C—H | C—H | C—F | | |
| III-21 | C—Br | C-i-C$_3$F$_7$ | C—CF$_3$ | C—H | C—H | C—H | C—H | | |
| III-22 | C—Br | C-i-C$_3$F$_7$ | C—CF$_3$ | C—H | C—H | C—Cl | C—H | | |
| III-23 | C—Br | C-i-C$_3$F$_7$ | C—CF$_3$ | C—H | C—H | C—F | C—H | | |
| III-24 | C—Br | C-i-C$_3$F$_7$ | C—CF$_3$ | C—H | C—H | C—F | C—F | | |
| III-25 | C—Br | C-i-C$_3$F$_7$ | C—CF$_3$ | C—H | C—H | C—H | C—F | rt 1.30 | 568 |
| III-26 | C—Cl | C-i-C$_3$F$_7$ | C—Cl | C—H | N | C—CH$_3$ | C—H | rt 0.82 | 487 |
| III-27 | C—Cl | C-i-C$_3$F$_7$ | C—Cl | C—H | N | C—CF$_3$ | C—H | rt 3.76[e] | 491 |
| III-28 | C—CH$_3$ | C-i-C$_3$F$_7$ | C—CH$_3$ | C—H | C—H | C—N(CH$_3$)$_2$ | C—H | rt 1.17 | 475 |
| III-29 | C—CH$_3$ | C-i-C$_3$F$_7$ | C—CH$_3$ | C—H | N | C—Cl | C—H | rt 1.20 | 467 |
| III-30 | C—CF$_3$ | C-i-C$_3$F$_7$ | C—CH$_3$ | C—H | C—H | C—N(CH$_3$)$_2$ | C—H | rt 1.56[e] | 529 |

TABLE 3-continued

Intermediates

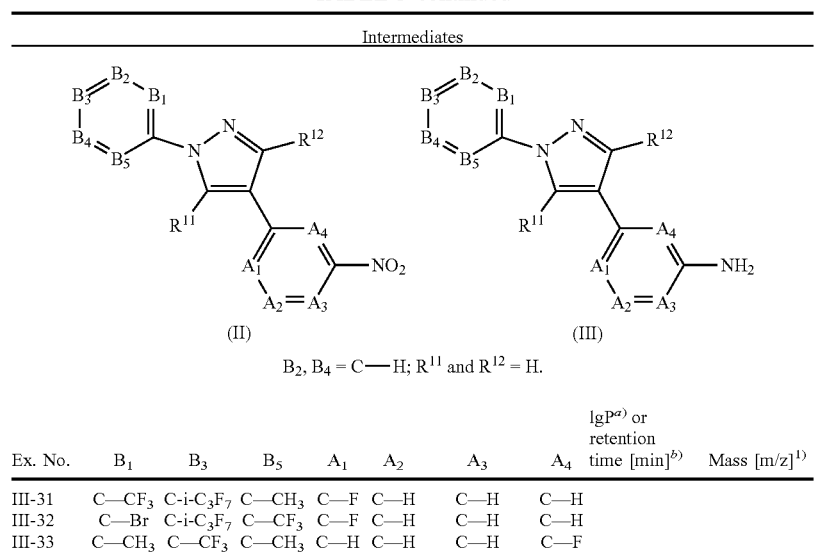

$B_2, B_4 = C—H; R^{11}$ and $R^{12} = H$.

| Ex. No. | $B_1$ | $B_3$ | $B_5$ | $A_1$ | $A_2$ | $A_3$ | $A_4$ | lgP$^{a)}$ or retention time [min]$^{b)}$ | Mass [m/z]$^{1)}$ |
|---|---|---|---|---|---|---|---|---|---|
| III-31 | C—CF$_3$ | C-i-C$_3$F$_7$ | C—CH$_3$ | C—F | C—H | C—H | C—H | | |
| III-32 | C—Br | C-i-C$_3$F$_7$ | C—CF$_3$ | C—F | C—H | C—H | C—H | | |
| III-33 | C—CH$_3$ | C—CF$_3$ | C—CH$_3$ | C—H | C—H | C—H | C—F | | |

$^{a)}$Note regarding the determination of the logP values (lgP): The determination of the given logP values was carried out in accordance with EEC Directive 79/831 Annex V.A8 by HPLC (High Performance Liquid Chromatography) on a reversed-phase column (C18). Agilent 1100 LC system; 50*4.6 Zorbax Eclipse Plus C18 1.8 micron; mobile phase A: acetonitrile (0.1% formic acid); mobile phase B: water (0..09% formic acid); linear gradient from 10% acetonitrile to 95% acetonitrile in 4.25 min, the 95% acetonitrile for a further 1.25 min; oven temperature 55° C.; flow rate: 2.0 mL/min.
$^{b)}$Note regarding the determination of the retention times (rt): Instrument: Waters ACQUITY SQD UPLC System; column: Waters Acquity UPLC HSS T3 1.8 µ 50 × 1 mm; mobile phase A: 1 1 of water + 0.25 ml of 99% strength formic acid, moblie phase B: 1 1 of acetonitrile + 0.25 ml of 99% strength formic acid; gradient: 0.0 min 90% A → 1.2 min 5% A → 2.0 min 5% A; oven: 50° C.; flow rate: 0.40 ml/min; UV detection: 208-400 nm.
$^{c)}$Note regarding the determination of the retention times. Instrument: Waters ACQUITY SQD UPLC System; column: Waters Acquity UPLC HSS T3 1.8 µ 50 × 1 mm; mobile phase A: 1 1 of water + 0.25 ml of 99% strength formic acid, moblie phase B: 1 1 of acetonitrile + 0.25 ml of 99% strength formic acid; gradient: 0.0 min 95% A → 6.0 min 5% A → 7.5 min 5% A; oven: 50° C.; flow rate: 0.35 ml/min; UV detection: 210-400 nm.
$^{d)}$Note regarding the determination of the retention times (rt): Insrtument: UHPLC+: Thermo Scientific UltiMate 3000; column: Waters, HSST3, 2.1 × 75 mm, C18 1.8 µm; mobile phase A: 1 1 of water + 0.01% formic acid; moblie phase B: 1 1 of acetonitrile + 0.01% formic acid; gradient: 0.0 min 10% B → 2.5 min 95% B → 3.5 min 95% B; oven: 50° C.; flow rate: 0.90 ml/min; UV detection: 210 nm/Optimum Integration Path 210-300 nm.
$^{e)}$Note regarding the determination of the retention times (rt): Insrtument: Agilent MS Quad 6150; HPLC: Agilent 1290; column: Waters Acquity UPLC HSS T3 1.8 µ 50 × 2.1 mm; mobile phase A: 1 1 of water + 0.25 ml of 99% strength formic acid, moblie phase B: 1 1 of acetonitrile + 0.25 ml of 99% strength formic acid; gradient: 0.0 min 90% A → 0.3 min 90% A →1.7 min 5% A → 3.0 min 5% A; oven: 50° C.; flow rate: 1.20 ml/min; UV detection: 205-305 nm.
$^{1)}$Mass detection was carried out using an Agilent MSD system or a Thermo Scientific FT-MS. The stated mass is the peak of the isotope pattern of the [M + H]$^+$ ion of the highest intensity.

NMR Data of Selected Examples
NMR Peak Lists

The 1H-NMR data of selected examples are noted in the form of 1H-NMR peak lists. For each signal peak, first the δ value in ppm and then the signal intensity in round brackets are listed. The pairs of δ value-signal intensity numbers for different signal peaks are listed with separation from one another by semicolons.

The peak list for one example therefore takes the form of:
$\delta_1$ (intensity$_1$); $\delta_2$ (intensity$_2$); . . . ; $\delta_i$ (intensity$_i$); . . . ; $\delta_n$ (intensity$_n$)

The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum.

For calibration of the chemical shift of 1H NMR spectra tetramethylsilane and/or the chemical shift of the solvent are used, particularly in the case of spectra measured in DMSO. Therefore, the tetramethylsilane peak may but need not occur in NMR peak lists.

The lists of the 1H NMR peaks are similar to the conventional 1H NMR printouts and thus usually contain all peaks listed in a conventional NMR interpretation.

In addition, like conventional 1H NMR printouts, they may show solvent signals, signals of stereoisomers of the target compounds, which likewise form part of the subject-matter of the invention, and/or peaks of impurities.

In the reporting of compound signals in the delta range of solvents and/or water, our lists of 1H NMR peaks show the usual solvent peaks, for example peaks of DMSO in DMSO-D$_6$ and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help in identifying reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the relevant peak picking in conventional 1H NMR interpretation.

Further details of 1H NMR peak lists can be found in the Research Disclosure Database Number 564025.

Table 4: $^1$H-NMR data were recorded using a Bruker Avance 400 equipped with a flow cell (60 µl volume), or using a Bruker AVIII 400 equipped with a 1.7 mm cryo-CPTCI sample head, or using a Bruker AVII 600 (600.13 MHz) equipped with a 5 mm cryo-TCI sample head, or using a Bruker AVIII 600 (601.6 MHz) equipped with a 5 mm cryo-CPMNP probe head. This was done using tetramethylsilane as reference (0.0 ppm) and CD$_3$CN, CDCl$_3$ or D$_6$-DMSO as deuterated solvent.

Table 5: The $^1$H-NMR data were measured using Bruker AVIII 400 spectrometers (400.13 MHz) equipped with 5 mm measuring heads or using a Bruker AVIII 500 spectrometer (500.13 MHz) with a 5 mm broadband head or a 5 mm Prodigy™ probe head. This was done using tetramethylsilane as reference (0.0 ppm) and predominantly D$_6$-DMSO as deuterated solvent.

TABLE 4

NMR peak list (1)

Example 1: $^1$H-NMR(400.0 MHz, d$_6$-DMSO): δ =
10.715(3.3); 8.650(2.4); 8.647(2.4); 8.638(2.5); 8.635(2.4); 8.546(5.9); 8.379(0.5); 8.317(0.7); 8.262(15.9); 8.246(1.0); 8.136(2.5); 8.133(2.3); 8.115(2.5); 8.112(2.4); 8.048(3.3); 7.646(1.8); 7.641(3.2); 7.629(3.7); 7.621(2.5); 7.609(2.1); 7.462(1.0); 7.458(0.7); 7.443(3.1); 7.439(2.1); 7.435(2.8); 7.415(2.6); 7.396(0.8); 5.096(0.4); 3.329(214.9); 2.675(1.2); 2.671(1.6); 2.666(1.1); 2.510(97.3); 2.506(188.9); 2.502(242.9); 2.497(174.6); 2.493(84.8); 2.333(1.1); 2.329(1.5); 2.324(1.1); 1.397(16.0); 0.146(0.5); 0.008(5.6); 0.000(122.9); −0.009(5.0); −0.150(0.6)

Example 2: $^1$H-NMR(400.0 MHz, d$_6$-DMSO): δ =
10.508(2.2); 8.827(2.6); 8.812(2.7); 8.589(3.3); 8.313(3.4); 7.918(2.3); 7.903(2.2); 7.869(1.9); 7.864(2.0); 7.673(0.7); 7.668(0.6); 7.652(1.4); 7.647(1.4); 7.615(2.5); 7.591(4.3); 3.326(46.8); 2.671(0.4); 2.506(51.5); 2.502(66.2); 2.498(50.1); 2.329(0.4); 2.128(16.0); 1.398(8.6); 0.146(0.4); 0.000(75.9); −0.150(0.4)

Example 3: $^1$H-NMR(400.0 MHz, d$_6$-DMSO): δ =
10.566(3.8); 8.813(5.9); 8.809(3.9); 8.802(3.8); 8.798(6.3); 8.537(7.0); 8.262(16.0); 8.051(3.5); 7.896(5.8); 7.892(3.9); 7.885(3.7); 7.881(5.8); 7.678(1.6); 7.659(1.9); 7.477(1.2); 7.473(0.9); 7.457(3.5); 7.447(3.0); 7.428(3.1); 7.409(1.0); 4.056(0.5); 4.038(1.5); 4.020(1.5); 4.003(0.5); 3.326(32.7); 2.511(17.9); 2.507(35.6); 2.503(47.2); 2.498(35.6); 1.989(6.4); 1.193(1.7); 1.175(3.4); 1.158(1.7); 0.008(2.5); 0.000(58.5); −0.008(3.0)

Example 4: $^1$H-NMR(400.0 MHz, d$_6$-DMSO): δ =
10.208(2.2); 8.580(3.3); 8.316(0.7); 8.305(3.4); 8.109(1.3); 8.104(0.6); 8.096(1.5); 8.087(1.6); 8.079(0.6); 8.073(1.4); 7.849(1.8); 7.844(2.0); 7.644(0.7); 7.639(0.6); 7.623(1.5); 7.618(1.5); 7.592(4.8); 7.572(1.3); 7.415(1.5); 7.393(2.9); 7.376(0.5); 7.371(1.4); 3.324(175.7); 2.675(1.0); 2.671(1.4); 2.666(1.1); 2.662(0.6); 2.524(3.3); 2.511(75.9); 2.506(157.4); 2.502(212.1); 2.497(158.1); 2.493(80.0); 2.333(1.0); 2.328(1.3); 2.324(1.0); 2.127(16.0); 2.098(0.4); 1.398(8.1); 0.008(0.8); 0.000(24.9); −0.008(1.1)

Example 5: $^1$H-NMR(400.0 MHz, d$_6$-DMSO): δ =
10.230(2.1); 8.509(3.3); 8.239(3.3); 8.098(1.3); 8.093(0.6); 8.085(1.5); 8.076(1.6); 8.068(0.6); 8.063(1.4); 7.844(0.8); 7.838(0.8); 7.825(0.8); 7.820(0.8); 7.607(0.5); 7.602(0.6); 7.587(4.1); 7.575(0.7); 7.569(0.5); 7.410(1.5); 7.405(0.5); 7.388(3.0); 7.370(1.4); 7.365(1.6); 7.349(0.9); 7.345(1.1); 7.323(0.8); 3.325(31.4); 2.675(0.3); 2.671(0.5); 2.666(0.3); 2.524(1.1); 2.511(25.3); 2.506(51.9); 2.502(69.0); 2.497(50.4); 2.493(24.6); 2.328(0.4); 2.324(0.3); 2.127(16.0); 1.398(5.4); 0.008(0.5); 0.000(13.7); −0.009(0.5)

Example 6: $^1$H-NMR(400.0 MHz, d$_6$-DMSO): δ =
10.514(1.9); 8.821(2.7); 8.817(1.7); 8.809(1.7); 8.805(2.9); 8.519(3.2); 8.245(3.3); 7.905(2.2); 7.902(1.5); 7.894(1.4); 7.890(2.1); 7.874(0.8); 7.869(0.8); 7.856(0.8); 7.851(0.8); 7.637(0.4); 7.631(0.4); 7.625(0.5); 7.619(0.5); 7.615(0.5); 7.610(0.6); 7.604(0.6); 7.598(0.7); 7.588(3.5); 7.396(0.9); 7.374(0.9); 7.371(1.0); 7.349(0.7); 4.038(0.4); 4.020(0.4); 3.326(38.2); 3.325(38.3); 2.675(0.4); 2.671(0.6); 2.666(0.4); 2.524(1.2); 2.519(1.9); 2.511(30.0); 2.506(62.9); 2.502(84.5); 2.497(61.1); 2.493(29.2); 2.333(0.4); 2.329(0.5); 2.324(0.4); 2.128(16.0); 1.989(1.7); 1.193(0.4); 1.175(0.9); 1.157(0.4); 0.008(0.3); 0.000(11.6); −0.009(0.4)

Example 7: $^1$H-NMR(400.0 MHz, d$_6$-DMSO): δ =
10.264(2.3); 8.513(2.0); 8.271(2.3); 8.113(1.2); 8.099(1.5); 8.091(1.6); 8.077(1.3); 7.822(0.7); 7.807(0.7); 7.786(0.4); 7.592(4.0); 7.428(1.4); 7.406(2.7); 7.384(1.4); 7.330(0.6); 7.308(1.1); 7.286(0.5); 3.326(27.0); 2.506(38.2); 2.502(49.1); 2.498(37.6); 2.121(16.0); 1.989(0.5); 1.398(9.2); 0.000(4.3)

Example 8: $^1$H-NMR(400.0 MHz, d$_6$-DMSO): δ =
10.290(2.2); 8.585(3.3); 8.309(3.4); 7.887(0.9); 7.868(1.1); 7.851(1.9); 7.846(2.0); 7.821(0.5); 7.815(0.7); 7.811(0.6); 7.796(0.6); 7.790(0.7); 7.656(0.7); 7.651(0.7); 7.635(1.7); 7.630(2.0); 7.613(0.9); 7.608(0.8); 7.602(3.0); 7.591(4.0); 7.581(1.6); 7.510(0.5); 7.505(0.4); 7.490(0.7); 7.484(0.7); 7.468(0.3); 3.325(29.0); 2.671(0.4); 2.524(1.1); 2.511(23.7); 2.506(49.2); 2.502(66.0); 2.497(48.5); 2.493(23.8); 2.328(0.4); 2.128(16.0); 1.398(3.5); 0.000(7.4)

Example 9: $^1$H-NMR(400.0 MHz, d$_6$-DMSO): δ =
10.583(2.1); 8.843(2.5); 8.839(1.7); 8.832(1.7); 8.828(2.7); 8.526(1.8); 8.524(1.9); 8.278(2.2); 7.922(2.2); 7.911(1.6); 7.907(2.2); 7.874(0.3); 7.859(0.5); 7.853(0.7); 7.838(0.7); 7.832(0.4); 7.816(0.3); 7.594(3.8); 7.357(0.5); 7.334(1.0); 7.314(0.5); 5.758(5.5); 3.332(6.8); 2.513(5.9); 2.508(11.9); 2.504(15.9); 2.499(11.7); 2.495(5.8); 2.124(16.0); 1.990(1.1); 1.176(0.6); 0.000(1.3)

Example 10: $^1$H-NMR(400.0 MHz, d$_6$-DMSO): δ =
10.056(1.2); 10.049(1.2); 8.589(2.6); 8.290(2.5); 8.013(1.1); 7.813(0.4); 7.796(0.9); 7.778(0.5); 7.633(0.6); 7.619(0.9); 7.592(7.4); 7.571(0.4); 7.407(0.6); 7.388(1.1); 7.371(1.4); 7.353(0.8); 3.326(32.1); 2.671(0.4); 2.502(55.8); 2.329(0.3); 2.131(16.0); 1.398(7.3); 0.000(2.3)

Example 11: $^1$H-NMR(400.0 MHz, d$_6$-DMSO): δ =
10.370(2.1); 8.714(2.1); 8.708(2.2); 8.423(3.4); 8.325(2.0); 8.319(2.0); 8.121(1.4); 8.116(0.6); 8.107(1.5); 8.099(1.6); 8.090(0.6); 8.085(1.5); 7.602(3.6); 7.439(1.5); 7.434(0.5); 7.417(2.9); 7.400(0.5); 7.395(1.4); 3.334(60.4); 2.676(0.5); 2.671(0.7); 2.666(0.5); 2.524(1.8); 2.519(2.7); 2.511(38.6); 2.506(79.4); 2.502(105.6); 2.497(77.2); 2.493(37.7); 2.333(0.5); 2.329(0.7); 2.324(0.5); 2.133(16.0); 1.398(4.9); 0.146(0.5); 0.008(3.3); 0.000(104.1); −0.009(3.5); −0.150(0.5)

Example 12: $^1$H-NMR(400.0 MHz, d$_6$-DMSO): δ =
8.845(2.8); 8.841(1.8); 8.834(1.8); 8.830(3.0); 8.734(2.1); 8.729(2.1); 8.704(3.3); 8.424(3.4); 8.357(2.3); 8.351(2.2); 7.926(2.8); 7.922(1.8); 7.915(1.7); 7.911(2.8); 7.603(3.7); 5.758(1.4); 3.329(9.0); 2.672(0.3); 2.525(0.9); 2.511(16.7); 2.507(33.6); 2.502(44.3); 2.498(32.5); 2.494(16.0); 2.134(16.0); 0.008(1.0); 0.000(31.3); −0.009(1.1)

Example 13: $^1$H-NMR(400.0 MHz, d$_6$-DMSO): δ =
10.107(1.2); 8.694(2.2); 8.688(2.2); 8.672(3.3); 8.389(3.3); 8.232(2.1); 8.226(2.1); 7.600(3.7); 6.712(1.9); 3.605(1.2); 3.587(2.5); 3.570(1.2); 3.325(16.2); 2.995(15.3); 2.951(0.6); 2.671(0.4); 2.549(0.4); 2.524(0.9); 2.511(20.1); 2.506(40.9); 2.502(54.3); 2.497(40.2); 2.493(19.9); 2.434(0.9); 2.416(1.9); 2.399(0.9); 2.329(0.3); 2.121(16.0); 1.796(0.7); 1.782(1.7); 1.773(2.5); 1.764(1.2); 1.727(0.4); 1.691(1.2); 1.681(2.5); 1.672(1.7); 1.658(0.7); 1.423(0.6); 1.398(0.3); 1.235(0.3); 0.008(1.1); 0.000(35.3); −0.009(1.4)

Example 14: $^1$H-NMR(400.0 MHz, d$_6$-DMSO): δ =
10.846(1.9); 8.751(3.3); 8.401(2.1); 8.389(1.6); 8.371(3.7); 8.151(1.4); 8.145(0.6); 8.137(1.6); 8.128(1.6); 8.120(0.6); 8.115(1.5); 7.604(3.7); 7.477(1.1); 7.473(1.2); 7.464(1.1); 7.460(1.2); 7.380(1.5); 7.357(2.9); 7.340(0.5); 7.335(1.5); 5.758(0.8); 4.038(0.4); 4.020(0.4); 3.324(18.9); 3.175(0.4); 3.162(0.4); 2.671(0.4); 2.524(1.1); 2.511(23.2); 2.507(47.3); 2.502(62.9); 2.498(46.8); 2.493(23.5); 2.329(0.4); 2.134(16.0); 1.989(1.6); 1.193(0.4); 1.175(0.8); 1.157(0.4); 0.008(2.0); 0.000(58.5); −0.008(2.2)

Example 15: $^1$H-NMR(400.0 MHz, d$_6$-DMSO): δ =
10.626(2.0); 9.397(3.6); 9.300(6.0); 8.516(3.3); 8.316(0.5); 8.229(3.4); 7.944(0.8); 7.938(0.8); 7.925(0.8); 7.920(0.8); 7.630(0.4); 7.624(0.5); 7.618(0.5); 7.612(0.5); 7.609(0.6); 7.603(0.7); 7.589(3.8); 7.409(0.9); 7.387(0.8); 7.383(1.0); 7.362(0.7); 4.038(0.3); 4.020(0.3); 3.323(131.1); 2.675(1.0); 2.671(1.7); 2.666(1.3); 2.524(4.3); 2.510(88.3); 2.506(185.2); 2.501(251.6); 2.497(189.6); 2.493(96.7); 2.333(1.1); 2.328(1.6); 2.324(1.2); 2.128(16.0); 1.989(1.5); 1.233(0.4); 1.193(0.5); 1.175(0.8); 1.157(0.5); 0.146(1.0); 0.008(6.9); 0.000(227.9); −0.009(9.3); −0.150(1.0)

Example 16: $^1$H-NMR(400.0 MHz, d$_6$-DMSO): δ =
10.622(1.9); 9.460(2.0); 9.457(2.1); 9.178(2.1); 9.166(2.1); 8.521(3.2); 8.228(3.3); 8.175(0.4); 8.165(1.4); 8.161(1.4); 8.152(2.2); 8.149(2.1); 8.137(0.9); 8.132(0.8); 8.101(0.3); 8.080(0.4); 7.607(0.5); 7.589(4.3); 7.573(0.7); 7.568(0.7); 7.419(0.9); 7.398(0.9); 7.393(1.0); 7.372(0.7); 6.640(0.9); 3.324(33.3); 2.671(0.4); 2.511(22.2); 2.507(43.2); 2.502(56.2); 2.498(41.9); 2.494(21.3); 2.329(0.4); 2.132(16.0); 2.111(0.4); 1.989(0.7); 1.398(1.0); 1.175(0.4);

TABLE 4-continued

NMR peak list (1)

0.008(2.3); 0.000(50.8); −0.008(2.3)
Example 78: 1H-NMR(400.0 MHz, d6-DMSO): δ =
10.211(2.1); 8.514(2.1); 8.274(2.2); 8.100(1.4); 8.086(1.6); 8.078(1.7); 8.064(1.4); 8.009(0.4); 8.001(0.4); 7.987(0.3); 7.708(0.5); 7.691(1.0); 7.674(0.6); 7.592(4.1); 7.492(0.5); 7.474(1.0); 7.456(0.6); 7.404(1.5); 7.382(2.8); 7.360(1.4); 7.342(0.3); 7.319(0.6); 7.297(0.4); 7.287(0.9); 7.268(1.5); 7.248(0.7); 3.320(10.8); 2.507(18.6); 2.503(23.5); 2.498(17.7); 2.130(16.0); 1.398(11.4); 0.000(24.6)
Example 79: 1H-NMR(400.0 MHz, d6-DMSO): δ =
10.418(2.1); 9.153(1.7); 9.149(1.7); 8.795(1.2); 8.792(1.2); 8.783(1.3); 8.779(1.2); 8.524(2.1); 8.345(1.0); 8.340(0.7); 8.330(0.7); 8.325(1.0); 8.321(0.7); 8.281(2.3); 7.725(0.5); 7.709(1.0); 7.691(0.6); 7.604(1.2); 7.594(4.9); 7.574(0.9); 7.539(0.5); 7.521(1.0); 7.504(0.6); 7.304(0.9); 7.285(1.5); 7.265(0.7); 5.754(4.5); 3.321(10.1); 2.507(14.4); 2.503(18.3); 2.499(13.8); 2.132(16.0); 1.989(1.1); 1.176(0.6); 1.072(0.7); 0.000(20.7)
Example 80: 1H-NMR(400.0 MHz, d6-DMSO): δ =
10.493(2.2); 8.817(2.7); 8.813(1.9); 8.806(1.8); 8.802(3.0); 8.524(2.0); 8.280(2.2); 7.907(2.5); 7.903(1.8); 7.896(1.7); 7.892(2.6); 7.738(0.5); 7.721(0.9); 7.705(0.5); 7.701(0.5); 7.593(3.9); 7.522(0.4); 7.504(0.9); 7.488(0.5); 7.309(0.8); 7.290(1.5); 7.270(0.7); 5.753(8.6); 3.320(14.4); 3.179(0.5); 3.166(0.5); 2.892(0.5); 2.733(0.5); 2.507(12.4); 2.503(17.5); 2.499(13.4); 2.131(16.0); 1.989(0.5); 0.000(3.1)

TABLE 5

NMR peak list (2)

| Example number | NMR-peak list |
|---|---|
| 17 | 1H-NMR (400 MHz, DMSO-d6) delta [ppm]: −0.149 (0.49), −0.008 (4.55), 0.008 (3.94), 0.146 (0.49), 2.322 (0.42), 2.327 (0.54), 2.366 (0.84), 2.456 (16.00), 2.522 (1.28), 2.665 (0.39), 2.669 (0.57), 2.674 (0.44), 2.709 (0.84), 7.380 (2.83), 7.386 (0.91), 7.397 (1.11), 7.403 (5.86), 7.408 (1.13), 7.419 (0.96), 7.425 (3.03), 8.021 (3.18), 8.027 (3.15), 8.074 (2.86), 8.079 (1.40), 8.087 (4.80), 8.092 (11.77), 8.096 (5.44), 8.104 (1.38), 8.110 (2.78), 8.435 (5.93), 8.437 (6.18), 8.717 (3.69), 8.722 (3.67), 8.735 (6.01), 8.737 (6.13), 10.164 (4.04), |
| 18 | 1H-NMR (400 MHz, DMSO-d6) delta [ppm]: −0.141 (1.75), −0.000 (15.95), 0.016 (14.47), 0.154 (1.81), 1.156 (0.77), 2.335 (1.64), 2.374 (2.25), 2.473 (16.00), 2.677 (1.86), 2.718 (2.36), 3.293 (1.59), 7.912 (4.11), 7.927 (4.44), 8.059 (3.01), 8.064 (3.12), 8.101 (10.03), 8.447 (5.81), 8.751 (8.16), 8.825 (4.71), 8.829 (3.23), 8.836 (3.07), 8.840 (4.66), 10.437 (4.00). |
| 19 | 1H-NMR (400 MHz, DMSO-d6) delta [ppm]: −0.149 (0.95), −0.008 (7.93), 0.008 (7.34), 0.146 (0.91), 1.237 (0.41), 2.323 (0.59), 2.328 (0.82), 2.332 (0.68), 2.366 (1.59), 2.524 (2.13), 2.665 (0.63), 2.670 (0.91), 2.674 (0.68), 2.710 (1.63), 3.287 (1.04), 5.527 (7.89), 7.315 (2.90), 7.320 (3.04), 7.341 (2.95), 7.347 (2.99), 7.641 (3.22), 7.647 (5.89), 7.652 (3.04), 7.889 (6.48), 7.893 (3.94), 7.900 (3.99), 7.904 (6.71), 8.078 (16.00), 8.099 (11.69), 8.248 (9.56), 8.250 (9.34), 8.454 (7.03), 8.456 (7.25), 8.467 (9.38), 8.486 (2.36), 8.491 (1.54), 8.571 (9.20), 8.573 (9.56), 8.764 (6.48), 8.766 (6.75), 8.818 (6.39), 8.822 (3.81), 8.829 (3.72), 8.833 (6.12), 10.710 (1.86). |
| 20 | 1H-NMR (400 MHz, DMSO-d6) delta [ppm]: −0.008 (1.44), 0.008 (1.27), 2.127 (12.94), 2.684 (16.00), 7.208 (1.14), 7.229 (1.30), 7.479 (0.89), 7.484 (0.87), 7.500 (0.72), 7.505 (0.74), 7.577 (2.90), 7.881 (1.48), 7.886 (1.07), 7.892 (1.11), 7.897 (1.52), 8.017 (1.13), 8.022 (1.10), 8.159 (2.44), 8.160 (2.35), 8.426 (2.51), 8.428 (2.44), 8.797 (1.97), 8.801 (1.21), 8.808 (1.22), 8.812 (1.86), 9.924 (1.48). |
| 21 | 1H-NMR (400 MHz, DMSO-d6) delta [ppm]: −0.008 (0.92), 0.008 (0.90), 2.126 (11.89), 2.519 (0.43), 2.678 (16.00), 7.210 (1.22), 7.231 (1.40), 7.363 (1.06), 7.380 (0.46), 7.385 (2.17), 7.391 (0.45), 7.408 (1.12), 7.446 (0.82), 7.452 (0.82), 7.467 (0.67), 7.473 (0.70), 7.576 (2.69), 8.044 (1.07), 8.050 (0.48), 8.058 (1.26), 8.064 (2.01), 8.066 (2.00), 8.070 (1.56), 8.075 (0.58), 8.080 (1.02), 8.148 (2.19), 8.150 (2.34), 8.417 (2.22), 8.419 (2.28), 9.652 (1.45). |
| 22 | 1H-NMR (400 MHz, DMSO-d6) delta [ppm]: −0.008 (0.43), 0.008 (0.44), 3.937 (16.00), 7.350 (1.03), 7.368 (1.45), 7.371 (1.58), 7.376 (1.24), 7.389 (1.56), 7.396 (2.16), 7.417 (1.40), 7.571 (0.65), 7.577 (0.73), 7.583 (0.76), 7.589 (0.75), 7.593 (0.69), 7.599 (0.69), 7.604 (0.61), 7.610 (0.64), 7.616 (0.73), 7.622 (0.80), 7.627 (0.80), 7.633 (0.80), 7.637 (0.69), 7.643 (0.74), 7.649 (0.64), 7.654 (0.63), 7.764 (1.23), 7.769 (1.17), 7.784 (1.23), 7.790 (1.15), 7.826 (1.14), 7.831 (1.14), 7.844 (1.16), 7.850 (1.07), 8.084 (7.03), 8.338 (4.17), 8.340 (4.18), 8.636 (4.10), 8.638 (4.14), 10.221 (2.95). |
| 23 | 1H-NMR (400 MHz, DMSO-d6) delta [ppm]: −0.008 (1.78), 0.008 (1.65), 1.148 (0.43), 2.138 (16.00), 2.150 (12.05), 2.328 (0.48), 2.367 (0.78), 2.670 (0.48), 2.710 (0.78), 3.289 (1.21), 3.335 (0.95), 5.272 (4.99), 5.885 (1.78), 6.881 (0.52), 6.896 (0.69), 6.903 (1.21), 6.918 (1.43), 6.922 (1.52), 6.938 (2.34), 6.942 (1.73), 6.964 (1.95), 6.968 (1.39), 6.988 (0.69), 7.295 (3.25), 7.300 (2.91), 7.316 (1.34), 7.318 (1.34), 7.321 (1.21), 7.341 (0.69), 7.343 (0.69), 7.381 (2.12), 7.386 (0.74), 7.403 (4.38), 7.420 (0.74), 7.425 (2.30), 7.654 (1.60), 7.659 (1.56), 7.794 (0.48), 7.809 (0.61), 7.815 (0.95), 7.830 (0.95), 7.837 (0.65), 7.852 (0.48), 7.911 (3.60), 7.919 (1.95), 8.074 (2.08), 8.079 (0.95), 8.088 (2.34), 8.096 (2.38), 8.104 (0.95), 8.110 (2.12), 8.187 (2.60), 8.203 (2.17), 8.213 (4.38), 8.217 (3.38), 8.341 (3.64), 8.440 (2.78), 8.446 (2.64), 8.572 (2.25), 10.258 (3.64). |
| 24 | 1H-NMR (400 MHz, DMSO-d6) delta [ppm]: −0.008 (0.84), 0.008 (0.77), 2.163 (10.26), 3.288 (0.64), 3.939 (16.00), 7.396 (1.19), 7.417 (1.46), 7.424 (1.23), 7.445 (1.39), 7.643 (0.69), 7.648 (0.82), 7.654 (0.80), 7.659 (0.84), 7.664 (0.69), 7.669 (0.73), 7.675 (0.62), 7.681 (0.66), 7.772 (1.25), 7.777 (1.19), 7.793 (1.23), 7.798 (1.12), 7.933 (1.78), 8.219 (1.80), 8.314 (2.98), 8.320 (3.08), 8.484 (4.01), 8.485 (4.63), 8.716 (2.99), 8.722 (2.98), 8.778 (3.56), 10.357 (3.01). |
| 25 | 1H-NMR (400 MHz, DMSO-d6) delta [ppm]: −0.149 (0.99), −0.008 (9.64), 0.008 (7.24), 0.146 (0.93), 1.147 (0.64), 2.073 (0.47), 2.150 (16.00), 2.366 (2.22), 2.558 (1.52), 2.671 (0.70), 2.710 (2.28), 3.287 (2.63), 7.320 (0.93), 7.341 (1.87), 7.344 (1.99), 7.366 (0.99), 7.821 (0.64), 7.842 (1.23), 7.857 (1.28), 7.879 (0.64), 7.900 (4.79), 7.904 (3.33), 7.911 (4.91), 7.915 (7.59), 8.200 (2.80), 8.347 (5.02), 8.583 (3.27), 8.822 (5.66), 8.827 (3.39), 8.833 (3.56), 8.838 (5.20), 10.574 (3.50). |
| 26 | 1H-NMR (400 MHz, DMSO-d6) delta [ppm]: −0.149 (0.55), −0.008 (4.90), 0.008 (4.45), 0.146 (0.55), 2.138 (10.12), 2.150 (16.00), 2.367 (0.67), 2.710 (0.71), 3.288 (0.91), 5.273 (3.13), 6.896 (0.43), 6.903 (0.75), 6.918 (0.89), 6.922 (0.89), 6.938 (1.50), 6.964 (1.20), 6.988 (0.45), 7.245 (2.38), 7.255 (2.58), 7.267 (2.48), 7.297 (0.94), 7.299 (0.89), 7.318 (1.85), 7.320 (1.89), 7.322 (1.81), 7.340 (1.04), 7.795 (0.69), 7.810 (0.89), 7.817 (1.26), 7.831 (1.28), 7.838 (0.77), 7.853 (0.65), 7.900 (2.91), 7.903 (3.90), 7.912 (5.55), 7.916 (5.61), 8.019 (2.52), 8.022 (2.58), 8.029 (2.62), 8.032 (2.34), 8.187 (1.69), 8.201 (2.93), 8.214 (2.97), 8.343 (4.88), 8.441 (1.81), 8.446 (1.65), 8.578 (2.93), 8.584 (2.60), 10.260 (4.84). |

TABLE 5-continued

NMR peak list (2)

| Example number | NMR-peak list |
|---|---|
| 27 | 1H-NMR (400 MHz, DMSO-d6) delta [ppm]: −0.008 (2.53), 0.008 (2.23), 2.073 (1.39), 2.139 (4.48), 2.151 (10.87), 2.367 (0.44), 2.711 (0.44), 3.288 (0.56), 3.936 (16.00), 5.272 (1.32), 6.938 (0.66), 6.964 (0.53), 7.301 (0.60), 7.303 (0.64), 7.323 (1.27), 7.325 (1.31), 7.327 (1.21), 7.346 (0.68), 7.348 (0.68), 7.350 (0.64), 7.383 (1.18), 7.404 (1.48), 7.410 (1.24), 7.432 (1.38), 7.630 (0.68), 7.635 (0.79), 7.641 (0.78), 7.646 (0.79), 7.651 (0.68), 7.656 (0.72), 7.662 (0.64), 7.667 (0.62), 7.768 (1.24), 7.774 (1.17), 7.789 (1.26), 7.794 (1.29), 7.813 (0.60), 7.819 (0.88), 7.834 (0.89), 7.841 (0.59), 7.856 (0.44), 7.904 (0.71), 7.921 (1.67), 8.186 (0.74), 8.201 (1.92), 8.214 (1.30), 8.217 (0.92), 8.345 (3.40), 8.441 (0.80), 8.446 (0.73), 8.577 (2.10), 8.583 (1.84), 10.249 (3.29). |
| 28 | 1H-NMR (500 MHz, DICHLOROMETHANE-d2) delta [ppm]: 0.862 (1.34), 0.876 (1.50), 0.881 (1.56), 0.891 (1.02), 1.265 (5.16), 1.524 (13.20), 2.167 (12.03), 3.970 (16.00), 5.331 (7.63), 5.332 (11.90), 7.183 (1.30), 7.191 (1.28), 7.199 (1.75), 7.204 (1.64), 7.209 (1.86), 7.213 (1.47), 7.221 (1.71), 7.230 (1.60), 7.307 (0.82), 7.312 (1.00), 7.317 (1.01), 7.321 (1.03), 7.329 (0.83), 7.334 (0.75), 7.339 (0.71), 7.395 (0.75), 7.400 (0.96), 7.404 (1.04), 7.408 (0.91), 7.412 (0.90), 7.417 (0.90), 7.421 (0.82), 7.425 (0.78), 7.592 (1.38), 7.597 (1.42), 7.609 (1.39), 7.613 (1.36), 7.842 (2.19), 7.852 (3.86), 7.910 (2.06), 8.070 (4.14), 8.071 (4.07), 8.642 (1.24), 8.646 (1.37), 8.657 (1.37), 8.661 (1.30). |
| 29 | 1H-NMR (500 MHz, DICHLOROMETHANE-d2) delta [ppm]: 1.266 (1.01), 1.387 (1.02), 1.401 (2.10), 1.415 (1.04), 1.457 (6.15), 1.470 (12.66), 1.484 (6.20), 1.538 (3.66), 2.142 (2.79), 2.167 (16.00), 4.043 (0.94), 4.057 (0.92), 4.177 (1.86), 4.191 (5.72), 4.205 (5.60), 4.219 (1.72), 5.332 (4.75), 7.176 (1.86), 7.187 (1.70), 7.193 (2.36), 7.197 (2.06), 7.204 (2.36), 7.208 (1.86), 7.214 (2.72), 7.225 (2.15), 7.231 (0.64), 7.250 (0.56), 7.304 (1.14), 7.308 (1.19), 7.313 (1.24), 7.318 (1.25), 7.321 (1.05), 7.325 (0.98), 7.330 (0.89), 7.335 (0.85), 7.385 (1.09), 7.390 (1.21), 7.394 (1.20), 7.398 (1.20), 7.402 (1.04), 7.407 (1.12), 7.411 (1.25), 7.415 (1.21), 7.574 (1.93), 7.578 (1.82), 7.584 (0.40), 7.590 (1.92), 7.594 (1.82), 7.781 (0.71), 7.843 (2.78), 7.850 (4.29), 7.851 (4.74), 7.853 (3.40), 7.911 (2.67), 7.916 (2.07), 7.992 (0.92), 7.994 (0.93), 8.040 (1.27), 8.047 (1.25), 8.068 (5.50), 8.070 (5.56), 8.638 (1.67), 8.643 (1.65), 8.653 (1.68), 8.658 (1.57), 9.366 (0.83), 9.367 (0.79). |
| 30 | 1H-NMR (400 MHz, DMSO-d6) delta [ppm]: −0.149 (1.00), −0.008 (9.17), 0.008 (7.82), 0.146 (1.00), 0.648 (1.53), 0.658 (4.73), 0.665 (4.80), 0.674 (1.67), 1.080 (1.53), 1.088 (4.02), 1.095 (3.84), 1.104 (1.32), 1.146 (0.50), 1.407 (16.00), 2.142 (13.40), 2.328 (0.46), 2.366 (0.39), 2.670 (0.50), 3.287 (1.60), 7.256 (1.39), 7.277 (1.85), 7.281 (1.60), 7.303 (1.60), 7.497 (0.85), 7.503 (0.96), 7.508 (0.96), 7.514 (1.00), 7.518 (0.89), 7.524 (0.89), 7.530 (0.78), 7.536 (0.78), 7.690 (1.46), 7.696 (1.49), 7.708 (1.53), 7.714 (1.42), 7.916 (2.28), 8.195 (2.31), 8.266 (5.12), 8.268 (5.58), 8.541 (4.52), 9.122 (3.48). |
| 31 | 1H-NMR (400 MHz, DMSO-d6) delta [ppm]: −0.149 (1.21), −0.008 (10.77), 0.008 (9.56), 0.146 (1.25), 1.147 (0.82), 2.085 (0.51), 2.153 (16.00), 2.327 (0.74), 2.332 (0.59), 2.523 (1.29), 2.665 (0.62), 2.669 (0.82), 3.286 (1.83), 7.327 (1.56), 7.348 (2.30), 7.352 (1.83), 7.374 (1.87), 7.555 (0.94), 7.561 (1.09), 7.566 (1.13), 7.572 (1.17), 7.577 (1.05), 7.582 (1.05), 7.588 (0.94), 7.594 (0.86), 7.627 (1.83), 7.630 (1.95), 7.639 (3.59), 7.643 (3.63), 7.660 (3.32), 7.668 (3.40), 7.673 (1.68), 7.680 (1.72), 7.816 (1.76), 7.821 (1.72), 7.834 (1.76), 7.840 (1.64), 7.920 (2.85), 7.922 (2.50), 8.200 (2.85), 8.298 (6.36), 8.300 (6.24), 8.372 (2.58), 8.375 (2.85), 8.379 (2.73), 8.382 (2.50), 8.575 (5.23), 10.019 (4.49). |
| 32 | 1H-NMR (400 MHz, DMSO-d6) delta [ppm]: −0.008 (0.98), 0.001 (16.00), 0.009 (0.71), 2.156 (3.00), 3.842 (4.32), 7.353 (0.41), 7.458 (0.65), 7.540 (0.42), 7.545 (0.61), 7.551 (0.43), 7.578 (0.69), 7.595 (0.50), 7.915 (0.53), 7.918 (0.58), 8.197 (0.55), 8.302 (1.36), 8.577 (1.03), 10.167 (0.85). |
| 33 | 1H-NMR (500 MHz, DMSO-d6) delta [ppm]: −0.007 (2.77), 0.007 (2.16), 1.147 (0.49), 1.236 (0.73), 2.145 (1.47), 2.154 (16.00), 2.362 (0.53), 2.519 (0.65), 2.523 (0.45), 2.635 (0.53), 3.289 (1.91), 3.334 (0.49), 7.356 (1.47), 7.373 (1.99), 7.377 (1.75), 7.394 (1.63), 7.591 (0.94), 7.596 (1.10), 7.600 (1.14), 7.604 (1.15), 7.608 (1.06), 7.613 (1.02), 7.617 (0.90), 7.622 (0.81), 7.851 (1.63), 7.856 (1.67), 7.866 (1.79), 7.870 (1.59), 7.916 (2.65), 7.921 (2.77), 8.038 (4.52), 8.042 (1.83), 8.051 (2.20), 8.055 (6.64), 8.135 (5.37), 8.139 (2.12), 8.148 (1.75), 8.152 (3.79), 8.199 (2.81), 8.300 (5.98), 8.302 (6.55), 8.577 (5.37), 10.475 (4.19). |
| 35 | 1H-NMR (500 MHz, DMSO-d6) delta [ppm]: −0.007 (1.26), 0.007 (1.14), 1.236 (0.43), 2.154 (11.71), 3.283 (0.40), 3.289 (0.80), 3.293 (0.91), 3.297 (1.26), 3.300 (1.94), 3.322 (2.91), 3.324 (2.51), 3.337 (0.57), 4.024 (16.00), 7.366 (1.06), 7.382 (1.40), 7.386 (1.31), 7.403 (1.20), 7.601 (0.69), 7.606 (0.80), 7.610 (0.83), 7.615 (0.80), 7.618 (0.77), 7.623 (0.74), 7.627 (0.66), 7.632 (0.63), 7.668 (1.29), 7.671 (1.40), 7.684 (1.46), 7.687 (1.57), 7.765 (2.71), 7.768 (2.74), 7.835 (1.23), 7.840 (1.26), 7.850 (1.26), 7.854 (1.20), 7.917 (2.00), 7.924 (4.49), 7.940 (2.69), 8.201 (2.00), 8.306 (4.46), 8.307 (4.91), 8.585 (3.94), 10.457 (3.31). |
| 36 | 1H-NMR (400 MHz, DMSO-d6) delta [ppm]: −0.008 (1.45), 0.008 (1.25), 0.695 (0.61), 0.704 (1.78), 0.711 (1.82), 0.721 (0.70), 1.099 (0.62), 1.107 (1.59), 1.115 (1.50), 1.124 (0.54), 1.455 (5.80), 2.133 (5.51), 2.661 (16.00), 7.250 (1.07), 7.271 (1.61), 7.339 (0.95), 7.344 (0.95), 7.360 (0.60), 7.365 (0.62), 7.901 (0.95), 7.903 (0.83), 8.142 (2.15), 8.144 (2.28), 8.177 (0.95), 8.295 (1.44), 8.300 (1.45), 8.433 (1.86), 8.950 (1.13). |
| 37 | 1H-NMR (400 MHz, DMSO-d6) delta [ppm]: −0.149 (0.43), −0.008 (3.54), 0.008 (3.06), 2.150 (5.46), 2.680 (16.00), 3.286 (0.86), 7.199 (1.19), 7.220 (1.39), 7.428 (0.83), 7.433 (0.82), 7.449 (0.66), 7.454 (0.67), 7.604 (0.84), 7.608 (0.86), 7.617 (1.10), 7.620 (1.15), 7.670 (1.11), 7.677 (1.13), 7.682 (0.79), 7.690 (0.78), 7.905 (0.92), 8.029 (1.36), 8.034 (1.35), 8.188 (0.96), 8.206 (2.35), 8.208 (2.27), 8.363 (0.98), 8.366 (1.10), 8.370 (1.05), 8.374 (0.90), 8.479 (1.88), 9.444 (1.37). |
| 38 | 1H-NMR (400 MHz, DMSO-d6) delta [ppm]: −0.008 (1.12), 0.008 (0.95), 3.312 (16.00), 3.362 (14.17), 3.668 (5.33), 6.898 (0.42), 6.932 (0.48), 7.083 (0.52), 7.104 (0.67), 7.111 (0.78), 7.128 (1.18), 7.146 (0.97), 7.149 (0.89), 7.227 (0.65), 7.249 (1.09), 7.274 (0.71), 7.586 (0.61), 7.592 (0.72), 7.598 (0.75), 7.603 (0.77), 7.605 (0.74), 7.608 (0.73), 7.614 (0.68), 7.619 (0.62), 7.625 (0.54), 7.949 (1.30), 7.955 (1.32), 7.968 (1.33), 7.974 (1.25), 8.475 (5.01), 8.697 (4.39). |
| 39 | 1H-NMR (400 MHz, DMSO-d6) delta [ppm]: −0.008 (1.13), 0.008 (0.94), 2.156 (16.00), 7.356 (1.61), 7.375 (2.15), 7.377 (3.38), 7.382 (3.57), 7.396 (1.88), 7.403 (3.64), 7.586 (1.01), 7.592 (1.16), 7.597 (1.21), 7.603 (1.20), 7.607 (1.10), 7.613 (1.09), 7.619 (0.97), 7.625 (0.93), 7.867 (1.78), 7.872 (1.79), 7.885 (1.84), 7.890 (1.72), 7.917 (2.67), 7.921 (2.79), 7.923 (2.53), 8.200 (2.72), 8.298 (6.55), 8.300 (6.50), 8.506 (0.99), 8.513 (1.02), 8.525 (1.40), 8.527 (1.49), 8.532 (1.56), 8.534 (1.43), 8.547 (0.97), 8.553 (0.97), 8.579 (5.38), 8.851 (2.70), 8.857 (2.59), 10.456 (4.76). |
| 40 | 1H-NMR (400 MHz, DMSO-d6) delta [ppm]: −0.008 (2.10), 0.008 (1.89), 2.151 (16.00), 7.317 (0.90), 7.319 (0.94), 7.321 (0.94), 7.339 (1.85), 7.341 (1.91), 7.343 (1.85), 7.362 (0.99), 7.363 (1.01), 7.366 (0.95), 7.397 (1.69), 7.403 (1.65), 7.418 (1.79), 7.425 (1.68), 7.814 (0.68), 7.830 (0.88), 7.836 (1.35), 7.851 (1.31), 7.858 (0.85), 7.873 (0.68), 7.919 (2.81), 7.921 (2.48), 8.201 (2.72), 8.346 (4.90), 8.524 (0.95), 8.531 (1.01), 8.544 (1.39), 8.546 (1.49), 8.552 (1.47), 8.565 (1.01), 8.572 (1.14), 8.580 (3.06), 8.586 (2.71), 8.874 (2.76), 8.881 (2.70), 10.509 (4.92). |

TABLE 5-continued

NMR peak list (2)

| Example number | NMR-peak list |
|---|---|
| 41 | 1H-NMR (400 MHz, DMSO-d6) delta [ppm]: −0.149 (0.53), −0.008 (4.82), 0.008 (4.05), 0.146 (0.53), 1.150 (0.98), 2.126 (12.30), 2.152 (0.80), 3.286 (0.69), 3.336 (1.17), 3.350 (16.00), 5.754 (0.78), 7.128 (1.36), 7.135 (1.41), 7.150 (1.47), 7.156 (1.43), 7.215 (0.79), 7.238 (1.63), 7.240 (1.53), 7.261 (0.85), 7.753 (0.56), 7.768 (0.73), 7.775 (1.16), 7.790 (1.11), 7.797 (0.72), 7.812 (0.56), 7.904 (1.01), 7.911 (2.62), 7.912 (3.08), 7.932 (1.40), 7.945 (0.73), 7.951 (0.72), 8.161 (2.22), 8.168 (2.08), 8.199 (2.85), 8.201 (2.78), 8.269 (3.35), 8.533 (2.90). |
| 42 | 1H-NMR (400 MHz, DMSO-d6) delta [ppm]: −0.008 (1.47), 0.008 (1.41), 2.157 (16.00), 3.287 (0.95), 5.754 (0.48), 7.280 (1.39), 7.300 (3.00), 7.319 (1.69), 7.371 (1.70), 7.377 (1.74), 7.392 (1.80), 7.399 (1.74), 7.519 (0.96), 7.524 (1.03), 7.540 (1.75), 7.543 (1.52), 7.557 (0.85), 7.559 (0.79), 7.562 (0.79), 7.694 (0.96), 7.698 (1.04), 7.711 (1.49), 7.714 (1.81), 7.731 (0.97), 7.735 (0.84), 7.921 (2.89), 7.923 (2.56), 8.201 (2.51), 8.204 (2.87), 8.350 (4.77), 8.503 (0.97), 8.510 (1.00), 8.523 (1.58), 8.530 (1.66), 8.544 (0.95), 8.550 (0.95), 8.586 (3.02), 8.591 (2.78), 8.848 (2.75), 8.854 (2.66), 10.444 (4.42). |
| 43 | 1H-NMR (400 MHz, DMSO-d6) delta [ppm]: −0.008 (1.80), 0.008 (1.54), 2.158 (16.00), 3.288 (0.91), 7.262 (1.36), 7.281 (2.96), 7.301 (1.71), 7.483 (0.91), 7.487 (1.07), 7.501 (1.56), 7.504 (1.77), 7.506 (1.67), 7.524 (2.09), 7.527 (2.23), 7.531 (0.85), 7.544 (4.94), 7.548 (2.56), 7.560 (1.56), 7.564 (3.66), 7.595 (1.10), 7.599 (2.02), 7.603 (1.20), 7.612 (0.77), 7.617 (2.45), 7.624 (0.53), 7.632 (0.51), 7.636 (0.72), 7.674 (0.95), 7.678 (1.00), 7.691 (1.49), 7.694 (1.81), 7.711 (0.96), 7.715 (0.83), 7.920 (2.88), 7.922 (2.62), 7.990 (3.60), 7.994 (4.73), 7.999 (1.23), 8.007 (2.09), 8.011 (4.24), 8.014 (3.01), 8.020 (0.47), 8.202 (2.88), 8.347 (4.75), 8.579 (3.04), 8.584 (2.74), 10.178 (4.25). |
| 44 | 1H-NMR (400 MHz, DMSO-d6) delta [ppm]: −0.008 (2.67), 0.008 (3.34), 2.116 (13.55), 3.287 (2.37), 3.344 (1.68), 3.375 (16.00), 3.780 (1.00), 5.754 (0.49), 7.116 (0.72), 7.217 (0.72), 7.237 (1.44), 7.257 (0.91), 7.383 (0.92), 7.402 (1.54), 7.403 (1.49), 7.421 (0.77), 7.686 (0.81), 7.705 (1.43), 7.723 (0.80), 7.911 (3.66), 8.189 (3.30), 8.192 (3.50), 8.249 (2.76), 8.264 (0.57), 8.493 (2.37). |
| 45 | 1H-NMR (400 MHz, DMSO-d6) delta [ppm]: −0.008 (0.77), 0.000 (16.00), 0.008 (0.94), 2.117 (5.23), 3.287 (0.46), 3.310 (6.38), 7.172 (0.46), 7.249 (0.60), 7.278 (0.88), 7.297 (1.01), 7.316 (1.01), 7.336 (0.58), 7.645 (0.44), 7.909 (1.10), 7.911 (0.99), 8.186 (1.08), 8.188 (1.12), 8.228 (0.97), 8.493 (0.96), 8.495 (1.00). |
| 46 | 1H-NMR (400 MHz, DMSO-d6) delta [ppm]: −0.008 (1.19), 0.000 (16.00), 0.008 (1.08), 0.013 (0.59), 2.155 (1.53), 7.918 (0.48), 8.294 (0.61), 8.579 (0.52), 10.673 (0.41). |
| 47 | 1H-NMR (400 MHz, DMSO-d6) delta [ppm]: −0.008 (2.30), 0.008 (1.90), 2.156 (10.69), 2.226 (10.07), 3.286 (0.98), 3.880 (16.00), 5.754 (0.41), 7.289 (1.27), 7.292 (1.39), 7.310 (1.52), 7.312 (1.69), 7.330 (1.08), 7.352 (1.44), 7.356 (1.24), 7.377 (1.24), 7.524 (1.19), 7.529 (1.84), 7.540 (2.26), 7.545 (4.98), 7.563 (0.69), 7.569 (0.78), 7.575 (0.80), 7.581 (0.79), 7.585 (0.72), 7.591 (0.71), 7.596 (0.63), 7.602 (0.61), 7.812 (1.14), 7.818 (1.18), 7.831 (1.19), 7.836 (1.11), 7.916 (1.76), 7.921 (1.86), 7.922 (1.68), 8.199 (1.73), 8.200 (1.86), 8.305 (3.99), 8.307 (4.47), 8.582 (3.61), 10.112 (3.09). |
| 48 | 1H-NMR (400 MHz, DMSO-d6) delta [ppm]: −0.008 (1.20), 0.008 (1.19), 2.073 (0.57), 2.142 (13.31), 2.366 (0.50), 2.710 (0.51), 3.287 (2.65), 3.395 (16.00), 7.123 (0.76), 7.146 (0.80), 7.201 (0.61), 7.224 (1.05), 7.248 (0.67), 7.557 (0.63), 7.596 (0.65), 7.906 (1.66), 7.912 (1.91), 7.925 (4.39), 7.931 (2.61), 8.206 (3.44), 8.312 (5.76), 8.553 (4.34). |
| 49 | 1H-NMR (400 MHz, DMSO-d6) delta [ppm]: −0.149 (0.79), −0.008 (6.75), 0.008 (6.43), 0.146 (0.74), 1.146 (0.69), 1.266 (1.16), 2.154 (16.00), 2.367 (1.04), 2.710 (1.06), 3.162 (4.28), 3.175 (4.28), 3.285 (4.72), 4.074 (1.09), 4.087 (1.06), 4.100 (0.42), 7.357 (1.43), 7.379 (2.00), 7.404 (1.76), 7.586 (0.96), 7.605 (1.06), 7.626 (0.87), 7.724 (3.41), 7.745 (3.64), 7.869 (1.61), 7.875 (1.66), 7.887 (1.63), 7.893 (1.63), 7.921 (2.94), 8.202 (2.97), 8.298 (7.02), 8.364 (1.98), 8.370 (1.98), 8.385 (1.90), 8.391 (1.93), 8.578 (5.47), 8.977 (3.19), 8.983 (3.12), 10.500 (4.50). |
| 50 | 1H-NMR (400 MHz, DMSO-d6) delta [ppm]: −0.008 (0.84), 0.000 (16.00), 0.008 (0.50), 2.155 (1.59), 7.887 (0.51), 7.903 (0.51), 8.305 (0.62), 8.307 (0.65), 8.583 (0.53), 8.804 (0.62), 8.819 (0.56), 10.509 (0.41). |
| 51 | 1H-NMR (400 MHz, DMSO-d6) delta [ppm]: −0.149 (0.89), −0.008 (8.31), 0.008 (7.50), 0.146 (0.92), 1.148 (0.41), 2.155 (16.00), 2.366 (0.70), 2.710 (0.74), 3.285 (2.51), 7.370 (1.55), 7.391 (2.07), 7.395 (1.83), 7.417 (1.83), 7.606 (1.02), 7.612 (1.16), 7.617 (1.20), 7.623 (1.20), 7.628 (1.11), 7.633 (1.11), 7.639 (0.98), 7.645 (0.98), 7.677 (3.10), 7.854 (1.18), 7.858 (1.85), 7.865 (2.51), 7.871 (3.18), 7.875 (1.66), 7.883 (1.70), 7.889 (1.53), 7.923 (2.68), 8.199 (2.49), 8.202 (2.81), 8.301 (6.28), 8.303 (6.39), 8.474 (2.94), 8.487 (2.81), 8.583 (5.32), 10.598 (4.14). |
| 52 | 1H-NMR (400 MHz, DMSO-d6) delta [ppm]: −0.008 (2.13), 0.008 (1.92), 2.155 (12.30), 2.304 (11.70), 2.308 (16.00), 2.310 (14.60), 3.286 (1.87), 7.287 (1.96), 7.307 (2.19), 7.317 (1.31), 7.338 (1.63), 7.342 (1.46), 7.364 (1.44), 7.547 (0.74), 7.554 (0.88), 7.559 (0.88), 7.565 (0.89), 7.569 (0.83), 7.575 (0.78), 7.580 (0.71), 7.587 (0.69), 7.722 (1.27), 7.727 (1.44), 7.741 (1.12), 7.747 (1.26), 7.796 (2.48), 7.800 (2.47), 7.812 (1.42), 7.817 (1.38), 7.830 (1.36), 7.836 (1.27), 7.919 (2.12), 8.200 (2.12), 8.295 (4.67), 8.296 (5.20), 8.572 (4.14), 10.047 (3.42). |
| 53 | 1H-NMR (400 MHz, DMSO-d6) delta [ppm]: −0.008 (3.69), 0.008 (2.52), 2.155 (16.00), 2.319 (10.19), 2.324 (9.83), 3.286 (2.82), 7.288 (1.65), 7.310 (2.51), 7.328 (1.89), 7.334 (1.96), 7.350 (2.24), 7.354 (1.87), 7.375 (1.83), 7.561 (1.05), 7.567 (1.20), 7.572 (1.26), 7.578 (1.24), 7.582 (1.10), 7.588 (1.09), 7.594 (0.96), 7.600 (0.89), 7.810 (1.80), 7.816 (1.81), 7.828 (1.83), 7.834 (1.65), 7.862 (0.91), 7.869 (1.08), 7.875 (1.08), 7.882 (1.39), 7.889 (1.10), 7.896 (0.98), 7.902 (1.06), 7.915 (2.59), 7.917 (3.02), 7.951 (1.54), 7.959 (1.35), 7.970 (1.53), 7.978 (1.16), 8.198 (2.72), 8.200 (2.96), 8.295 (6.32), 8.297 (6.43), 8.573 (5.37), 10.164 (4.61). |
| 54 | 1H-NMR (400 MHz, DMSO-d6) delta [ppm]: −0.008 (1.11), 0.008 (1.03), 2.155 (13.45), 2.582 (16.00), 3.287 (1.68), 5.754 (0.98), 7.352 (1.28), 7.373 (1.75), 7.377 (1.54), 7.399 (1.51), 7.589 (0.80), 7.595 (0.97), 7.601 (1.00), 7.607 (0.99), 7.608 (0.85), 7.611 (0.92), 7.617 (0.90), 7.623 (0.80), 7.628 (0.77), 7.676 (1.42), 7.678 (1.52), 7.680 (1.53), 7.687 (1.39), 7.691 (1.61), 7.693 (1.49), 7.765 (2.56), 7.767 (3.07), 7.836 (1.37), 7.842 (1.44), 7.855 (1.45), 7.860 (1.36), 7.916 (2.17), 7.921 (2.42), 8.200 (2.27), 8.201 (2.41), 8.303 (5.54), 8.581 (4.52), 8.653 (2.38), 8.666 (2.32), 10.442 (3.76). |
| 55 | 1H-NMR (400 MHz, DMSO-d6) delta [ppm]: −0.008 (0.84), 0.008 (0.76), 2.154 (10.26), 2.524 (0.44), 3.287 (1.19), 3.935 (16.00), 5.754 (4.07), 7.313 (1.05), 7.327 (1.22), 7.334 (1.55), 7.349 (1.55), 7.353 (1.63), 7.357 (1.09), 7.374 (1.21), 7.561 (0.63), 7.567 (0.73), 7.573 (0.77), 7.579 (0.76), 7.583 (0.69), 7.588 (0.67), 7.594 (0.61), 7.600 (0.59), 7.806 (1.10), 7.812 (1.13), 7.825 (1.17), 7.831 (1.16), 7.837 (1.26), 7.842 (1.49), 7.869 (3.78), 7.874 (1.49), 7.888 (1.05), 7.890 (1.12), 7.893 (0.87), 7.896 (0.78), 7.915 (1.60), 7.921 (1.70), 8.199 (1.77), 8.203 (1.55), 8.298 (4.11), 8.299 (4.43), 8.573 (3.48), 10.123 (2.91). |
| 56 | 1H-NMR (400 MHz, DMSO-d6) delta [ppm]: −0.008 (1.45), 0.008 (1.17), 2.073 (0.43), 2.154 (16.00), 3.288 (1.82), 5.754 (1.15), 7.348 (1.62), 7.370 (2.22), 7.374 (1.94), 7.395 (1.87), 7.585 (1.05), 7.591 (1.21), 7.596 (1.28), 7.602 (1.24), 7.606 (1.16), 7.612 (1.13), 7.618 (1.01), 7.624 (0.94), 7.791 (1.57), 7.809 (2.08), 7.812 (2.82), 7.830 (4.15), 7.835 (2.12), 7.847 (1.87), 7.853 (1.77), 7.868 (2.55), 7.874 (2.35), 7.889 (1.40), 7.895 (1.38), 7.922 (2.73), 7.986 (2.14), 7.991 (2.01), 8.011 (2.06), 8.016 (1.97), 8.199 (2.74), 8.299 (6.25), 8.301 (6.72), 8.578 (5.42), 10.373 (4.54). |

TABLE 5-continued

NMR peak list (2)

| Example number | NMR-peak list |
|---|---|
| 57 | 1H-NMR (400 MHz, DMSO-d6) delta [ppm]: −0.149 (0.91), −0.008 (7.60), 0.008 (7.45), 0.146 (0.81), 1.147 (1.20), 1.234 (0.49), 2.073 (1.41), 2.366 (1.41), 2.709 (1.34), 3.286 (9.39), 7.270 (4.11), 7.289 (8.69), 7.309 (4.89), 7.490 (2.85), 7.493 (3.20), 7.509 (5.10), 7.512 (5.49), 7.524 (4.40), 7.527 (8.19), 7.532 (4.96), 7.545 (15.19), 7.548 (8.55), 7.560 (4.57), 7.564 (10.65), 7.596 (3.34), 7.599 (6.22), 7.603 (3.80), 7.612 (2.32), 7.618 (7.60), 7.624 (1.69), 7.632 (1.37), 7.636 (2.29), 7.681 (2.74), 7.685 (3.13), 7.702 (5.38), 7.718 (2.85), 7.722 (2.50), 7.989 (10.76), 7.993 (14.87), 7.998 (4.04), 8.006 (6.08), 8.010 (12.45), 8.014 (9.49), 8.093 (9.00), 8.095 (8.40), 8.390 (16.00), 8.534 (8.51), 8.540 (8.65), 8.637 (9.21), 8.642 (8.76), 10.182 (12.45). |
| 58 | 1H-NMR (400 MHz, DMSO-d6) delta [ppm]: −0.149 (0.44), −0.008 (3.96), 0.008 (3.37), 0.146 (0.45), 2.366 (0.60), 2.710 (0.52), 3.286 (3.10), 3.342 (16.00), 7.167 (0.63), 7.186 (1.23), 7.205 (0.94), 7.316 (3.02), 7.337 (1.80), 7.638 (0.68), 7.654 (1.07), 7.673 (0.62), 8.076 (2.67), 8.081 (2.80), 8.273 (2.63), 8.519 (2.76), 8.525 (2.90), 8.543 (2.43). |
| 65 | 1H-NMR (400 MHz, DMSO-d6) delta [ppm]: −0.008 (0.72), 0.008 (0.63), 2.143 (16.00), 3.200 (1.76), 3.223 (3.83), 3.246 (2.08), 3.287 (0.77), 3.510 (3.36), 3.530 (4.58), 3.533 (4.89), 3.554 (2.99), 4.275 (0.91), 4.296 (1.36), 4.319 (0.82), 5.754 (4.66), 7.236 (0.84), 7.238 (0.90), 7.240 (0.88), 7.259 (1.72), 7.261 (1.83), 7.263 (1.75), 7.281 (0.92), 7.283 (0.96), 7.285 (0.90), 7.731 (0.61), 7.746 (0.81), 7.753 (1.23), 7.768 (1.22), 7.774 (0.81), 7.789 (0.59), 7.912 (2.67), 7.917 (2.64), 8.197 (2.68), 8.312 (4.71), 8.315 (3.65), 8.548 (2.90), 8.554 (2.78), 9.703 (2.95). |
| 66 | 1H-NMR (400 MHz, DMSO-d6) delta [ppm]: −0.008 (1.35), 0.008 (1.13), 2.148 (16.00), 3.152 (1.75), 3.175 (3.79), 3.198 (2.03), 3.287 (1.41), 3.534 (3.26), 3.555 (4.81), 3.557 (5.04), 3.578 (3.01), 4.299 (1.17), 4.320 (1.82), 4.343 (1.06), 5.754 (1.02), 7.279 (1.48), 7.300 (2.06), 7.306 (1.69), 7.327 (1.86), 7.444 (0.81), 7.450 (0.98), 7.456 (1.03), 7.463 (0.96), 7.465 (0.96), 7.471 (0.85), 7.477 (0.76), 7.483 (0.69), 7.917 (2.74), 8.070 (1.16), 8.075 (1.23), 8.088 (1.19), 8.094 (1.16), 8.194 (2.63), 8.241 (5.82), 8.536 (5.09), 9.693 (2.71). |
| 67 | 1H-NMR (400 MHz, DMSO-d6) delta [ppm]: −0.149 (0.66), −0.008 (5.48), 0.008 (5.15), 0.146 (0.67), 2.157 (16.00), 3.287 (2.63), 7.293 (1.33), 7.312 (2.90), 7.332 (1.69), 7.522 (0.89), 7.538 (1.54), 7.559 (0.75), 7.680 (3.30), 7.716 (0.99), 7.720 (1.05), 7.737 (1.69), 7.752 (0.95), 7.855 (1.82), 7.868 (1.79), 7.922 (2.76), 8.203 (2.69), 8.352 (4.81), 8.468 (3.08), 8.481 (2.96), 8.591 (3.05), 10.583 (3.86). |
| 68 | 1H-NMR (400 MHz, DMSO-d6) delta [ppm]: −0.008 (3.44), 0.008 (3.01), 2.073 (2.73), 2.157 (16.00), 3.287 (1.60), 7.284 (1.33), 7.303 (2.92), 7.323 (1.66), 7.503 (0.85), 7.507 (0.92), 7.525 (1.51), 7.541 (0.79), 7.545 (0.73), 7.706 (0.99), 7.710 (1.02), 7.727 (1.71), 7.743 (0.95), 7.747 (0.84), 7.887 (5.43), 7.891 (3.39), 7.898 (3.54), 7.902 (5.59), 7.918 (2.77), 8.203 (2.70), 8.352 (4.66), 8.588 (3.04), 8.799 (6.20), 8.804 (3.61), 8.810 (3.55), 8.815 (5.91), 10.495 (3.83). |
| 69 | 1H-NMR (400 MHz, DMSO-d6) delta [ppm]: −0.149 (0.94), −0.011 (4.87), −0.008 (10.96), 0.008 (6.75), 0.146 (0.87), 1.147 (0.74), 2.073 (0.87), 2.156 (16.00), 2.327 (0.59), 2.366 (0.76), 2.670 (0.59), 2.710 (0.76), 3.286 (7.64), 7.293 (1.40), 7.313 (2.90), 7.333 (1.58), 7.564 (0.97), 7.582 (1.58), 7.598 (0.82), 7.706 (1.04), 7.710 (1.12), 7.727 (1.76), 7.743 (0.99), 7.747 (0.89), 7.919 (2.85), 8.204 (2.83), 8.239 (2.80), 8.241 (2.80), 8.259 (3.06), 8.261 (3.08), 8.351 (4.69), 8.532 (2.27), 8.537 (2.19), 8.552 (1.94), 8.558 (1.96), 8.590 (3.13), 9.243 (2.45), 9.245 (2.62), 9.248 (2.55), 10.661 (3.92). |
| 70 | 1H-NMR (400 MHz, DMSO-d6) delta [ppm]: −0.008 (3.51), 0.008 (2.14), 2.073 (1.82), 2.157 (16.00), 3.287 (2.39), 7.281 (1.41), 7.300 (2.95), 7.320 (1.64), 7.525 (0.97), 7.529 (1.06), 7.547 (1.62), 7.563 (0.85), 7.567 (0.77), 7.696 (1.14), 7.700 (1.19), 7.718 (4.78), 7.720 (4.49), 7.733 (1.26), 7.739 (3.77), 7.740 (3.59), 7.918 (2.81), 8.203 (2.80), 8.350 (4.88), 8.363 (2.65), 8.369 (2.53), 8.384 (2.34), 8.390 (2.32), 8.587 (3.17), 8.974 (2.98), 8.976 (3.06), 8.980 (2.99), 8.982 (2.80), 10.488 (4.26). |
| 71 | 1H-NMR (400 MHz, DMSO-d6) delta [ppm]: −0.008 (1.05), 0.008 (0.86), 2.157 (9.82), 3.288 (0.86), 3.936 (16.00), 7.269 (0.81), 7.289 (1.79), 7.309 (1.07), 7.363 (1.24), 7.384 (1.49), 7.391 (1.26), 7.412 (1.40), 7.486 (1.06), 7.612 (0.69), 7.618 (0.76), 7.623 (0.77), 7.629 (0.79), 7.639 (0.74), 7.644 (0.66), 7.650 (0.67), 7.705 (1.06), 7.762 (1.20), 7.767 (1.13), 7.783 (1.21), 7.788 (1.10), 7.919 (1.68), 8.203 (1.66), 8.350 (3.04), 8.583 (1.90), 10.199 (2.48). |
| 72 | 1H-NMR (400 MHz, DMSO-d6) delta [ppm]: 2.156 (10.40), 3.934 (16.00), 7.256 (0.88), 7.276 (1.94), 7.296 (1.13), 7.310 (1.07), 7.332 (1.89), 7.354 (0.95), 7.479 (1.13), 7.691 (1.16), 7.838 (1.13), 7.844 (1.46), 7.869 (2.78), 7.875 (1.45), 7.887 (1.17), 7.894 (0.81), 7.920 (1.87), 8.202 (1.85), 8.345 (3.13), 8.577 (2.08), 10.111 (2.84). |
| 73 | 1H-NMR (400 MHz, DMSO-d6) delta [ppm]: −0.008 (0.86), 0.008 (0.82), 2.157 (11.52), 3.288 (0.63), 3.312 (16.00), 3.757 (0.84), 7.163 (0.98), 7.165 (1.10), 7.169 (1.09), 7.171 (1.10), 7.183 (1.14), 7.186 (1.21), 7.190 (1.26), 7.192 (1.14), 7.263 (0.99), 7.282 (2.15), 7.302 (1.21), 7.436 (1.51), 7.456 (2.66), 7.469 (0.78), 7.476 (2.04), 7.488 (1.22), 7.492 (1.22), 7.507 (0.64), 7.511 (0.59), 7.539 (1.61), 7.543 (2.17), 7.550 (1.76), 7.573 (1.38), 7.576 (1.79), 7.579 (1.14), 7.592 (1.06), 7.595 (1.30), 7.599 (0.83), 7.678 (0.70), 7.682 (0.74), 7.699 (1.23), 7.715 (0.67), 7.719 (0.60), 7.918 (2.04), 8.202 (1.99), 8.349 (3.55), 8.582 (2.31), 10.159 (2.92). |
| 74 | 1H-NMR (400 MHz, DMSO-d6) delta [ppm]: −0.149 (0.62), −0.008 (5.17), 0.008 (4.31), 0.146 (0.59), 2.073 (0.92), 2.155 (10.58), 3.286 (3.94), 4.024 (16.00), 7.286 (0.87), 7.306 (1.94), 7.326 (1.06), 7.509 (1.04), 7.660 (1.40), 7.664 (1.38), 7.680 (1.57), 7.684 (1.69), 7.725 (1.18), 7.743 (0.73), 7.764 (2.75), 7.768 (2.68), 7.918 (4.94), 7.938 (2.67), 8.137 (1.49), 8.203 (1.82), 8.352 (3.20), 8.590 (2.08), 10.437 (2.59). |
| 75 | 1H-NMR (400 MHz, DMSO-d6) delta [ppm]: −0.149 (0.85), −0.011 (7.25), −0.008 (13.48), 0.008 (6.23), 0.146 (0.85), 1.147 (0.90), 2.155 (16.00), 2.332 (0.67), 2.366 (0.72), 2.669 (0.90), 2.709 (0.85), 3.286 (8.08), 7.254 (1.47), 7.273 (3.06), 7.293 (1.65), 7.474 (1.21), 7.488 (1.72), 7.628 (2.34), 7.631 (2.34), 7.640 (4.60), 7.644 (4.30), 7.658 (4.63), 7.666 (5.40), 7.671 (2.42), 7.679 (3.27), 7.699 (0.95), 7.916 (2.83), 8.204 (2.70), 8.343 (4.91), 8.375 (3.42), 8.378 (3.68), 8.382 (3.34), 8.386 (3.04), 8.577 (3.14), 10.003 (3.96). |
| 76 | 1H-NMR (400 MHz, DMSO-d6) delta [ppm]: −0.008 (1.44), 0.008 (1.34), 2.073 (0.79), 2.139 (2.57), 2.156 (16.00), 3.289 (1.63), 7.167 (0.44), 7.227 (2.40), 7.237 (2.63), 7.240 (2.68), 7.249 (2.54), 7.260 (1.38), 7.279 (2.90), 7.300 (1.68), 7.418 (0.45), 7.437 (0.75), 7.458 (1.29), 7.473 (1.77), 7.492 (0.91), 7.508 (0.48), 7.678 (0.98), 7.682 (1.04), 7.698 (1.78), 7.715 (0.92), 7.872 (2.63), 7.875 (2.89), 7.884 (2.63), 7.887 (2.71), 7.918 (2.87), 8.013 (0.56), 8.025 (3.02), 8.028 (3.11), 8.034 (2.73), 8.037 (2.57), 8.202 (2.81), 8.349 (4.99), 8.585 (3.10), 8.611 (0.51), 9.539 (1.13), 10.211 (4.07). |
| 77 | 1H-NMR (400 MHz, DMSO-d6) delta [ppm]: −0.008 (1.12), 0.008 (0.94), 2.157 (16.00), 3.288 (1.39), 7.258 (1.36), 7.278 (2.80), 7.297 (1.53), 7.645 (0.84), 7.649 (1.11), 7.667 (1.89), 7.683 (1.11), 7.691 (1.88), 7.710 (0.96), 7.923 (2.72), 8.205 (2.61), 8.347 (4.73), 8.590 (3.14), 8.639 (5.70), 8.642 (5.86), 8.852 (6.10), 8.855 (5.94), 9.843 (3.13). |
| 2-01 | 1H-NMR (400 MHz, DMSO-d6) delta [ppm]: −0.008 (4.69), 0.008 (2.78), 2.154 (16.00), 3.286 (3.27), 7.331 (1.66), 7.353 (2.20), 7.357 (1.83), 7.380 (1.79), 7.656 (1.05), 7.663 (1.31), 7.667 (1.36), 7.681 (4.17), 7.696 (0.89), 7.842 (1.44), 7.847 (2.00), 7.851 (1.46), 7.855 (1.54), 7.859 (2.00), 7.864 (1.28), 7.916 (2.87), 8.096 (1.70), 8.103 (1.70), 8.114 (1.68), 8.120 (1.56), 8.199 (3.06), 8.214 (4.72), 8.469 (3.14), 8.482 (2.91), 8.540 (3.31), 10.667 (3.66). |

TABLE 5-continued

NMR peak list (2)

| Example number | NMR-peak list |
|---|---|
| 2-02 | 1H-NMR (400 MHz, DMSO-d6) delta [ppm]: −0.149 (0.69), −0.008 (9.62), 0.146 (0.62), 1.148 (0.89), 2.154 (16.00), 2.327 (0.67), 2.366 (0.93), 2.670 (0.69), 2.710 (0.96), 3.287 (8.93), 7.318 (1.51), 7.344 (2.13), 7.367 (1.67), 7.672 (1.38), 7.876 (5.24), 7.880 (4.38), 7.887 (3.82), 7.891 (5.62), 7.919 (3.31), 8.115 (1.78), 8.127 (1.78), 8.132 (1.76), 8.201 (3.44), 8.217 (4.82), 8.539 (3.71), 8.801 (5.58), 8.805 (4.51), 8.812 (3.60), 8.816 (5.58), 10.603 (3.69). |
| 2-03 | 1H-NMR (400 MHz, DMSO-d6) delta [ppm]: −0.008 (2.66), 0.008 (1.16), 2.073 (2.82), 2.154 (16.00), 3.287 (2.26), 7.333 (1.67), 7.355 (2.26), 7.359 (1.91), 7.381 (1.76), 7.657 (0.99), 7.664 (1.19), 7.668 (1.18), 7.675 (1.14), 7.679 (1.04), 7.686 (1.06), 7.691 (0.91), 7.697 (0.77), 7.917 (2.98), 8.096 (1.70), 8.103 (1.74), 8.114 (1.67), 8.120 (1.48), 8.199 (3.26), 8.213 (4.74), 8.250 (2.85), 8.252 (2.82), 8.270 (3.18), 8.272 (3.14), 8.528 (2.76), 8.533 (2.88), 8.542 (3.75), 8.548 (4.23), 8.553 (2.16), 9.242 (2.78), 9.244 (2.97), 9.248 (2.76), 9.250 (2.47), 10.753 (4.03). |
| 2-04 | 1H-NMR (400 MHz, DMSO-d6) delta [ppm]: −0.008 (8.45), 0.008 (3.72), 1.147 (0.65), 2.153 (16.00), 2.366 (0.94), 2.710 (0.82), 3.285 (7.20), 7.317 (1.63), 7.339 (2.23), 7.343 (1.96), 7.366 (1.76), 7.643 (1.00), 7.650 (1.20), 7.661 (1.16), 7.665 (1.09), 7.672 (1.07), 7.683 (0.87), 7.727 (3.25), 7.748 (3.39), 7.916 (3.08), 8.084 (1.76), 8.091 (1.83), 8.102 (1.72), 8.108 (1.60), 8.198 (3.30), 8.211 (4.64), 8.359 (2.38), 8.365 (2.30), 8.380 (2.14), 8.386 (2.09), 8.535 (3.43), 8.970 (3.03), 8.976 (2.74), 10.588 (4.10). |
| 2-05 | 1H-NMR (400 MHz, DMSO-d6) delta [ppm]: −0.008 (2.38), 0.008 (2.30), 2.153 (9.91), 3.286 (2.64), 3.942 (16.00), 7.301 (1.02), 7.323 (1.32), 7.327 (1.23), 7.350 (1.15), 7.372 (1.20), 7.393 (1.47), 7.400 (1.25), 7.421 (1.44), 7.599 (0.68), 7.605 (0.77), 7.610 (0.76), 7.616 (0.78), 7.626 (0.70), 7.637 (1.18), 7.724 (1.21), 7.729 (1.15), 7.745 (1.25), 7.750 (1.15), 7.916 (1.70), 8.072 (1.08), 8.078 (1.10), 8.089 (1.11), 8.096 (1.04), 8.198 (1.67), 8.215 (2.87), 8.530 (2.00), 10.328 (2.47). |
| 2-06 | 1H-NMR (400 MHz, DMSO-d6) delta [ppm]: −0.008 (1.18), 0.008 (1.18), 2.153 (10.18), 3.287 (1.47), 3.935 (16.00), 7.284 (1.06), 7.307 (1.43), 7.311 (1.40), 7.315 (1.20), 7.333 (1.84), 7.336 (2.06), 7.358 (0.83), 7.674 (0.71), 7.843 (0.98), 7.849 (1.77), 7.856 (1.57), 7.877 (3.62), 7.916 (1.79), 8.085 (1.14), 8.092 (1.13), 8.103 (1.16), 8.109 (1.07), 8.197 (1.83), 8.207 (3.22), 8.521 (2.08), 10.240 (2.63). |
| 2-07 | 1H-NMR (400 MHz, DMSO-d6) delta [ppm]: −0.008 (1.92), 0.008 (1.68), 2.154 (10.25), 3.286 (2.00), 3.846 (16.00), 3.935 (1.60), 5.754 (1.67), 7.160 (0.74), 7.162 (0.81), 7.166 (0.83), 7.168 (0.81), 7.180 (0.87), 7.182 (0.91), 7.187 (0.98), 7.189 (0.87), 7.289 (0.96), 7.311 (1.34), 7.315 (1.24), 7.337 (1.22), 7.444 (1.11), 7.463 (2.10), 7.483 (1.34), 7.509 (1.23), 7.513 (1.72), 7.519 (1.41), 7.551 (1.11), 7.554 (1.45), 7.558 (0.97), 7.570 (0.77), 7.573 (1.00), 7.918 (1.84), 8.107 (1.06), 8.114 (1.01), 8.125 (1.02), 8.131 (0.98), 8.198 (1.88), 8.208 (3.11), 8.523 (2.05), 10.308 (2.27). |
| 2-08 | 1H-NMR (400 MHz, DMSO-d6) delta [ppm]: −0.008 (0.98), 0.008 (0.83), 2.074 (3.55), 2.154 (10.48), 3.288 (0.76), 4.030 (16.00), 7.322 (1.08), 7.345 (1.40), 7.349 (1.22), 7.371 (1.19), 7.651 (1.77), 7.655 (2.02), 7.671 (2.11), 7.675 (2.01), 7.729 (2.85), 7.732 (2.62), 7.918 (1.89), 7.928 (3.16), 7.949 (2.58), 8.080 (1.06), 8.086 (1.08), 8.097 (1.09), 8.104 (1.00), 8.199 (1.81), 8.218 (3.07), 8.538 (2.11), 10.547 (2.66). |
| 2-09 | 1H-NMR (400 MHz, DMSO-d6) delta [ppm]: −0.008 (1.90), 0.008 (1.80), 2.153 (16.00), 3.287 (1.54), 7.282 (1.62), 7.305 (2.12), 7.309 (1.89), 7.331 (1.80), 7.629 (1.06), 7.635 (2.42), 7.638 (2.68), 7.647 (4.69), 7.650 (4.53), 7.658 (1.33), 7.664 (4.12), 7.671 (3.85), 7.676 (1.58), 7.684 (1.56), 7.916 (2.83), 8.066 (1.75), 8.073 (1.75), 8.084 (1.80), 8.091 (1.67), 8.198 (2.90), 8.208 (4.90), 8.350 (2.59), 8.354 (2.85), 8.358 (2.73), 8.361 (2.53), 8.521 (3.32), 10.150 (3.85). |
| 2-10 | 1H-NMR (400 MHz, DMSO-d6) delta [ppm]: −0.008 (2.18), 0.008 (2.07), 2.073 (0.59), 2.156 (16.00), 3.287 (2.43), 7.289 (1.68), 7.311 (2.15), 7.315 (1.93), 7.337 (1.88), 7.528 (1.13), 7.532 (1.86), 7.536 (0.76), 7.549 (4.90), 7.554 (2.48), 7.565 (1.70), 7.568 (3.88), 7.589 (1.19), 7.593 (2.26), 7.596 (1.34), 7.605 (0.74), 7.611 (2.48), 7.629 (0.66), 7.669 (0.94), 7.675 (1.10), 7.680 (1.12), 7.686 (1.05), 7.691 (1.02), 7.697 (1.08), 7.702 (0.97), 7.709 (0.90), 7.919 (2.79), 7.968 (3.63), 7.972 (4.98), 7.978 (1.28), 7.985 (2.10), 7.989 (4.23), 7.993 (3.27), 8.120 (1.74), 8.127 (1.77), 8.138 (1.81), 8.144 (1.67), 8.199 (2.94), 8.207 (5.13), 8.522 (3.17), 10.343 (3.93). |
| 2-11 | 1H-NMR (400 MHz, DMSO-d6) delta [ppm]: −0.008 (0.69), 2.151 (16.00), 3.288 (2.63), 7.304 (1.63), 7.326 (2.13), 7.330 (1.90), 7.353 (1.85), 7.628 (0.94), 7.635 (1.13), 7.639 (1.13), 7.646 (1.08), 7.650 (1.04), 7.657 (1.05), 7.662 (0.97), 7.669 (0.89), 7.918 (2.84), 7.991 (6.91), 8.046 (1.76), 8.052 (1.76), 8.063 (1.82), 8.070 (1.67), 8.199 (2.87), 8.214 (4.57), 8.529 (3.16), 8.677 (5.04), 10.530 (3.93). |
| 2-12 | 1H-NMR (400 MHz, DMSO-d6) delta [ppm]: −0.008 (2.14), 0.008 (2.06), 2.152 (16.00), 3.287 (2.80), 7.274 (1.71), 7.296 (2.11), 7.300 (1.95), 7.323 (1.87), 7.752 (0.92), 7.759 (1.08), 7.763 (1.12), 7.770 (1.08), 7.775 (1.05), 7.781 (1.06), 7.786 (1.01), 7.792 (0.92), 7.915 (2.72), 8.158 (1.76), 8.164 (1.80), 8.175 (1.85), 8.182 (1.76), 8.198 (2.76), 8.212 (4.89), 8.506 (3.13), 8.643 (5.46), 8.646 (5.57), 8.815 (5.74), 8.818 (5.67), 10.239 (3.86). |
| 2-13 | 1H-NMR (400 MHz, DMSO-d6) delta [ppm]: −0.149 (0.93), −0.008 (12.41), 0.008 (6.58), 0.146 (0.93), 1.147 (1.54), 2.328 (1.07), 2.366 (2.29), 2.669 (1.07), 2.710 (2.19), 3.287 (16.00), 7.292 (3.03), 7.311 (6.34), 7.331 (3.64), 7.514 (2.33), 7.531 (3.78), 7.548 (1.82), 7.717 (2.43), 7.735 (4.10), 7.750 (2.01), 7.886 (11.15), 7.890 (7.74), 7.897 (7.65), 7.902 (11.10), 8.091 (7.04), 8.396 (11.38), 8.538 (7.23), 8.646 (7.14), 8.800 (11.76), 8.804 (7.79), 8.811 (7.42), 8.815 (11.20), 10.500 (8.72). |
| 2-14 | 1H-NMR (400 MHz, DMSO-d6) delta [ppm]: −0.149 (1.25), −0.008 (10.18), 0.008 (9.00), 0.146 (1.25), 1.147 (1.87), 2.327 (1.45), 2.366 (2.63), 2.670 (1.52), 2.710 (2.70), 3.286 (12.95), 7.264 (4.16), 7.284 (8.66), 7.304 (4.71), 7.655 (3.46), 7.673 (8.52), 7.693 (8.17), 7.709 (2.98), 8.099 (9.07), 8.388 (15.93), 8.545 (9.07), 8.638 (13.37), 8.641 (16.00), 8.651 (9.63), 8.851 (13.23), 8.853 (14.20), 9.857 (10.18). |

Biological Examples

*Ctenocephalides felis*—In Vitro Contact Tests with Adult Cat Fleas

For the coating of the test tubes, 9 mg of active ingredient are first dissolved in 1 ml of acetone p.a. and then diluted to the desired concentration with acetone p.a. 250 µl of the solution are distributed homogeneously on the inner walls and the base of a 25 ml glass tube by turning and rocking on an orbital shaker (rocking rotation at 30 rpm for 2 h). With 900 ppm of active ingredient solution and internal surface area 44.7 cm$^2$, given homogeneous distribution, an area-based dose of 5 µg/cm$^2$ is achieved.

After the solvent has evaporated off, the tubes are populated with 5-10 adult cat fleas (*Ctenocephalides felis*), sealed with a perforated plastic lid and incubated in a horizontal position at room temperature and ambient humidity. After 48 h, efficacy is determined. To this end, the tubes are stood upright and the fleas are knocked to the base of the tube. Fleas which remain motionless at the base or move in an uncoordinated manner are considered to be dead or moribund.

A substance shows good efficacy against *Ctenocephalides felis* if at least 80% efficacy was achieved in this test at an application rate of 5 µg/cm². 100% efficacy means that all the fleas were dead or moribund. 0% efficacy means that no fleas were harmed.

In this test, for example, the following compounds from the preparation examples show an efficacy of 100% at an application rate of 5 µg/cm² (500 g/ha): 2, 6, 7, 12, 15, 17, 19, 20, 25, 30, 32, 33, 43, 45, 46, 50, 51, 54, 57, 67, 68, 69, 2-14.

In this test, for example, the following compounds from the preparation examples show an efficacy of 80% at an application rate of 5 µg/cm² (500 g/ha): 58, 2-13.

*Rhipicephalus sanguineus*—In Vitro Contact Tests with Adult Brown Dog Ticks

For the coating of the test tubes, 9 mg of active ingredient are first dissolved in 1 ml of acetone p.a. and then diluted to the desired concentration with acetone p.a. 250 µl of the solution are distributed homogeneously on the inner walls and the base of a 25 ml glass tube by turning and rocking on an orbital shaker (rocking rotation at 30 rpm for 2 h). With 900 ppm of active ingredient solution and internal surface area 44.7 cm², given homogeneous distribution, an area-based dose of 5 µg/cm² is achieved.

After the solvent has evaporated off, the tubes are populated with 5-10 adult dog ticks (*Rhipicephalus sanguineus*), sealed with a perforated plastic lid and incubated in a horizontal position in the dark at room temperature and ambient humidity. After 48 h, efficacy is determined. To this end, the ticks are knocked to the base of the tube and incubated on a hotplate at 45-50° C. for not more than 5 min. Ticks which remain motionless on the base or move in such an uncoordinated manner that they are unable to deliberately avoid the heat by climbing upwards are considered to be dead or moribund.

A substance shows good activity against *Rhipicephalus sanguineus* if, in this test, an efficacy of at least 80% was achieved at an application rate of 5 µg/cm². An efficacy of 100% means that all the ticks were dead or moribund. 0% efficacy means that none of the ticks were harmed.

In this test, for example, the following compounds from the preparation examples show an efficacy of 100% at an application rate of 5 µg/cm² (500 g/ha): 2, 4, 24, 66, 57, 58.

In this test, for example, the following compounds from the preparation examples show an efficacy of 80% at an application rate of 5 µg/cm² (500 g/ha): 5, 7, 11, 12, 16, 33, 43, 50, 2-13, 2-14.

In this test, for example, the following compounds from the preparation examples show an efficacy of 100% at an application rate of 1 µg/cm² (100 g/ha): 6, 23, 77, 2-12.

In this test, for example, the following compounds from the preparation examples show an efficacy of 80% at an application rate of 1 µg/cm² (100 g/ha): 67.

*Boophilus microplus*—Dip Test

Test animals: cattle ticks (*Boophilus microplus*) Parkhurst strain, SP-resistant Solvent: dimethyl sulfoxide 10 mg of active ingredient are dissolved in 0.5 ml of dimethyl sulfoxide. To produce a suitable formulation, the active ingredient solution is diluted with water to the concentration desired in each case.

This active ingredient formulation is pipetted into tubes. 8-10 engorged adult female cattle ticks (*Boophilus microplus*) are transferred into a further tube with holes. The tube is immersed into the active ingredient formulation, and all the ticks are completely wetted. After the liquid has run out, the ticks are transferred on filter disks into plastic dishes and stored in a climate-controlled room.

Efficacy is assessed after 7 days by laying of fertile eggs. Eggs which are not visibly fertile are stored in a climate-controlled cabinet until the larvae hatch after about 42 days. An efficacy of 100% means that none of the ticks has laid any fertile eggs; 0% means that all the eggs are fertile.

In this test, for example, the following compounds from the preparation examples show an efficacy of 100% at an application rate of 100 ppm: 2, 2-13.

In this test, for example, the following compounds from the preparation examples show an efficacy of 90% at an application rate of 100 ppm: 31.

*Boophilus microplus*—Injection Test

Solvent: dimethyl sulfoxide

To produce a suitable active ingredient formulation, 10 mg of active ingredient are mixed with 0.5 ml of solvent and the concentrate is diluted to the desired concentration with solvent.

1 µl of the active ingredient solution is injected into the abdomen of 5 engorged adult female cattle ticks (*Boophilus microplus*). The animals are transferred into dishes and kept in a climate-controlled room.

Efficacy is assessed after 7 days by laying of fertile eggs. Eggs which are not visibly fertile are stored in a climate-controlled cabinet until the larvae hatch after about 42 days. An efficacy of 100% means that none of the ticks has laid any fertile eggs; 0% means that all the eggs are fertile.

In this test, for example, the following compounds from the preparation examples show an efficacy of 100% at an application rate of 20 µg/animal: 2, 3, 4, 5, 6, 7, 8, 9, 10, 11, 12, 13, 15, 16, 19, 20, 21, 22, 23, 24, 25, 26, 27, 29, 30, 31, 32, 33, 36, 37, 38, 39, 40, 41, 42, 43, 44, 45, 46, 47, 48, 50, 51, 52, 53, 54, 55, 56, 57, 58, 66, 67, 68, 69, 70, 71, 72, 73, 74, 75, 76, 77, 2-1, 2-2, 2-3, 2-4, 2-5, 2-8, 2-9, 2-10, 2-11, 2-12, 2-13, 2-14.

In this test, for example, the following compounds from the preparation examples show an efficacy of 80% at an application rate of 20 µg/animal: 14, 65, 2-6.

In this test, for example, the following compounds from the preparation examples show an efficacy of 100% at an application rate of 4 µg/animal: 17.

*Ctenocephalides felis*—Oral Test

Solvent: dimethyl sulfoxide

To produce a suitable active ingredient formulation, 10 mg of active ingredient are mixed with 0.5 ml of dimethyl sulphoxide. Dilution with citrated cattle blood gives the desired concentration.

About 20 unfed adult cat fleas (*Ctenocephalides felis*) are placed into a chamber which is closed at the top and bottom with gauze. A metal cylinder whose bottom end is closed with parafilm is placed onto the chamber. The cylinder contains the blood/active ingredient formulation, which can be imbibed by the fleas through the parafilm membrane.

Nach 2 Tagen wird die Abtötung in % bestimmt. 100% means that all of the fleas have been killed; 0% means that none of the fleas have been killed.

In this test, for example, the following compounds from the preparation examples show an efficacy of 100% at an application rate of 100 ppm: 2, 4, 6, 9, 11, 12, 13, 15, 16, 19, 20, 21, 22, 23, 24, 25, 26, 27, 30, 31, 32, 33, 36, 37, 38, 39, 40, 41, 42, 43, 44, 45, 46, 48, 49, 50, 51, 53, 54, 55, 56, 57, 58, 65, 66, 67, 68, 69, 70, 71, 73, 76, 77, 2-3, 2-11, 2-13, 2-14.

In this test, for example, the following compounds from the preparation examples show an efficacy of 95% at an application rate of 100 ppm: 72, 75, 2-1, 2-2, 2-4, 2-9, 2-12.

In this test, for example, the following compounds from the preparation examples show an efficacy of 90% at an application rate of 100 ppm: 3, 5.

In this test, for example, the following compounds from the preparation examples show an efficacy of 80% at an application rate of 100 ppm: 29, 47.

In this test, for example, the following compounds from the preparation examples show an efficacy of 100% at an application rate of 20 ppm: 17.

*Lucilia cuprina* Test

Solvent: dimethyl sulfoxide

To produce a suitable preparation of active compound, 10 mg of active compound are mixed with 0.5 ml of dimethyl sulfoxide, and the concentrate is diluted with water to the desired concentration.

About 20 L1 larvae of the Australian sheep blowfly (*Lucilia cuprina*) are transferred into a test vessel containing minced horsemeat and the active compound formulation of the desired concentration.

After 2 days, the kill in % is determined. 100% means that all the larvae have been killed; 0% means that no larvae have been killed.

In this test, for example, the following compounds from the preparation examples show an efficacy of 100% at an application rate of 100 ppm: 2, 4, 5, 6, 9, 11, 15, 19, 22, 23, 24, 25, 26, 30, 31, 32, 33, 36, 37, 38, 39, 40, 41, 42, 43, 44, 45, 46, 48, 49, 50, 51, 54, 56, 57, 58, 65, 66, 67, 68, 69, 70, 72, 73, 74, 76, 77, 2-3, 2-9, 2-11, 2-13.

In this test, for example, the following compounds from the preparation examples show an efficacy of 98% at an application rate of 100 ppm: 2-1, 2-2.

In this test, for example, the following compounds from the preparation examples show an efficacy of 95% at an application rate of 100 ppm: 16.

In this test, for example, the following compounds from the preparation examples show an efficacy of 90% at an application rate of 100 ppm: 12, 13, 27, 2-4, 2-8, 2-12, 2-14.

In this test, for example, the following compounds from the preparation examples show an efficacy of 80% at an application rate of 100 ppm: 7, 55, 75.

In this test, for example, the following compounds from the preparation examples show an efficacy of 100% at an application rate of 20 ppm: 17.

*Musca domestica* Test

Solvent: dimethyl sulfoxide

To produce a suitable preparation of active compound, 10 mg of active compound are mixed with 0.5 ml of dimethyl sulfoxide, and the concentrate is diluted with water to the desired concentration.

Vessels containing a sponge treated with sugar solution and the active ingredient formulation of the desired concentration are populated with 10 adult houseflies (*Musca domestica*)).

After 2 days, the kill in % is determined. 100% means that all of the flies have been killed; 0% means that none of the flies have been killed.

In this test, for example, the following compounds from the preparation examples show an efficacy of 100% at an application rate of 100 ppm: 2, 6, 9, 11, 12, 15, 16, 19, 22, 24, 25, 30, 31, 39, 40, 41, 42, 43, 44, 45, 46, 48, 49, 50, 51, 52, 53, 54, 57, 58, 65, 66, 67, 68, 70, 77, 2-1, 2-3, 2-13. In this test, for example, the following compounds from the preparation examples show an efficacy of 90% at an application rate of 100 ppm: 20, 32, 33, 2-2, 2-14.

In this test, for example, the following compounds from the preparation examples show an efficacy of 80% at an application rate of 100 ppm: 5, 13, 23.

In this test, for example, the following compounds from the preparation examples show an efficacy of 100% at an application rate of 20 ppm: 17.

*Meloidogyne incognita*—Test

Solvent: 125.0 parts by weight of acetone

To produce a suitable active ingredient formulation, 1 part by weight of active ingredient is mixed with the stated amount of solvent and the concentrate is diluted to the desired concentration with water.

Vessels are filled with sand, active ingredient solution, an egg/larvae suspension of the southern root-knot nematode (*Meloidogyne incognita*) and lettuce seeds. The lettuce seeds germinate and the plants develop. The galls develop on the roots.

After 14 days, the nematicidal efficacy in % is determined by the formation of galls. 100% means that no galls were found; 0% means that the number of galls on the treated plants corresponds to the untreated control.

In this test, for example, the following compound from the preparation examples shows an efficacy of 90% at an application rate of 20 ppm: 2-3, 2-4.

*Phaedon cochleariae*—Spray Test

Solvent: 78.0 parts by weight of acetone 1.5 parts by weight of dimethylformamide Emulsifier: alkylaryl polyglycol ether To produce a suitable active ingredient formulation, 1 part by weight of active ingredient is dissolved with the specified parts by weight of solvent and made up to the desired concentration with water containing an emulsifier concentration of 1000 ppm. To produce further test concentrations, the formulation is diluted with emulsifier-containing water.

Discs of Chinese cabbage leaves (*Brassica pekinensis*) are sprayed with an active ingredient formulation of the desired concentration and, after drying, populated with larvae of the mustard beetle (*Phaedon cochleariae*).

After 7 days, the efficacy in % is determined. 100% means that all the beetle larvae have been killed; 0% means that no beetle larvae have been killed.

In this test, for example, the following compounds from the preparation examples show an efficacy of 100% at an application rate of 500 g/ha: 2, 3, 4, 5 In this test, for example, the following compounds from the preparation examples show an efficacy of 100% at an application rate of 100 g/ha: 6, 7, 9, 11, 12, 15, 16, 17, 19, 20, 22, 23, 24, 25, 26, 28, 30, 31, 32, 33, 35, 36, 37, 38, 39, 40, 41, 42, 43, 44, 45, 46, 48, 49, 50, 51, 54, 55, 57, 58, 65, 66, 67, 68, 69, 70, 71, 72, 73, 74, 76, 77, 2-1, 2-2, 2-3, 2-4, 2-11, 2-12, 2-13, 2-14.

In this test, for example, the following compounds from the preparation examples show an efficacy of 83% at an application rate of 100 g/ha: 18, 2-8.

*Spodoptera frugiperda*—Spray Test

Solvent: 78.0 parts by weight of acetone 1.5 parts by weight of dimethylformamide Emulsifier: alkylaryl polyglycol ether To produce a suitable active ingredient formulation, 1 part by weight of active ingredient is dissolved with the specified parts by weight of solvent and made up to the desired concentration with water containing an emulsifier concentration of 1000 ppm. To produce further test concentrations, the formulation is diluted with emulsifier-containing water.

Leaf discs of maize (*Zea mays*) are sprayed with an active compound formulation of the desired concentration and, after drying, populated with caterpillars of the armyworm (*Spodoptera frugiperda*).

After 7 days, the efficacy in % is determined. 100% means that all the caterpillars have been killed; 0% means that no caterpillar has been killed.

In this test, for example, the following compounds from the preparation examples show an efficacy of 100% at an application rate of 500 g/ha: 2, 4, 5

In this test, for example, the following compounds from the preparation examples show an efficacy of 100% at an application rate of 100 g/ha: 2, 4, 5, 6, 9, 11, 12, 15, 16, 17, 18, 19, 20, 21, 22, 23, 24, 25, 26, 30, 31, 32, 33, 35, 36, 37, 39, 40, 42, 43, 44, 45, 46, 48, 49, 50, 51, 54, 65, 66, 57, 58, 67, 68, 69, 70, 71, 73, 74, 76, 77, 2-1, 2-2, 2-3, 2-4, 2-11, 2-12, 2-13, 2-14.

In this test, for example, the following compounds from the preparation examples show an efficacy of 83% at an application rate of 100 g/ha: 7, 13, 41.

*Tetranychus urticae*—Spray Test, OP-Resistant
Solvent: 78.0 parts by weight of acetone
1.5 parts by weight of dimethylformamide
Emulsifier: alkylaryl polyglycol ether To produce a suitable active ingredient formulation, 1 part by weight of active ingredient is dissolved with the specified parts by weight of solvent and made up to the desired concentration with water containing an emulsifier concentration of 1000 ppm. To produce further test concentrations, the formulation is diluted with emulsifier-containing water.

Discs of bean leaves (*Phaseolus vulgaris*) infested with all stages of the greenhouse red spider mite (*Tetranychus urticae*) are sprayed with an active ingredient formulation of the desired concentration.

After 6 days, the efficacy in % is determined. 100% means that all the spider mites have been killed; 0% means that no spider mites have been killed.

In this test, for example, the following compounds from the preparation examples show an efficacy of 100% at an application rate of 500 g/ha: 2, 5.

In this test, for example, the following compounds from the preparation examples show an efficacy of 90% at an application rate of 500 g/ha: 3, 4.

In this test, for example, the following compounds from the preparation examples shows an efficacy of 100% at an application rate of 100 g/ha: 2, 4, 5, 6, 7, 9, 12, 17, 19, 20, 22, 24, 25, 31, 39, 40, 42, 50, 54, 65, 66, 67, 68.

In this test, for example, the following compounds from the preparation examples shows an efficacy of 90% at an application rate of 100 g/ha: 11, 33, 51, 2-1, 2-2, 2-3, 2-13.

The invention claimed is:
1. A compound of formula (I)

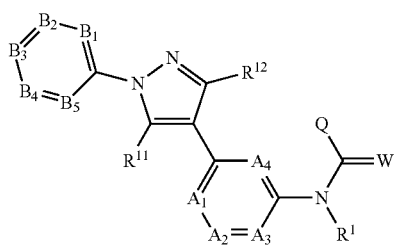

where
$R^1$ is hydrogen, optionally substituted $C_1$-$C_6$-alkyl, $C_3$-$C_6$-alkenyl, $C_3$-$C_6$-alkynyl, $C_3$-$C_7$-cycloalkyl, $C_1$-$C_6$-alkylcarbonyl, $C_1$-$C_6$-alkoxycarbonyl, aryl($C_1$-$C_3$)-alkyl, heteroaryl($C_1$-$C_3$)-alkyl;

the chemical moieties
$A_1$ represents $CR^2$ or N,
$A_2$ represents $CR^3$ or N,
$A_3$ represents $CR^4$ or N,
$A_4$ represents $CR^5$ or N,
$B_1$ represents $CR^6$ or N,
$B_2$ represents $CR^7$ or N,
$B_3$ represents $CR^8$ or N,
$B_4$ represents $CR^9$ or N, and
$B_5$ represents $CR^{10}$ or N;
but not more than three of the chemical moieties $A_1$ to $A_4$ simultaneously represent nitrogen and not more than three of the moieties $B_1$ to $B_5$ simultaneously represent nitrogen;
$R^2$, $R^3$, $R^4$, $R^5$, $R^6$, $R^7$, $R^9$ and $R^{10}$ independently of one another represent hydrogen, halogen, cyano, nitro, in each case optionally substituted $C_1$-$C_6$-alkyl, $C_3$-$C_7$-cycloalkyl, $C_1$-$C_6$-alkoxy, N—($C_1$-$C_6$-alkoxy)imino-$C_1$-$C_3$-alkyl, $C_1$-$C_6$-alkylsulfanyl, $C_1$-$C_6$-alkylsulfinyl, $C_1$-$C_6$-alkylsulfonyl, N—($C_1$-$C_6$-alkyl)amino or N,N-di($C_1$-$C_6$-alkyl)amino, $C_1$-$C_6$-alkylsulfonylamino N—($C_1$-$C_6$-alkyl)-$C_1$-$C_6$-alkylsulfonylamino;
$R^8$ represents halogen, cyano, nitro, an optionally substituted moiety selected from $C_1$-$C_6$-alkyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulfanyl, $C_1$-$C_6$-alkylsulfinyl, $C_1$-$C_6$-alkylsulfonyl, N—$C_1$-$C_6$-alkylamino and N,N-di-$C_1$-$C_6$-alkylamino;
$R^{11}$ and $R^{12}$ independently of one another represents hydrogen, halogen, cyano, nitro, amino or in each case an optionally halogenated moiety selected from $C_1$-$C_6$-alkyl, $C_1$-$C_6$-alkyloxy, $C_1$-$C_6$-alkylcarbonyl, $C_1$-$C_6$-alkylsulfanyl, $C_1$-$C_6$-alkylsulfinyl, $C_1$-$C_6$-alkylsulfonyl;
W is oxygen or sulfur;
Q is hydrogen, amino, a moiety selected from $C_1$-$C_6$-alkyl, $C_2$-$C_6$-alkenyl, $C_2$-$C_6$-alkynyl, $C_3$-$C_6$-cycloalkyl, $C_2$-$C_5$-heterocyclyl, $C_1$-$C_4$-alkoxy, $C_1$-$C_6$-alkyl-$C_3$-$C_6$-cycloalkyl, $C_3$-$C_6$-cycloalkyl-$C_1$-$C_6$-alkyl, aryl-($C_1$-$C_3$)-alkyl, heteroaryl-($C_1$-$C_3$)-alkyl, $C_1$-$C_4$-alkoxycarbonyl, in each case optionally monosubstituted to heptasubstituted independently of one another by cyano, alkoxy and alkoxycarbonyl; or a moiety selected from N—$C_1$-$C_4$-alkylamino, N—$C_1$-$C_4$-alkylcarbonylamino, N,N-di-$C_1$-$C_4$-alkylamino and $C_1$-$C_4$-alkylsulfonylamino; or a halogenated moiety selected from $C_1$-$C_6$-alkyl, $C_2$-$C_6$-alkenyl, $C_2$-$C_6$-alkynyl, $C_3$-$C_6$-cycloalkyl, $C_2$-$C_5$-heterocyclyl, $C_1$-$C_4$-alkoxy, $C_1$-$C_6$-alkyl-$C_3$-$C_6$-cycloalkyl, $C_3$-$C_6$-cycloalkyl-$C_1$-$C_6$-alkyl, aryl-($C_1$-$C_3$)-alkyl, heteroaryl-($C_1$-$C_3$)-alkyl, and $C_1$-$C_4$-alkoxycarbonyl; or
Q is an aryl substituted by 0, 1, 2, 3 or 4 V substituents or a 5- or 6-membered heteroaryl substituted by 0, 1, 2, 3 or 4 V substituents, where
V independently of one another represents halogen, cyano, nitro, a moiety selected from $C_1$-$C_6$-alkyl, $C_2$-$C_4$-alkenyl, $C_2$-$C_4$-alkynyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulfanyl, $C_1$-$C_6$-alkylsulfinyl, $C_1$-$C_6$-alkylsulfonyl and N,N-di-($C_1$-$C_6$-alkyl)amino, in each case optionally monosubstituted to heptasubstituted independently of one another by cyano, alkoxy and alkoxycarbonyl, or a halogenated moiety selected from $C_1$-$C_6$-alkyl, $C_2$-$C_4$-alkenyl, $C_2$-$C_4$-alkynyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulfanyl, $C_1$-$C_6$-alkylsulfinyl, $C_1$-$C_6$-alkylsulfonyl and N,N-di-($C_1$-$C_6$-alkyl)amino;

or a salt, N-oxide or a tautomeric form of a compound of formula (I).

2. The compound as claimed in claim 1, wherein $B_1$ is $CR^6$, $B_2$ is $CR^7$, $B_3$ is $CR^8$, $B_4$ is $CR^9$ and $B_5$ is $CR^{10}$, or a salt, N-oxide or a tautomeric form thereof.

3. The compound as claimed in claim 1, wherein $R^6$ is halogen or optionally halogenated $C_1$-$C_6$-alkyl or optionally halogenated $C_1$-$C_6$-alkoxy, $R^7$ is hydrogen, $R^8$ is halogenated $C_1$-$C_6$-alkyl, $R^9$ is hydrogen and $R^{10}$ is halogen or optionally halogenated $C_1$-$C_6$-alkyl or optionally halogenated $C_1$-$C_6$-alkoxy, or a salt, N-oxide or a tautomeric form thereof.

4. The compound as claimed in claim 1, wherein $R^{11}$ and $R^{12}$ are hydrogen and W is oxygen, or a salt, N-oxide or a tautomeric form thereof.

5. The compound as claimed in claim 1, wherein $A_1$ is $CR^2$, $A_2$ is $CR^3$ or N, $A_3$ is $CR^4$ or N and $A_4$ is $CR^5$ and $R^2$ is hydrogen or $C_1$-$C_6$-alkyl and $R^3$, $R^4$ and $R^5$ are each independently of one another hydrogen, halogen, CN, optionally halogenated $C_1$-$C_6$-alkyl or optionally halogenated N,N-di-$C_1$-$C_6$-alkylamino, or a salt, N-oxide or a tautomeric form thereof.

6. The compound as claimed in claim 1, wherein Q is
$C_1$-$C_6$-alkyl optionally substituted by one, two or three substituents selected from the group consisting of oxo, cyano, nitro and amino,
halogenated ($C_1$-$C_6$)-alkyl,
$C_3$-$C_6$-cycloalkyl optionally substituted by one, two or three substituents selected from the group consisting of halogen, cyano, nitro, $C_1$-$C_3$-alkyl and amino,
$C_2$-$C_5$-heterocyclyl optionally substituted with one, two or three substituents selected from the group consisting of halogen, cyano, nitro, $C_1$-$C_3$-alkyl and amino,
an aryl substituted by 0, 1, 2, 3 or 4 V substituents or
a 5- or 6-membered heteroaryl substituted by 0, 1, 2, 3 or 4 V substituents, wherein
V is independently of one another halogen, cyano, $C_1$-$C_6$-alkyl or $C_1$-$C_6$-alkoxy, or a salt, N-oxide or a tautomeric form thereof.

7. The compound as claimed in claim 1, wherein Q is
$C_3$-$C_6$-cycloalkyl optionally substituted by one substituent selected from the group consisting of halogen, $C_1$-$C_3$-alkyl and cyano, or
$C_2$-$C_5$-heterocyclyl optionally substituted by one substituent selected from the group consisting of halogen or cyano, or
an aryl substituted by 0, 1 or 2 V substituents, or a 5- or 6-membered heteroaryl substituted by 0, 1, 2, 3 or 4 V substituents, wherein V is independently of one another halogen, cyano, $C_1$-$C_6$-alkyl or $C_1$-$C_6$-alkoxy, or a salt, N-oxide or a tautomeric form thereof.

8. The compound as claimed in claim 1, wherein Q is
cyclopropyl optionally substituted by cyano or $C_1$-$C_3$-alkyl, or
thietanyl (thiacyclobutanyl) optionally substituted by cyano or $C_1$-$C_3$-alkyl, or
phenyl substituted by 0, 1 or 2 V substituents each selected independently of one another from the group consisting of F, Cl, $C_1$-$C_3$-alkoxy, $C_1$-$C_3$-alkyl, halogenated $C_1$-$C_3$-alkyl and cyano, or
pyridyl, pyrimidinyl, thienyl, or oxazolyl substituted by 0, 1 or 2 V substituents each selected independently of one another from the group consisting of F, Cl, $C_1$-$C_3$-alkyl, halogenated $C_1$-$C_3$-alkyl and cyano, or a salt, N-oxide or a tautomeric form thereof.

9. The compound according to claim 1, where
$A_1$ represents $CR^2$, where $R^2$ represents hydrogen,
$A_2$ represents $CR^3$ or N, where $R^3$ represents hydrogen,
$A_3$ represents $CR^4$ or N, where $R^4$ is hydrogen, Cl, F, or $C_1$-$C_3$-alkyl or —N($C_1$-$C_3$-alkyl)$_2$,
$A_4$ represents $CR^5$, where $R^5$ represents hydrogen or F,
$B_1$ represents $CR^6$,
$B_2$ represents $CR^7$, where $R^7$ represents hydrogen,
$B_3$ represents $CR^8$,
$B_4$ represents $CR^9$, where $R^9$ represents hydrogen,
$B_5$ represents $CR^{10}$
$R^6$ represents Cl, Br or $C_1$-$C_3$-alkyl,
$R^8$ represents perhalogenated $C_1$-$C_6$-alkyl,
$R^{10}$ represents Cl, $C_1$-$C_3$-alkyl or perfluorinated $C_1$-$C_3$-alkyl,
$R^{11}$ and $R^{12}$ represent hydrogen,
W is oxygen,
Q represents (a) $C_3$-$C_6$-cycloalkyl optionally substituted by one substituent selected from the group consisting of halogen, $C_1$-$C_3$-alkyl and cyano, (b) $C_2$-$C_5$-heterocyclyl optionally substituted by one substituent selected from the group consisting of halogen, cyano, or $C_1$-$C_3$-alkyl, (c) an aryl substituted by 0, 1 or 2 V substituents or a 5- or 6-membered heteroaryl substituted by 0, 1, 2, 3 or 4 V substituents, wherein V is each independently of one another halogen, cyano, optionally halogenated $C_1$-$C_6$-alkyl, optionally halogenated $C_1$-$C_6$-alkoxy, or a salt, N-oxide or a tautomeric form thereof.

10. The compound as claimed in claim 1, wherein the compound of the formula (I) is a compound of formula (I'):

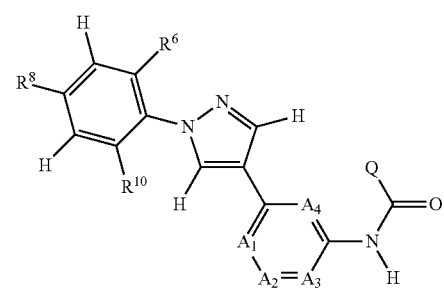

or a salt, N-oxide or a tautomeric form thereof.

11. The compound as claimed in claim 1, wherein the compound of the formula (I) is a compound of formula (Ia):

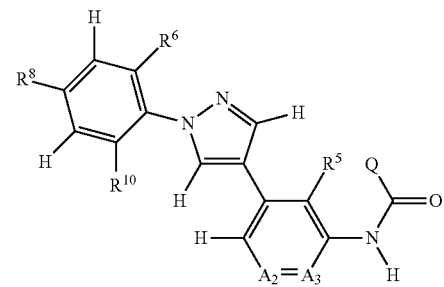

or a salt, N-oxide or a tautomeric form thereof.

12. The compound as claimed in claim 1, wherein the compound of the formula (I) is a compound of formula (Ib):

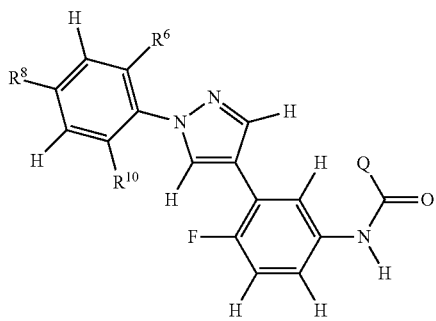

(Ib)

or a salt, N-oxide or a tautomeric form thereof.

13. A pharmaceutical composition comprising a pharmaceutically acceptable auxiliary and at least one compound or salt, N-oxide or tautomeric form thereof as claimed in claim 1.

14. The compound or salt, N-oxide or tautomeric form thereof according to claim 1, wherein
$R^8$ represents halogen, cyano, nitro or halogenated $C_1$-$C_6$-alkyl.

15. The compound according to claim 9, wherein
$A_3$ represents $CR^4$ or N, where $R^4$ is hydrogen, Cl, F, $CH_3$ or $N(CH_3)_2$,
$R^8$ represents perfluorinated $C_1$-$C_4$-alkyl,
$R^{10}$ represents Cl, methyl or $CF_3$,
Q represents (a) cyclopropyl optionally substituted by cyano or $C_1$-$C_3$-alkyl, (b) thietanyl (thiacyclobutanyl) optionally substituted by cyano or $C_1$-$C_3$-alkyl, (c) an aryl substituted by 0, 1 or 2 V substituents or a 5- or 6-membered heteroaryl substituted by 0, 1, 2, 3 or 4 V substituents, wherein V is each independently of one another F, Cl, cyano, optionally halogenated $C_1$-$C_6$-alkyl, optionally halogenated $C_1$-$C_6$-alkoxy,
or a salt, N-oxide or a tautomeric form thereof.

16. The compound according to claim 15, wherein
Q represents (a) cyclopropyl optionally substituted by cyano or $C_1$-$C_3$-alkyl, (b) thietanyl (thiacyclobutanyl) optionally substituted by cyano or $C_1$-$C_3$-alkyl, (c) phenyl optionally substituted by 0, 1 or 2 V substituents each selected independently of one another from the group consisting of F, Cl, methoxy, ethoxy, methyl, $CF_3$ and cyano; or pyridyl, pyrimidinyl, thienyl, or oxazolyl optionally substituted by 0, 1 or 2 V substituents each selected independently of one another from the group consisting of F, Cl, methyl, $CF_3$ and cyano,
or a salt, N-oxide or a tautomeric form thereof.

17. The compound as claimed in claim 11, wherein
$A_2$ represents CH,
$A_3$ represents CH,
Q represents 4-F-phenyl,
$R^5$ represents F,
$R^6$ represents Br,
$R^8$ represents iso-$C_3F_7$,
$R^{10}$ represents $CF_3$,
or a salt, N-oxide or a tautomeric form thereof.

* * * * *